US010350211B2

(12) United States Patent
Van Voorhis et al.

(10) Patent No.: US 10,350,211 B2
(45) Date of Patent: Jul. 16, 2019

(54) BUMPED KINASE INHIBITOR COMPOSITIONS AND METHODS FOR TREATING CANCER

(71) Applicant: UNIVERSITY OF WASHINGTON, Seattle, WA (US)

(72) Inventors: Wesley C. Van Voorhis, Seattle, WA (US); Erkang Fan, Seattle, WA (US); Dustin James Maly, Seattle, WA (US); Kayode K. Ojo, Seattle, WA (US); Stephen R. Plymate, Seattle, WA (US); Rama Subba Rao Vidadala, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 15/544,598

(22) PCT Filed: Jan. 26, 2016

(86) PCT No.: PCT/US2016/014995
§ 371 (c)(1),
(2) Date: Jul. 19, 2017

(87) PCT Pub. No.: WO2016/123151
PCT Pub. Date: Aug. 4, 2016

(65) Prior Publication Data
US 2018/0271871 A1 Sep. 27, 2018

Related U.S. Application Data
(60) Provisional application No. 62/131,539, filed on Mar. 11, 2015, provisional application No. 62/107,746, filed on Jan. 26, 2015.

(51) Int. Cl.
*A61K 31/519* (2006.01)
*A61P 33/02* (2006.01)
*A61P 35/00* (2006.01)
*A61K 31/4985* (2006.01)
*C07D 487/04* (2006.01)

(52) U.S. Cl.
CPC ........ *A61K 31/519* (2013.01); *A61K 31/4985* (2013.01); *A61P 33/02* (2018.01); *A61P 35/00* (2018.01); *C07D 487/04* (2013.01); *Y02A 50/411* (2018.01); *Y02A 50/488* (2018.01)

(58) Field of Classification Search
CPC ... A61K 31/519; A61K 31/4985; A61P 33/02; A61P 35/00; C07D 487/04
USPC ........................................................ 514/262.1
See application file for complete search history.

(56) References Cited

U.S. PATENT DOCUMENTS

| 2003/0187001 | A1 | 10/2003 | Calderwood |
| 2006/0235031 | A1 | 10/2006 | Arnold et al. |
| 2008/0014200 | A1 | 1/2008 | Arnold |
| 2009/0099178 | A1 | 4/2009 | Bhagwat et al. |
| 2011/0224223 | A1* | 9/2011 | Shokat ................... C12Q 1/485 514/252.18 |
| 2013/0018040 | A1 | 1/2013 | Van Voorhis et al. |

FOREIGN PATENT DOCUMENTS

| DE | 102004063269 A1 | 7/2006 |
| WO | 2008/074997 A1 | 6/2008 |
| WO | 2009/150230 A1 | 12/2009 |
| WO | 2011/057064 A1 | 5/2011 |
| WO | 2011/094628 A1 | 8/2011 |
| WO | 2012/078859 A2 | 6/2012 |

OTHER PUBLICATIONS

Voorhis et al. Exp. Parasitol. 2017, 180, 71-83 (Year: 2017).*
Aspel et al Nature Chemical biology, 2008, 4(11) 691-698 (Year: 2008).*
The International Search Report for PCT/US2016/014995 dated Mar. 6, 2016, pp. 1-3.
Written Opinion of the International Searching Authority for PCT/US2016/014995 dated Mar. 6, 2016, pp. 1-10.
Ajjampur et al., "Closing the diarrhea diagnostic gap in Indian children by the application of molecular techniques," J. Med. Microbiol. 57(Pt 11): 1364-1368 (2008).
Apsel et al., "Targeted polypharmacology: discovery of dual inhibitors of tyrosine and phosphoinositide kinases," Nat. Chem. Biol., 4(11): 691-699 (2008).
Billker et al., "Calcium-dependent signaling and kinases in apicomplexan parasites,"Cell Host Microbe. 5(6):612-22 (2009).
Bishop et al., "A chemical switch for inhibitor-sensitive alleles of any protein kinase," Nature 407(6802): 395-401 (2000).
Bishop et al., "Design of allele-specific inhibitors to probe protein kinase signaling," Curr. Biol. 8(5): 257-266 (1998).
Bishop et al., "Generation of monospecific nanomolar tyrosine kinase inhibitors via a chemical genetic approach," J. Am. Chem. Soc. 121(4): 627-631 (1999).
Burchat et al., "Pyrazolo[3,4-d]pyrimidines containing an extended 3-substituent as potent inhibitors of Lck—a selectivity insight," Bioorg. Med. Chem. Lett., 12(12): 1687-1690 (2002).

(Continued)

*Primary Examiner* — Yevgeny Valenrod
(74) *Attorney, Agent, or Firm* — McDonnell Boehnen Hulbert & Berghoff LLP

(57) ABSTRACT

The present disclosure is generally directed to bumped kinase inhibitor (BKI) compositions and methods for treating cancer.

12 Claims, 6 Drawing Sheets

(56) References Cited

OTHER PUBLICATIONS

Chen et al., "Apical Organelle discharge by Cryptosporidium parvum is temperature, cytoskeleton, and intracellular calcium dependent and required for host cell invasion," Infect. Immun. 72(12): 6806-16 (2004).
Cohen et al., "Structural bioinformatics-based design of selective, irreversible kinase inhibitors," Science 308(5726): 1318-1321 (2005).
Doerig et al., "Protein kinases as targets for antimalarial intervention: kinomics, structure-based design, transmission-blockade, and targeting host cell enzymes," Biophysica et Biochimica Acta—Proteins and Proteomics 1754(1-2): 132-150 (2005).
Hanke et al., "Discovery of a novel, potent, and Src family-selective tyrosine kinase Inhibitor: Study of Lck- and FynT-dependent T cell activation," J. Biol. Chem. 271(2): 695-701 (1996).
Hines et al., "Theileria equi isolates vary in susceptibility to imidocarb dipropionate but demonstrate uniform in vitro susceptibility to a bumped kinase inhibitor," Parasit Vectors. 8:33 (2015).
Huang et al., "SAR Studies of 5-Aminopyrazole-4-carboxamide Analogues as Potent and Selective Inhibitors of Toxoplasma gondii CDPK1," ACS Med Chem Lett. 6(12):1184-1189 (2015).
Keyloun et al., "The gatekeeper residue and beyond: homologous calcium-dependent protein kinases as drug development targets for veterinarian Apicomplexa parasites," Parasitology. 141(11):1499-509 (2014).
Kieschnick et al., "Toxoplasma gondii attachment to host cells is regulated by a calmodulin-like domain protein kinase," J. Biol. Chem. 276(15): 12369-12377 (2001).
Lender et al., "A novel CDPK1 inhibitor-a potential treatment for cryptosporidiosis in calves?" Parasitol Res. 114(1):335-6 (2015).
Liao, JJ. "Molecular recognition of protein kinase binding pockets for design of potentand selective kinase inhibitors," J. Med. Chem. 50(3): 409-424 (2007).
Montoya et al., Chapter 276: Toxoplasma gondii in Mandell, Bennett, & Dolin: Principles and Practice of Infectious Diseases, 6th ed. Publ: Churchill Livingston (2005).
Nagamune and Sibley, "Comparative genomic and phylogenetic analyses of calcium ATPases and calcium-regulated proteins in the apicomplexa," Mol. Biol. Evol. 23(8): 1613-1627 (2006).
Ojo et al., "Transmission of malaria to mosquitoes blocked by bumped kinase inhibitors," J. Clin. Invest. 122(6):2301-2305 (2012).
Ojo et al., "Neospora caninum Calcium-Dependent Protein Kinase 1 Is an Effective Drug Target for Neosporosis Therapy," PLoS One, 9(3):e92929 (2014).
Pedroni et al., "Bumped kinase inhibitor prohibits egression in Babesia bovis," Vet Parasitol 215:22-8 (2016).
Samie et al., "Cryptosporidium species: preliminary descriptions of the prevalence and genotype distribution among school children and hospital patients in the Venda region, Limpopo Province, South Africa," Exp.Parasitol. 114(4):314-322 (2006).
Sugi et al., "Use of the kinase inhibitor analog 1NM-PP1 reveals a role for Toxoplasma gondii CDPK1 in the invasion step," Eukaryot. Cell 9(4): 667-70. (2010).
Valeur and Roche. "Efficient, mild, parallel and purification-free synthesis of arylethers via Mitsunobu reaction," Tet. Lett. 49(23): 4182-4185 (2008).
White AC., Jr. Chapter 280: Cryptosporidiosis (*Cryptosporidium hominis*, *Cryptosporidium parvum*, and Other Species) in Mandell, Bennett, & Dolin: Principles and Practice of Infectious Diseases, 6th ed. Publ: Churchill Livingston (2005).
Winzer et al. "In Vitro and In Vivo Effects of the Bumped Kinase Inhibitor 1294 in the Related Cyst-Forming Apicomplexans Toxoplasma gondii and Neospora caninum," Antimicrob Agents Chemother 59(10):6361-74 (2015).
Zhang et al., "A second-site suppressor strategy for chemical genetic analysis of diverse protein kinases," Nat. Methods 2(6): 435-441 (2005).

Zhang et al., "Benzoylbenzimidazole-based selective inhibitors targeting Cryptosporidium parvum and Toxoplasma gondii calcium-dependent protein kinase-1," Bioorg Med Chem Lett. 22(16):5264-7 (2012).
Zhang et al., "Potent and Selective Inhibitors of CDPK1 from T. gondii and C. parvum Based on a 5-Aminopyrazole-4-carboxamide Scaffold," ACS Med. Chem. Letters. 5(1): 40-44 (2013).
Doggett et al., "Bumped Kinase Inhibitor 1294 Treats Established Toxoplasma gondii Infection," Antimicrobial Agents Chemotheraphy, 58(6): 3547-3549 (2014).
Gilbert et al., "Ocular sequelae of congenital toxoplasmosis in Brazil compared with Europe," PLoS Negl. Trop. Dis. 2(8):e277 (2008).
Demar et al. "Acute toxoplasmoses in immunocompetent patients hospitalized in an intensive care unit in French Guiana," Clin. Microbiol. Infect. 18:E221-E231 (2012).
Lourido et al., "Calcium-dependent protein kinase 1 is an essential regulator of exocytosis in Toxoplasma," Nature 465:359-362 (2010).
Ojo et al., "Toxoplasma gondii calcium-dependent protein kinase 1 is a target for selective kinase inhibitors," Nat. Struct. Mol. Biol. 17(5):602-607 (2010).
Murphy et al. "Discovery of potent and selective inhibitors of calcium-dependent protein kinase 1 (CDPK1) from C. parvum and T. gondii," ACS Med. Chem. Lett. 1(7):331-335 (2010).
Sugi et al., "Identification of mutations in TgMAPK1 of Toxoplasma gondii conferring resistance to 1NM-PP1," Int. J. Parasitol. Drugs Drug Resist. 3:93-101 (2013).
Johnson et al., "Development of Toxoplasma gondii calcium-dependent protein kinase 1 (TgCDPK1) inhibitors with potent anti-toxoplasma activity," J. Med. Chem. 55(5): 2416-2426 (2012).
Larson et al., "Multiple determinants for selective inhibition of apicomplexan calcium-dependent protein kinase CDPK1," J. Med. Chem. 55(6):2803-2810 (2012).
Lourido et al. "Optimizing small molecule inhibitors of calcium-dependent protein kinase 1 to prevent infection by Toxoplasma gondii," J. Med. Chem. 56(7):3068-3077 (2013).
Ojo et al., "A specific inhibitor of PfCDPK4 blocks malaria transmission: Chemical-genetic validation," J. Infect. Dis. 209(2):275-284 (2014).
Castellanos-Gonzalez et al., "A novel calcium dependent protein kinase inhibitor as a lead compound for treating cryptosporidiosis," J. Infect. Dis. 208(8):1342-1348 (2013).
Sugi et al., "1NM-PP1 treatment of mice infected with Toxoplasma gondii," J. Vet. Med. Sci. 73(10):1377-1379 (2011).
Vidadala et al., "Development of potent and selective Plasmodium falciparum calcium-dependent protein kinase 4 (PfCDPK4) inhibitors that block the transmission of malaria to mosquitoes," Eur J Med Chem 74: 562-73 (2014).
Tandon et al., "New Pyrazolopyrimidine Inhibitors of Protein Kinase D as Potent Anticancer Agents for Prostate Cancer," PLoS One 8(9): e75601 (2013).
Chen et al., "Protein kinase D3 (PKD3) contributes to prostate cancer cell growth and survival through a PKCepsilon/PKD3 pathway downstream of Akt and ERK 1/2," Cancer Res. 68(10):3844-53 (2008).
Lavalle et al. "Novel protein kinase D inhibitors cause potent arrest in prostate cancer cell growth and motility," BMC Chemical Biology 10:5 (2010).
Zou et al., "PKD2 and PKD3 promote prostate cancer cell invasion by modulating NF-κB- and HDAC1-mediated expression and activation of uPA," J Cell Sci. 125(Pt 20):4800-11 (2012).
Lavalle et al., "Inducible silencing of protein kinase D3 inhibits secretion of tumor-promoting factors in prostate cancer," J. Mol Cancer Ther. 11(7):1389-99 (2012).
Deng et al., "PKD3 contributes to up-regulation of prostate-specific antigen in prostate cancer cells," Nan Fang Yi Ke Da Xue Xue Bao. 30(8):1779-82 (2010).
Zou et al., "Protein kinase D3 is involved in negative regulation of MMP-7 in prostate cancer cells," Nan Fang Yi Ke Da Xue Xue Bao. 30(8):1767-70 (2010).
The International Search Report (ISR) for PCT/US2016/014996, dated Mar. 4, 2016, pp. 1-3.

(56) References Cited

OTHER PUBLICATIONS

Written Opinion of the International Searching Authority for PCT/US2016/014996, dated Mar. 4, 2016, pates 1-5.

\* cited by examiner

A

| Time | 1 hr after dose 1 | 24 hr after dose 1 | 1 hr after dose 5 | 24 hr after dose 5 | 72 hr after dose 5 |
|---|---|---|---|---|---|
| Conc. (mM) | 38.5 | 62.1 | 124.1 | 109.6 | 84.9 |

B

A

B

BUMPED KINASE INHIBITOR COMPOSITIONS AND METHODS FOR TREATING CANCER

CROSS-REFERENCE TO RELATED APPLICATIONS

This application is a U.S. national phase of International Application No. PCT/US2016/014995, filed on Jan. 26, 2016, which claims priority to U.S. Provisional Application No. 62/131,539, filed Mar. 11, 2015 and U.S. Provisional Application No. 62/107,746, filed Jan. 26, 2015, all of which are incorporated by reference herein in their entirety.

STATEMENT OF GOVERNMENT SUPPORT

This invention was made with government support under Grant No. 5R01AI089441-04, awarded by the National Institutes of Health. The government has certain rights in the invention.

FIELD OF THE INVENTION

The present disclosure is generally directed to bumped kinase inhibitor (BKI) compositions and methods for treating cancer.

BACKGROUND OF THE INVENTION

More than one million people in the United States get cancer each year. Although the five year survival rate has risen dramatically nearly fifty percent as a result of progress in early diagnosis and therapy, cancer still remains second only to cardiac disease as a cause of death in the United States. Breast, lung and bronchus, and colorectal cancer are the 3 most common cancers diagnosed in women, and in men, prostate, lung and bronchus, and colorectal cancers are the most commonly diagnosed. Designing effective treatments for patients with cancer still represents a major challenge.

Prostate cancer is the most common cancer in men and one of the leading causes of cancer death. Historically treatment of high-grade, recurrent prostate cancer has been to dramatically reduce the supply of androgens to the cancer via castration. Since signaling through the androgen receptor drives prostate cancer progression, removing the receptor's ligand (androgens) inhibits prostate cancer tumor growth, at least initially. However, resistance to androgen deprivation therapy (ADT) occurs in almost all patients leading to development of castrate resistant prostate cancer (CRPC). Resistance to ADT, and, in particular, the newest androgen receptor (AR)-directed therapies such as enzalutamide and abiraterone, is associated with expression of splice variants of the AR (AR-Vs) that are constitutively active. Directly targeting the AR-Vs has been problematic due to the intrinsically disordered nature of the AR N-terminus.

SUMMARY OF THE INVENTION

We recognized a need for therapies that indirectly target AR by inhibiting factors important in regulating AR levels and activity and have the greatest impact on inhibiting further progression of cancer. The protein kinase D (PKD) family is a subfamily of the Calcium-Calmodulin kinase superfamily, and PKD family members, PKD1, PKD2 and PKD3 are essential regulators of cell migration, proliferation and protein transport. Expression of PKD isoforms varies by cancer type and even within patients. In prostate cancer, expression of all PKD isoforms (PKD1, 2, and 3) has been shown to increase with cancer progression. Nuclear localization of PKD3, in particular, is correlated with more advanced cancers and poorer outcomes. Further, PKD2 and 3 are implicated in prostate cancer (PCa) replication, migration, invasion, and progression. In breast cancer, PKD isoforms exhibit distinct expression patterns and regulate various oncogenic processes. In highly invasive breast cancer, the leading cause of cancer-associated deaths in females, the loss of PKD1 is thought to promote invasion and metastasis, while PKD2 and upregulated PKD3 have been shown to be positive regulators of proliferation, chemoresistance, and metastasis. For example, upregulation of PKD3 leads to all hallmarks of aggressive invasive ductal carcinomas (IDC) of the breast, including increased cell proliferation, migration, and invasion. In regard to AR activity, some studies suggest that PKDs in conjunction with heat shock protein 27 (Hsp27) are regulators of AR transport into and out of the nucleus as well as AR transcriptional activity. These studies also demonstrate the presence of PKD/Hsp27/AR complexes on chromatin of AR regulated genes (such as prostate specific antigen (PSA)). Thus, targeting PKDs would affect AR signaling and thus be a promising anticancer therapy.

While the bumped kinase inhibitors (BKIs) were originally designed to inhibit *Cryptosporidium* sp. via binding calcium-dependent protein kinase 1 (CDPK1) in the ATP-binding site, we determined that this class of BKIs also inhibits members of the mammalian protein kinase D (PKD) family. Thus, one aspect of the disclosure provides method for treating cancer comprising administering to a patient in need of such treatment a therapeutically effective amount of:

(i) a bumped kinase inhibitor of formula (I):

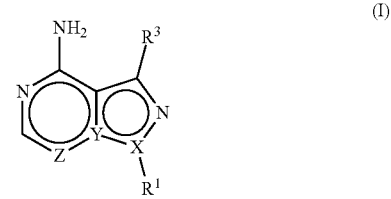

or a pharmaceutically acceptable salt thereof, wherein
X, Y, and Z are defined by either: (i) X is N, Y is C, and Z is N; or (ii) X is C, Y is N, and Z is C(H);
$R^1$ is $C_{2-6}$ alkyl, $C_{1-6}$ haloalkyl, —$C_{1-6}$ alkyl-$R^{12}$, $C_{2-6}$ alkenyl, $C_{2-6}$ alkynyl, $C_{3-8}$ cycloalkyl, heterocyclyl, heteroaryl, or aryl, wherein
the alkyl, cycloalkyl, heterocyclyl, heteroaryl, and aryl groups are each optionally substituted with one or two $R^{11}$ groups;
each $R^{11}$ is independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2NR_2$, or —S(O)$_2$R; and
$R^{12}$ is —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$ haloalkyl, $C_{1-6}$ hydoxyalkyl, —OR, —SR, —$NR_2$, —C(O)R, —C(O)

OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;

R$^3$ is one of the formulas,

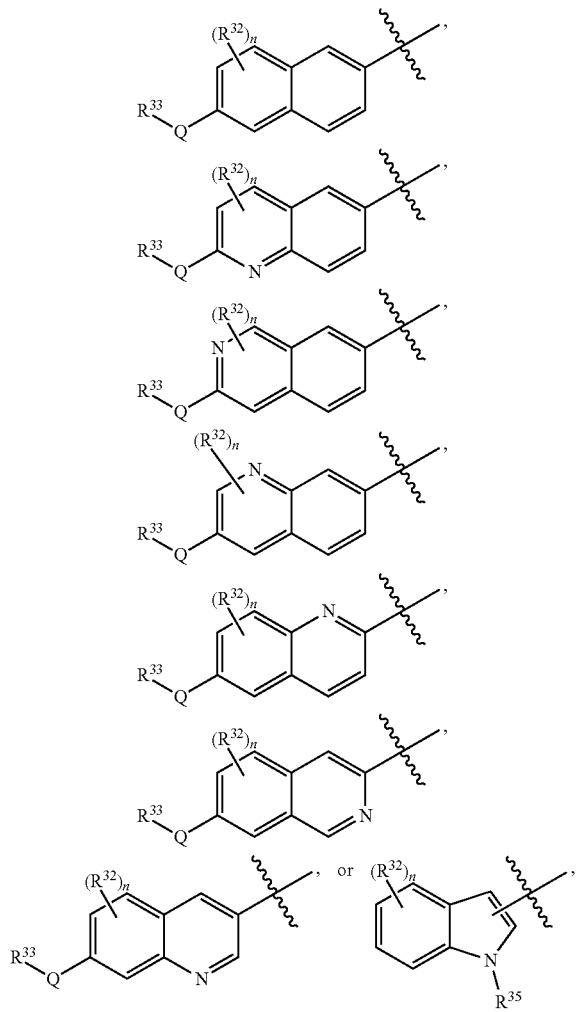

wherein
  n is 0, 1, or 2;
  Q is —O—, —S—, or —N(R$^Q$)—, wherein R$^Q$ is hydrogen or C$_{1-6}$ alkyl; and
  R$^{33}$ is C$_{1-6}$ alkyl, C$_{2-6}$ alkenyl, C$_{1-6}$ haloalkyl, C$_{3-8}$ cycloalkyl, (C$_{3-8}$ cycloalkyl)C$_{1-6}$ alkyl, heterocyclyl, (heterocyclyl)C$_{1-6}$ alkyl, aryl, arylC$_{1-6}$ alkyl, heteroaryl, or heteroarylC$_{1-6}$ alkyl wherein the alkyl, cycloalkyl, heterocyclyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or —N(R$^{20}$)C(O)N(R$^{20}$)$_2$, wherein each R$^{20}$ is independently hydrogen or C$_{1-6}$ alkyl,
  each R$^{32}$ is independently halogen, cyano, nitro, C$_{1-6}$ alkyl, C$_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each R$^{34}$ is independently hydrogen or C$_{1-6}$ alkyl;
  and
  R$^{35}$ is hydrogen or C$_{1-6}$ alkyl;
and
each R is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R, —N(R$^0$)C(O)OR$^0$, or —N(R$^0$)C(O)N(R$^0$)$_2$, wherein each R$^0$ is independently hydrogen or C$_{1-6}$ alkyl;
  (ii) a pharmaceutical composition comprising the bumped kinase inhibitor of formula (I) and a pharmaceutically acceptable excipient, carrier, or diluent.

In another aspect of the disclosure provides method for treating cancer comprising administering to a patient in need of such treatment a therapeutically effective amount of: (i) a bumped kinase inhibitor of formula (I), or (ii) a pharmaceutical composition comprising the bumped kinase inhibitor of formula (I) and a pharmaceutically acceptable excipient, carrier, or diluent, wherein the cancer is a solid tumor.

In yet another aspect of the disclosure provides method for treating cancer comprising administering to a patient in need of such treatment a therapeutically effective amount of: (i) a bumped kinase inhibitor of formula (I), or (ii) a pharmaceutical composition comprising the bumped kinase inhibitor of formula (I) and a pharmaceutically acceptable excipient, carrier, or diluent, wherein the cancer is prostate, testicular, penile, breast, ovarian, cervical, lung, liver, kidney, gastrointestinal, or colon cancer.

DETAILED DESCRIPTION OF THE INVENTION

Figure 1:
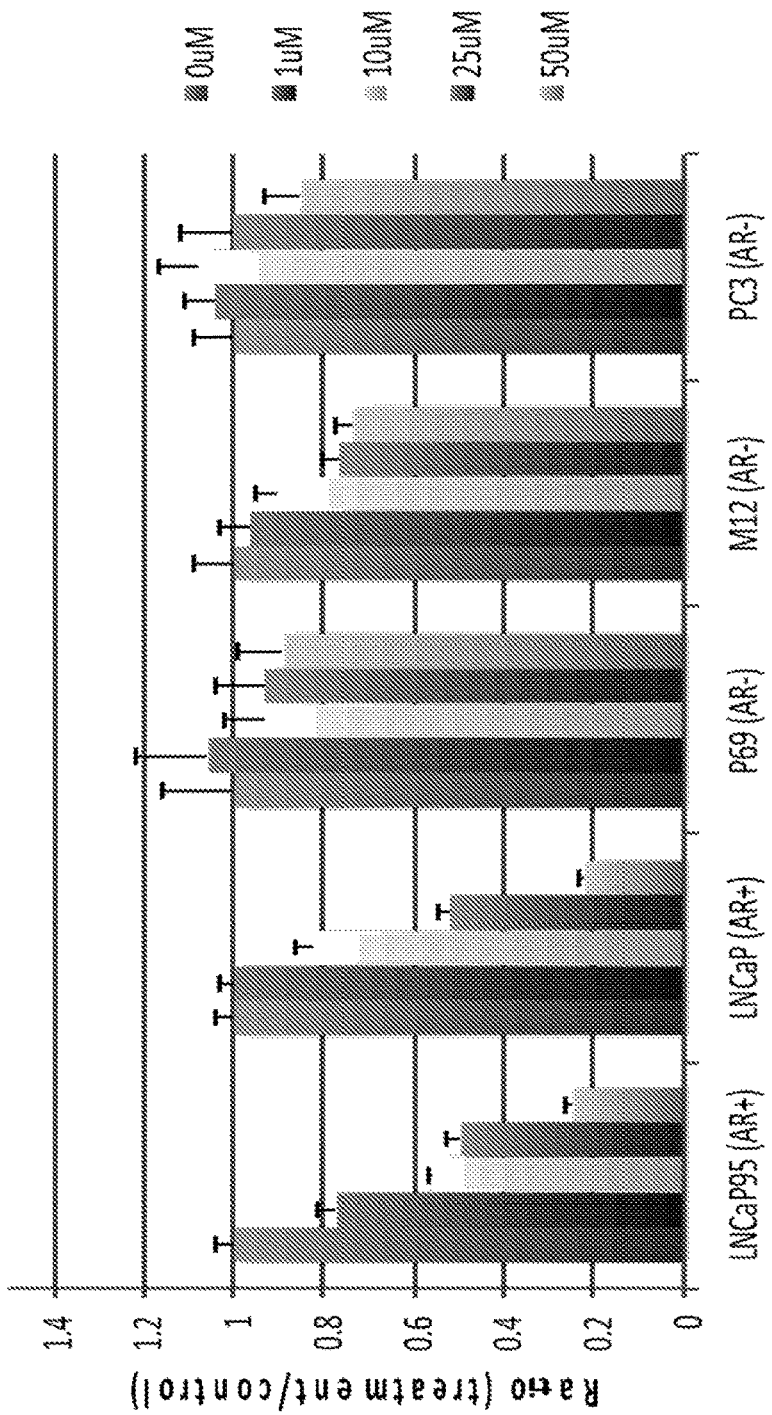
FIG. 1 shows cell proliferation of AR+PCa cell lines with treatment of Example 24. Cells were plated in 96-well plates and proliferation was measured by the MTS assay 96 hours after treatment with Example 24. Results are an average of three experiments. Error bars represent standard deviation of the mean.

Before the disclosed methods are described, it is to be understood that the aspects described herein are not limited to specific embodiments, or compositions, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

The term "pharmaceutical composition" is used in its widest sense, encompassing all pharmaceutically applicable compositions containing at least one active substance, and optional carriers, adjuvants, constituents etc. The term "pharmaceutical composition" also encompasses a composition comprising the active substance in the form of derivative or pro-drug, such as pharmaceutically acceptable salts and esters. The manufacture of pharmaceutical compositions for different routes of administration falls within the capabilities of a person skilled in medicinal chemistry.

In view of the present disclosure, the methods described herein can be configured by the person of ordinary skill in the art to meet the desired need. In general, the disclosed methods provide improvements in the treatment and/or prevention of cancer. For example, in particular embodiments, the BKIs of the disclosure effectively treat cancer, such as cancers responsive to the inhibition of androgen receptor activity. In addition, the BKIs of the disclosure had no measureable toxicity and excellent pharmacokinetic properties in vivo. Uniquely, compared to other potential PKD inhibitors, BKIs of the disclosure is selectively active against PCa cells expressing the androgen receptor (AR). In another embodiment, the cancer is androgen receptor (AR) positive prostate cancer.

The BKIs of the disclosure also reduced tumor growth in a PKD positive castrate resistant PCa xenograft driven by the constitutively active AR-V7 variant. In one embodiment of the methods of the disclosure, the cancer is castrate resistant prostate cancer (CRPC).

In another embodiment, the disclosure provides methods of treating breast cancer. In another embodiment, the cancer is protein kinase D (PKD)-expressing breast cancer.

In some embodiments of this disclosure, the subject in need is a human subject or patient. In some embodiments the subject, e.g., a human, has been previously treated with an anti-cancer therapy. In some other embodiments the subject has not been previously treated with an anti-cancer therapy.

The methods of the disclosure require a bumped kinase inhibitor (BKI) or a pharmaceutically acceptable salt thereof. Numerous BKIs are known in the art. Some BKIs are disclosed in, for example, International Patent Publication WO 2011/0094628 and the U.S. Patent Publication 2013/0018040, both incorporated herein by reference.

In certain embodiments of the methods of the disclosure, the BKIs are of formula (I),

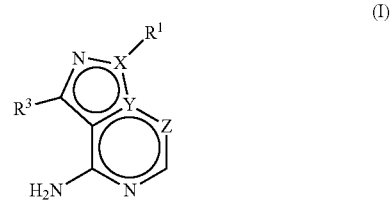

(I)

or a pharmaceutically acceptable salt thereof, wherein
X, Y, and Z are defined by either: (i) X is N, Y is C, and Z is N; or (ii) X is C, Y is N, and Z is C(H);
$R^1$ is $C_{2-6}$ alkyl, $C_{1-6}$ haloalkyl, —$C_{1-6}$ alkyl-$R^{12}$, $C_{2-6}$ alkenyl, $C_{2-6}$ alkynyl, $C_{3-8}$ cycloalkyl, heterocyclyl, heteroaryl, or aryl, wherein
  the alkyl, cycloalkyl, heterocyclyl, heteroaryl, and aryl groups are each optionally substituted with one or two $R^{11}$ groups;
  each $R^{11}$ is independently halogen, cyano, nitro, $C_{1-6}$ alkyl, $C_{1-6}$ haloalkyl, —OR, —SR, —$NR_2$, —C(O)R, —C(O)OR, —C(O)$NR_2$, —S(O)$_2NR_2$, or —S(O)$_2$R; and
$R^{12}$ is —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, —N(R)C(O)$NR_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$ haloalkyl, $C_{1-6}$ hydoxyalkyl, —OR, —SR, —$NR_2$, —C(O)R, —C(O)OR, —C(O)$NR_2$, —S(O)$_2$R, —OC(O)R, —OC(O)OR, —OC(O)$NR_2$, —N(R)C(O)R, —N(R)C(O)OR, or —N(R)C(O)$NR_2$;
$R^3$ is one of the formulas,

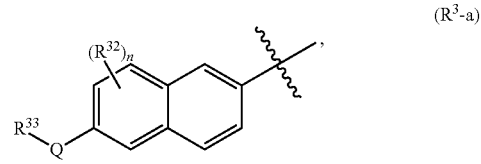

($R^3$-a)

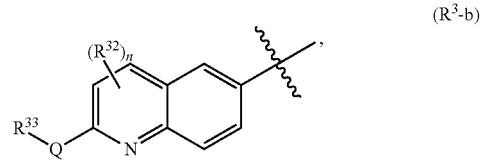

($R^3$-b)

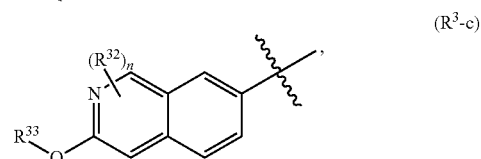

($R^3$-c)

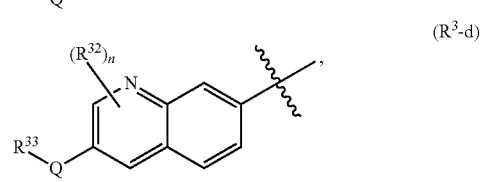

($R^3$-d)

-continued

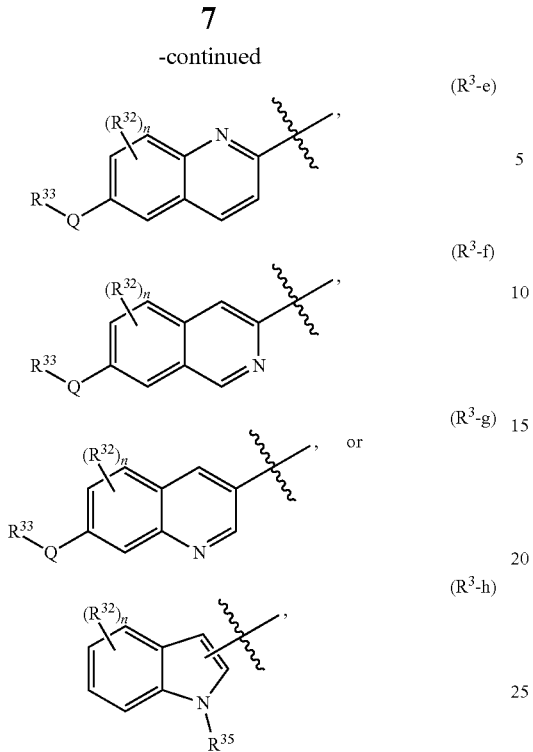

wherein
n is 0, 1, or 2;
Q is —O—, —S—, or —N(R$^Q$)—, wherein R$^Q$ is hydrogen or C$_{1-6}$ alkyl; and
R$^{33}$ is C$_{1-6}$ alkyl, C$_{2-6}$ alkenyl, C$_{1-6}$ haloalkyl, C$_{3-8}$ cycloalkyl, (C$_{3-8}$ cycloalkyl)C$_{1-6}$ alkyl, heterocyclyl, (heterocyclyl)C$_{1-6}$ alkyl, aryl, arylC$_{1-6}$ alkyl, heteroaryl, or heteroarylC$_{1-6}$ alkyl wherein the alkyl, cycloalkyl, heterocyclyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or —N(R$^{20}$)C(O)N(R$^{20}$)$_2$, wherein each R$^{20}$ is independently hydrogen or C$_{1-6}$ alkyl,
each R$^{32}$ is independently halogen, cyano, nitro, C$_{1-6}$ alkyl, C$_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each R$^{34}$ is independently hydrogen or C$_{1-6}$ alkyl;
and
R$^{35}$ is hydrogen or C$_{1-6}$ alkyl; and
each R is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, C$_{1-6}$ alkyl, C$_{1-6}$ haloalkyl, —OR$^o$, —SR$^o$, —N(R$^o$)$_2$, —C(O)R$^o$, —C(O)OR$^o$, —C(O)N(R$^o$)$_2$, —S(O)$_2$R$^o$, —OC(O)R$^o$, —OC(O)OR$^o$, —OC(O)N(R$^o$)$_2$, —N(R$^o$)C(O)R, —N(R$^o$)C(O)OR$^o$, or —N(R$^o$)C(O)N(R$^o$)$_2$, wherein each R$^o$ is independently hydrogen or C$_{1-6}$ alkyl.

The disclosure further comprises subgenera of formula (I) in which the substituents are selected as any and all combinations of one or more of structural formula (I), n, Q, R$^1$, R$^3$, R$^{32}$, and R$^{33}$ as defined herein, including without limitation, the following:

Structural Formula I is one of formulae (Ia)-(Ib):

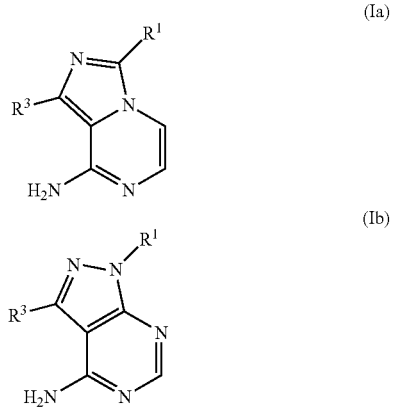

R$^1$ is selected from one of the following groups (1a)-(1ii):
(1a) R$^1$ is C$_{2-4}$ alkyl, —C$_{1-4}$ alkyl-R$^{12}$, C$_{2-4}$ alkynyl, C$_{3-8}$ cycloalkyl, monocyclic heterocyclyl, monocyclic heteroaryl, or phenyl, wherein the alkyl, cycloalkyl, heterocyclyl, heteroaryl, and phenyl groups are each optionally substituted with one or two R$^{11}$ groups.
(1b) R$^1$ is C$_{3-8}$ cycloalkyl, monocyclic heterocyclyl, monocyclic heteroaryl, or phenyl, wherein the cycloalkyl, heterocyclyl, heteroaryl, and phenyl groups are each optionally substituted with one or two R$^{11}$ groups.
(1c) R$^1$ is C$_{3-8}$ cycloalkyl; or a monocyclic heterocyclyl optionally substituted with one R$^1$ group.
(1d) R$^1$ is C$_{3-8}$ cycloalkyl.
(1e) R$^1$ is monocyclic heterocyclyl optionally substituted with one R$^{11}$ group.
(1f) R$^1$ is piperidinyl or tetrahydropyranyl, each optionally substituted with one R$^{11}$ group.
(1g) R$^1$ is phenyl optionally substituted with one or two R$^{11}$ groups.
(1h) R$^1$ is C$_{2-6}$ alkyl, optionally substituted with —OR.
(1i) R$^1$ is C$_{2-4}$ alkyl.
(1j) R$^1$ is isopropyl or t-butyl.
(1k) R$^1$ is t-butyl.
(1l) R$^1$ is isopropyl.
(1m) R$^1$ is C$_{2-6}$ alkyl or —C$_{1-4}$ alkyl-R$^{12}$.
(1n) R$^1$ is —C$_{1-4}$ alkyl-R$^{12}$.
(1o) R$^1$ is —C$_{1-2}$ alkyl-R$^{12}$.
(1p) R$^1$ is —CH$_2$—R$^{12}$.
(1q) Any one of groups (1m)-(1p), wherein R$^{12}$ is —OR, —C(O)OR, —C(O)NR$_2$, phenyl, monocyclic heteroaryl, C$_{3-8}$ cycloalkyl, or monocyclic heterocyclyl, wherein the phenyl, heteroaryl, C$_{3-8}$ cycloalkyl, and heterocyclyl groups are each optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.
(1r) Any one of groups (1m)-(1p), R$^{12}$ is —OR, —C(O)OR or —C(O)NR$_2$.
(1s) Any one of groups (1m)-(1p), R$^{12}$ is phenyl, monocyclic heteroaryl, C$_{3-8}$ cycloalkyl, or monocyclic heterocyclyl, each optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1t) Any one of groups (1m)-(1p), wherein R$^{12}$ is phenyl, monocyclic heteroaryl, C$_{3-8}$ cycloalkyl, or monocyclic heterocyclyl, wherein the phenyl, heteroaryl, C$_{3-8}$ cycloalkyl, and heterocyclyl groups are each optionally substituted by one or two groups that are each independently halogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1u) Any one of groups (1m)-(1p), R$^{12}$ is phenyl or monocyclic heterocyclyl, each optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1v) Any one of groups (1m)-(1p), R$^{12}$ is monocyclic heterocyclyl optionally substituted by one, two, or three groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1w) Any one of groups (1m)-(1p), wherein R$^{12}$ is monocyclic heterocyclyl optionally substituted by one or two groups that are each independently halogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1x) Any one of groups (1m)-(1p), R$^{12}$ is piperidinyl or tetrahydropyranyl, each optionally substituted by one or two groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1y) Any one of groups (1m)-(1p), wherein R$^{12}$ is piperidinyl optionally substituted by one or two groups that are each independently halogen, cyano, nitro, C$_{1-6}$ alkyl, C$_{1-6}$ haloalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1z) Any one of groups (1m)-(1p), wherein R$^{12}$ is piperidinyl optionally substituted by one or two groups that are each independently C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl.

(1aa) Any one of groups (1m)-(1p), wherein R$^{12}$ is piperidinyl optionally substituted by one or two groups that are each independently C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1bb) Any one of groups (1m)-(1p), wherein R$^{12}$ is piperidinyl optionally substituted by one or two groups that are each independently C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or C$_{1-6}$ alkyl.

(1cc) Any one of groups (1m)-(1p), wherein R$^{12}$ is piperidinyl optionally substituted by one or two groups that are each independently C$_{1-6}$ alkyl, —C(O)R, —C(O)OR, —C(O)NR$_2$, or —S(O)$_2$R.

(1dd) Any one of groups (1m)-(1p), wherein R$^{12}$ is piperidinyl optionally substituted by one or two groups that are each independently C$_{1-6}$ alkyl, —C(O)R$^A$, or —S(O)$_2$R$^A$, wherein each R$^A$ is independently hydrogen or C$_{1-6}$ alkyl.

(1ee) Any one of groups (1m)-(1p), wherein R$^{12}$ is

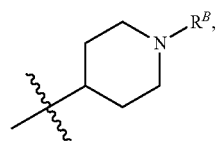

wherein R$^B$ is hydrogen, C$_{1-6}$ alkyl, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$.

(1ff) Any one of groups (1m)-(1p), wherein R$^{12}$ is

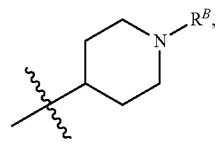

wherein R$^B$ is hydrogen, C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen, C$_{1-6}$ alkyl, C$_{2-6}$ alkenyl, C$_{1-6}$ haloalkyl, C$_{3-8}$ cycloalkyl, heterocyclyl, aryl, arylC$_{1-6}$ alkyl, heteroaryl, or heteroarylC$_{1-6}$ alkyl.

(1gg) Any one of groups (1m)-(1p), wherein R$^{12}$ is

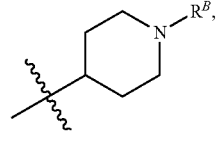

wherein R$^B$ is hydrogen, C$_{1-6}$ alkyl, —C(O)R$^A$, —C(O)OR$^A$, —C(O)N(R$^A$)$_2$, —S(O)$_2$R$^A$, —OC(O)R$^A$, —OC(O)OR$^A$, —OC(O)N(R$^A$)$_2$, —N(R$^A$)C(O)R$^A$, —N(R$^A$)C(O)OR$^A$, or —N(R$^A$)C(O)N(R$^A$)$_2$, wherein each R$^A$ is independently hydrogen or C$_{1-6}$ alkyl.

(1hh) Any one of groups (1m)-(1p), wherein R$^{12}$ is

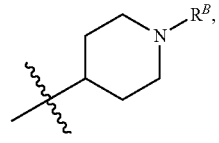

wherein $R^B$ is hydrogen, $C_{1-6}$ alkyl, —C(O)R, —C(O)OR, —C(O)NR_2, or —S(O)_2R.

(1ii) Any one of groups (1m)-(1p), wherein $R^{12}$ is

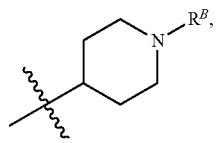

wherein $R^B$ is hydrogen, $C_{1-6}$ alkyl, —C(O)$R^A$, or —S(O)$_2R^A$, wherein each $R^A$ is independently hydrogen or $C_{1-6}$ alkyl.

$R^3$ is selected from one of the following groups (2a)-(2aa):

(2a) $R^3$ is one of groups ($R^3$-a) through ($R^3$-g) as defined above.

(2b) $R^3$ is one of groups ($R^3$-b) through ($R^3$-g) as defined above.

(2c) $R^3$ is

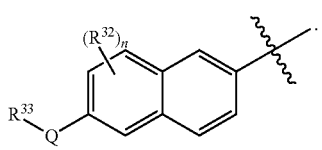

(2d) $R^3$ is

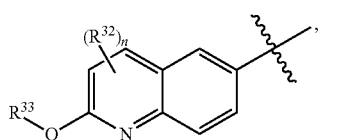

,

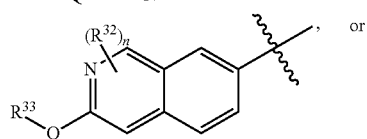

, or

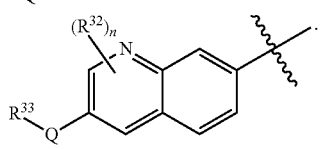

(2e) $R^3$ is

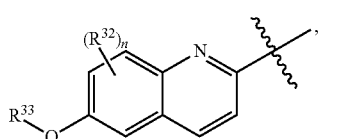

,

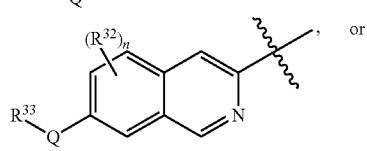

, or

-continued

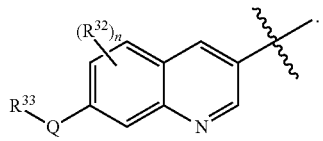

(2f) $R^3$ is

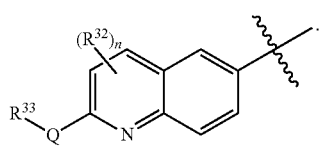

(2g) $R^3$ is

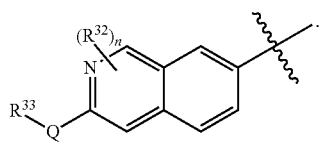

(2h) $R^3$ is

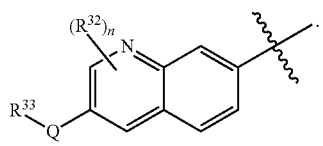

(2i) $R^3$ is

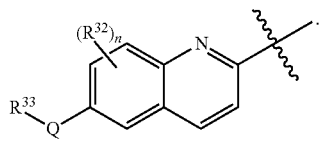

(2j) $R^3$ is

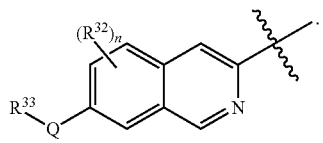

(2k) $R^3$ is

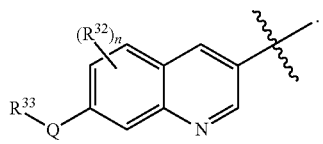

(2l) R³ is

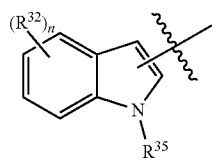

(2m) R³ is

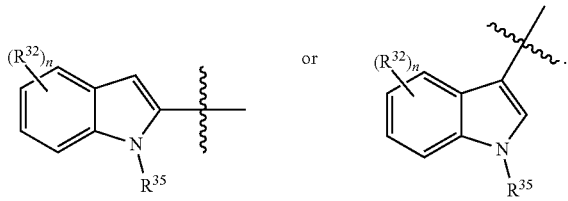  or (2n) R³ is

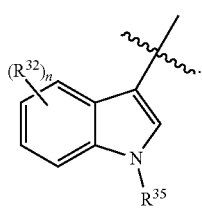

(2o) R³ is

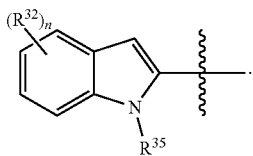

(2p) R³ is

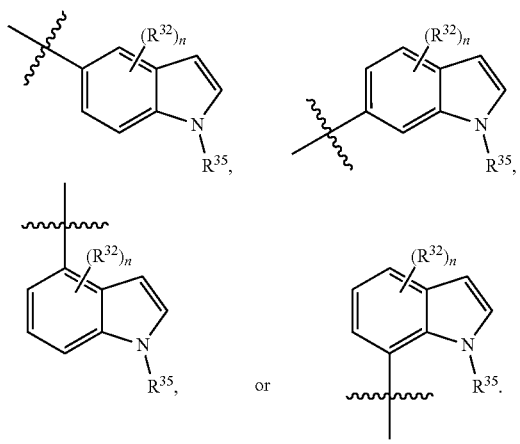

(2q) R³ is

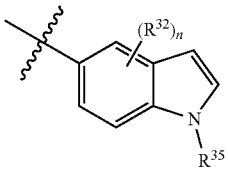 or 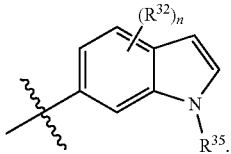.

(2r) R³

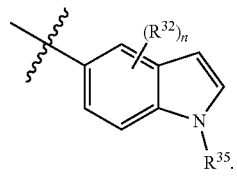

(2s) R³ is

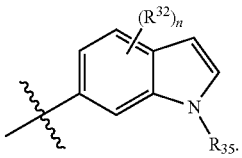

(2t) R³ is

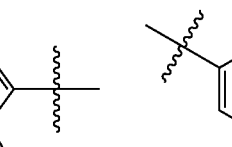 or 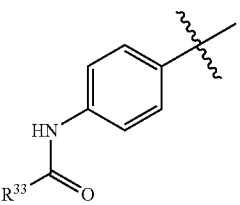.

(2u) Any one of groups (2l)-(2t), wherein R³⁵ is hydrogen or methyl.
(2v) Any one of groups (2l)-(2t), wherein R³⁵ is methyl.
(2w) Any one of groups (2l)-(2t), wherein R³⁵ is hydrogen.
(2x) R³ is (2y) Group (2x) wherein R³³ is $C_{1-6}$ alkyl, $C_{2-6}$ alkenyl, $C_{1-6}$ haloalkyl, $C_{3-8}$ cycloalkyl, aryl, or aryl$C_{1-6}$ alkyl.
(2z) Group (2x) wherein R³³ is $C_{1-6}$ alkyl, $C_{1-6}$ haloalkyl, $C_{3-8}$ cycloalkyl, phenyl, or benzyl.
(2aa) Group (2x) wherein R³³ is $C_{1-4}$ alkyl, $C_{1-4}$ haloalkyl, $C_{5-6}$ cycloalkyl, phenyl, or benzyl.

15

Q is selected from one of the following groups (3a)-(3e):
(3a) Q is —O— or —N($R^Q$)—.
(3b) Q is —O— or —N(H)—.
(3c) Q is —O—.
(3d) Q is —N($R^Q$)—.
(3e) Q is —N(H)—.

n and $R^{32}$ are selected from one of the following groups (4a)-(4x):
(4a) n is 0.
(4b) n is 0 or 1 and $R^{32}$ is as defined for formula (I).
(4c) n is 0 or 1 and $R^{32}$ is halogen, cyano, nitro, $C_{1-6}$ alkyl, or $C_{1-6}$ haloalkyl.
(4d) n is 0 or 1 and $R^{32}$ is halogen, $C_{1-6}$ alkyl, or $C_{1-6}$ haloalkyl.
(4e) n is 0 or 1 and each $R^{32}$ is —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4f) n is 0 or 1 and $R^{32}$ is —$OR^{34}$, —$SR^{34}$, —$N(R^{34})_2$, wherein each $R^{34}$ is independently hydrogen or $C_{1-6}$ alkyl.
(4g) n is 0 or 1 and $R^{32}$ is —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4h) n is as defined for formula (I) and each $R^{32}$ is independently halogen, cyano, nitro, $C_{1-6}$ alkyl, or $C_{1-6}$ haloalkyl.
(4i) n is as defined for formula (I) and each $R^{32}$ is independently halogen, $C_{1-6}$ alkyl, or $C_{1-6}$ haloalkyl.
(4j) n is as defined for formula (I) and each $R^{32}$ is independently —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4k) n is as defined for formula (I) and each $R^{32}$ is independently —$OR^{34}$, —$SR^{34}$, —$N(R^{34})_2$, wherein each $R^{34}$ is independently hydrogen or $C_{1-6}$ alkyl.
(4l) n is as defined for formula (I) and each $R^{32}$ is independently —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4m) n is 1 or 2 and each $R^{32}$ is as defined for formula (I).
(4n) n is 1 or 2 and each $R^{32}$ is independently halogen, cyano, nitro, $C_{1-6}$ alkyl, or $C_{1-6}$ haloalkyl.
(4o) n is 1 or 2 and each $R^{32}$ is independently halogen, $C_{1-6}$ alkyl, or $C_{1-6}$ haloalkyl.
(4p) n is 1 or 2 and each $R^{32}$ is independently —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4q) n is 1 or 2 and each $R^{32}$ is independently —$OR^{34}$, —$SR^{34}$, —$N(R^{34})_2$, wherein each $R^{34}$ is independently hydrogen or $C_{1-6}$ alkyl.
(4r) n is 1 or 2 and each $R^{32}$ is independently —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.
(4s) n is 1 and $R^{32}$ is as defined for formula (I).
(4t) n is 1 and $R^{32}$ is halogen, cyano, nitro, $C_{1-6}$ alkyl, or $C_{1-6}$ haloalkyl.
(4u) n is 1 and $R^{32}$ is halogen, $C_{1-6}$ alkyl, or $C_{1-6}$ haloalkyl.

16

(4v) n is 1 and $R^{32}$ is —$OR^{34}$, —$SR^{34}$, —$N(R^{34})_2$, —$C(O)R^{34}$, —$C(O)OR^{34}$, —$C(O)N(R^{34})_2$, —$S(O)_2R^{34}$, —$OC(O)R^{34}$, —$OC(O)OR^{34}$, —$OC(O)N(R^{34})_2$, —$N(R^{34})C(O)R^{34}$, —$N(R^{34})C(O)OR^{34}$, or —$N(R^{34})C(O)N(R^{34})_2$, wherein each $R^{34}$ is independently hydrogen or $C_{1-6}$ alkyl.
(4w) n is 1 and $R^{32}$ is —$OR^{34}$, —$SR^{34}$, —$N(R^{34})_2$, wherein each $R^{34}$ is independently hydrogen or $C_{1-6}$ alkyl.
(4x) n is 1 and $R^{32}$ is —$C(O)R^{34}$, —$C(O)OR^{34}$, —$C(O)N(R^{34})_2$, or —$S(O)_2R^{34}$, wherein each $R^{34}$ is independently hydrogen or $C_{1-6}$ alkyl.

$R^{33}$ is selected from one of the following groups (5a)-(5t):
(5a) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5b) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5c) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.
(5d) $R^{33}$ is $C_{1-6}$ alkyl, $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.
(5e) $R^{33}$ is $C_{2-6}$ alkenyl, aryl$C_{1-6}$ alkyl, or heteroaryl$C_{1-6}$ alkyl, wherein the arylalkyl and heteroarylalkyl are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5f) $R^{33}$ is $C_{2-6}$ alkenyl, aryl$C_{1-6}$ alkyl, or heteroaryl$C_{1-6}$ alkyl, wherein the arylalkyl and heteroarylalkyl are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.
(5g) $R^{33}$ is $C_{2-6}$ alkenyl, aryl$C_{1-6}$ alkyl, or heteroaryl$C_{1-6}$ alkyl, wherein the arylalkyl and heteroarylalkyl are optionally substituted with one or two groups that are each independently halogen, $C_{1-6}$ alkyl, or $C_{1-6}$ haloalkyl.

(5h) $R^{33}$ is $C_{2-6}$ alkenyl, aryl$C_{1-6}$ alkyl, or heteroaryl$C_{1-6}$ alkyl, wherein the arylalkyl and heteroarylalkyl are each substituted with one or two groups that are each independently halogen, $C_{1-6}$ alkyl, or $C_{1-6}$ haloalkyl.

(5i) $R^{33}$ is aryl$C_{1-6}$ alkyl or heteroaryl$C_{1-6}$ alkyl, each are optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5j) $R^{33}$ is aryl$C_{1-6}$ alkyl or heteroaryl$C_{1-6}$ alkyl, each are each substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5k) $R^{33}$ is aryl$C_{1-6}$ alkyl or heteroaryl$C_{1-6}$ alkyl, each optionally substituted with one or two groups that are each independently halogen, $C_{1-6}$ alkyl, or $C_{1-6}$ haloalkyl.

(5l) $R^{33}$ is aryl$C_{1-6}$ alkyl or heteroaryl$C_{1-6}$ alkyl, each substituted with one or two groups that are each independently halogen, $C_{1-6}$ alkyl, or $C_{1-6}$ haloalkyl.

(5m) $R^{33}$ is aryl$C_{1-6}$ alkyl optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5n) $R^{33}$ is aryl$C_{1-6}$ alkyl substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5o) $R^{33}$ is aryl$C_{1-6}$ alkyl optionally substituted with one or two groups that are each independently halogen, $C_{1-6}$ alkyl, or $C_{1-6}$ haloalkyl.

(5p) $R^{33}$ is aryl$C_{1-6}$ alkyl substituted with one or two groups that are each independently halogen, $C_{1-6}$ alkyl, or $C_{1-6}$ haloalkyl.

(5q) $R^{33}$ is benzyl optionally substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5r) $R^{33}$ is benzyl substituted with one, two, three, or four groups that are each independently halogen, cyano, nitro, $C_{1-6}$ alkyl, $C_{1-6}$ haloalkyl, —$OR^{20}$, —$SR^{20}$, —$N(R^{20})_2$, —$C(O)R^{20}$, —$C(O)OR^{20}$, —$C(O)N(R^{20})_2$, —$S(O)_2R^{20}$, —$OC(O)R^{20}$, —$OC(O)OR^{20}$, —$OC(O)N(R^{20})_2$, —$N(R^{20})C(O)R^{20}$, —$N(R^{20})C(O)OR^{20}$, or —$N(R^{20})C(O)N(R^{20})_2$, wherein each $R^{20}$ is independently hydrogen or $C_{1-6}$ alkyl.

(5s) $R^{33}$ is benzyl optionally substituted with one or two groups that are each independently halogen, $C_{1-6}$ alkyl, or $C_{1-6}$ haloalkyl.

(5t) $R^{33}$ is benzyl substituted with one or two groups that are each independently halogen, $C_{1-6}$ alkyl, or $C_{1-6}$ haloalkyl.

Particular embodiments of this aspect of the invention include compounds of any one of the formulae (I), (Ia), and (Ib), each as defined in each of the following rows, wherein each entry is a group number as defined above (e.g., (3c) refers to Q is —O—), a dash "-" indicates that the variable is as defined for formula (I) or defined according to any one of the applicable variable definitions (1a)-(5t) [e.g., when $R^1$ is a dash, it can be either as defined for Formula (I) or any one of definitions (1a)-(1ii)]; and an "x" indicates that the variable is not applicable to the particular embodiment (e.g., when $R^3$ is (2o), then Q and $R^{33}$ are not necessary):

| | $R^1$ | $R^3$ | $R^{33}$ | n & $R^{32}$ | Q |
|---|---|---|---|---|---|
| (1)-1 | 1h | 2b | 5a | 4c | 3a |
| (1)-2 | 1n | 2b | 5a | 4c | 3a |
| (1)-3 | 1p | 2b | 5a | 4c | 3a |
| (1)-4 | 1aa | 2b | 5a | 4c | 3a |
| (1)-5 | 1h | 2b | 5e | 4c | 3a |
| (1)-6 | 1n | 2b | 5e | 4c | 3a |
| (1)-7 | 1p | 2b | 5e | 4c | 3a |
| (1)-8 | 1aa | 2b | 5e | 4c | 3a |
| (1)-9 | 1h | 2b | 5i | 4c | 3a |
| (1)-10 | 1n | 2b | 5i | 4c | 3a |
| (1)-11 | 1p | 2b | 5i | 4c | 3a |
| (1)-12 | 1aa | 2b | 5i | 4c | 3a |
| (1)-13 | 1h | 2b | 5q | 4c | 3a |
| (1)-14 | 1n | 2b | 5q | 4c | 3a |
| (1)-15 | 1p | 2b | 5q | 4c | 3a |
| (1)-16 | 1aa | 2b | 5q | 4c | 3a |
| (1)-17 | 1h | 2c | 5a | 4c | 3a |
| (1)-18 | 1n | 2c | 5a | 4c | 3a |
| (1)-19 | 1p | 2c | 5a | 4c | 3a |
| (1)-20 | 1aa | 2c | 5a | 4c | 3a |
| (1)-21 | 1h | 2c | 5e | 4c | 3a |
| (1)-22 | 1n | 2c | 5e | 4c | 3a |
| (1)-23 | 1p | 2c | 5e | 4c | 3a |
| (1)-24 | 1aa | 2c | 5e | 4c | 3a |
| (1)-25 | 1h | 2c | 5i | 4c | 3a |
| (1)-26 | 1n | 2c | 5i | 4c | 3a |
| (1)-27 | 1p | 2c | 5i | 4c | 3a |
| (1)-28 | 1aa | 2c | 5i | 4c | 3a |
| (1)-29 | 1h | 2c | 5q | 4c | 3a |
| (1)-30 | 1n | 2c | 5q | 4c | 3a |
| (1)-31 | 1p | 2c | 5q | 4c | 3a |
| (1)-32 | 1aa | 2c | 5q | 4c | 3a |
| (1)-33 | 1h | 2b | 5a | 4n | 3a |
| (1)-34 | 1n | 2b | 5a | 4n | 3a |
| (1)-35 | 1p | 2b | 5a | 4n | 3a |
| (1)-36 | 1aa | 2b | 5a | 4n | 3a |
| (1)-37 | 1h | 2b | 5e | 4n | 3a |
| (1)-38 | 1n | 2b | 5e | 4n | 3a |
| (1)-39 | 1p | 2b | 5e | 4n | 3a |
| (1)-40 | 1aa | 2b | 5e | 4n | 3a |
| (1)-41 | 1h | 2b | 5i | 4n | 3a |
| (1)-42 | 1n | 2b | 5i | 4n | 3a |
| (1)-43 | 1p | 2b | 5i | 4n | 3a |
| (1)-44 | 1aa | 2b | 5i | 4n | 3a |
| (1)-45 | 1h | 2b | 5q | 4n | 3a |
| (1)-46 | 1n | 2b | 5q | 4n | 3a |
| (1)-47 | 1p | 2b | 5q | 4n | 3a |
| (1)-48 | 1aa | 2b | 5q | 4n | 3a |
| (1)-49 | 1h | 2c | 5a | 4n | 3a |
| (1)-50 | 1n | 2c | 5a | 4n | 3a |

-continued

| | R¹ | R³ | R³³ | n & R³² | Q |
|---|---|---|---|---|---|
| (1)-51 | 1p | 2c | 5a | 4n | 3a |
| (1)-52 | 1aa | 2c | 5a | 4n | 3a |
| (1)-53 | 1h | 2c | 5e | 4n | 3a |
| (1)-54 | 1n | 2c | 5e | 4n | 3a |
| (1)-55 | 1p | 2c | 5e | 4n | 3a |
| (1)-56 | 1aa | 2c | 5e | 4n | 3a |
| (1)-57 | 1h | 2c | 5i | 4n | 3a |
| (1)-58 | 1n | 2c | 5i | 4n | 3a |
| (1)-59 | 1p | 2c | 5i | 4n | 3a |
| (1)-60 | 1aa | 2c | 5i | 4n | 3a |
| (1)-61 | 1h | 2c | 5q | 4n | 3a |
| (1)-62 | 1n | 2c | 5q | 4n | 3a |
| (1)-63 | 1p | 2c | 5q | 4n | 3a |
| (1)-64 | 1aa | 2c | 5q | 4n | 3a |
| (1)-65 | 1h | 2b | 5a | 4c | 3c |
| (1)-66 | 1n | 2b | 5a | 4c | 3c |
| (1)-67 | 1p | 2b | 5a | 4c | 3c |
| (1)-68 | 1aa | 2b | 5a | 4c | 3c |
| (1)-69 | 1h | 2b | 5e | 4c | 3c |
| (1)-70 | 1n | 2b | 5e | 4c | 3c |
| (1)-71 | 1p | 2b | 5e | 4c | 3c |
| (1)-72 | 1aa | 2b | 5e | 4c | 3c |
| (1)-73 | 1h | 2b | 5i | 4c | 3c |
| (1)-74 | 1n | 2b | 5i | 4c | 3c |
| (1)-75 | 1p | 2b | 5i | 4c | 3c |
| (1)-76 | 1aa | 2b | 5i | 4c | 3c |
| (1)-77 | 1h | 2b | 5q | 4c | 3c |
| (1)-78 | 1n | 2b | 5q | 4c | 3c |
| (1)-79 | 1p | 2b | 5q | 4c | 3c |
| (1)-80 | 1aa | 2b | 5q | 4c | 3c |
| (1)-81 | 1h | 2c | 5a | 4c | 3c |
| (1)-82 | 1n | 2c | 5a | 4c | 3c |
| (1)-83 | 1p | 2c | 5a | 4c | 3c |
| (1)-84 | 1aa | 2c | 5a | 4c | 3c |
| (1)-85 | 1h | 2c | 5e | 4c | 3c |
| (1)-86 | 1n | 2c | 5e | 4c | 3c |
| (1)-87 | 1p | 2c | 5e | 4c | 3c |
| (1)-88 | 1aa | 2c | 5e | 4c | 3c |
| (1)-89 | 1h | 2c | 5i | 4c | 3c |
| (1)-90 | 1n | 2c | 5i | 4c | 3c |
| (1)-91 | 1p | 2c | 5i | 4c | 3c |
| (1)-92 | 1aa | 2c | 5i | 4c | 3c |
| (1)-93 | 1h | 2c | 5q | 4c | 3c |
| (1)-94 | 1n | 2c | 5q | 4c | 3c |
| (1)-95 | 1p | 2c | 5q | 4c | 3c |
| (1)-96 | 1aa | 2c | 5q | 4c | 3c |
| (1)-97 | 1h | 2b | 5a | 4n | 3c |
| (1)-98 | 1n | 2b | 5a | 4n | 3c |
| (1)-99 | 1p | 2b | 5a | 4n | 3c |
| (1)-100 | 1aa | 2b | 5a | 4n | 3c |
| (1)-101 | 1h | 2b | 5e | 4n | 3c |
| (1)-102 | 1n | 2b | 5e | 4n | 3c |
| (1)-103 | 1p | 2b | 5e | 4n | 3c |
| (1)-104 | 1aa | 2b | 5e | 4n | 3c |
| (1)-105 | 1h | 2b | 5i | 4n | 3c |
| (1)-106 | 1n | 2b | 5i | 4n | 3c |
| (1)-107 | 1p | 2b | 5i | 4n | 3c |
| (1)-108 | 1aa | 2b | 5i | 4n | 3c |
| (1)-109 | 1h | 2b | 5q | 4n | 3c |
| (1)-110 | 1n | 2b | 5q | 4n | 3c |
| (1)-111 | 1p | 2b | 5q | 4n | 3c |
| (1)-112 | 1aa | 2b | 5q | 4n | 3c |
| (1)-113 | 1h | 2c | 5a | 4n | 3c |
| (1)-114 | 1n | 2c | 5a | 4n | 3c |
| (1)-115 | 1p | 2c | 5a | 4n | 3c |
| (1)-116 | 1aa | 2c | 5a | 4n | 3c |
| (1)-117 | 1h | 2c | 5e | 4n | 3c |
| (1)-118 | 1n | 2c | 5e | 4n | 3c |
| (1)-119 | 1p | 2c | 5e | 4n | 3c |
| (1)-120 | 1aa | 2c | 5e | 4n | 3c |
| (1)-121 | 1h | 2c | 5i | 4n | 3c |
| (1)-122 | 1n | 2c | 5i | 4n | 3c |
| (1)-123 | 1p | 2c | 5i | 4n | 3c |
| (1)-124 | 1aa | 2c | 5i | 4n | 3c |
| (1)-125 | 1h | 2c | 5q | 4n | 3c |
| (1)-126 | 1n | 2c | 5q | 4n | 3c |
| (1)-127 | 1p | 2c | 5q | 4n | 3c |
| (1)-128 | 1aa | 2c | 5q | 4n | 3c |
| (1)-129 | 1h | 2b | — | — | — |
| (1)-130 | 1n | 2b | — | — | — |
| (1)-131 | 1p | 2b | — | — | — |
| (1)-132 | 1aa | 2b | — | — | — |
| (1)-133 | 1h | 2c | — | — | — |
| (1)-134 | 1n | 2c | — | — | — |
| (1)-135 | 1p | 2c | — | — | — |
| (1)-136 | 1aa | 2c | — | — | — |
| (1)-137 | 1h | 2b | — | — | 3c |
| (1)-138 | 1n | 2b | — | — | 3c |
| (1)-139 | 1p | 2b | — | — | 3c |
| (1)-140 | 1aa | 2b | — | — | 3c |
| (1)-141 | 1h | 2c | — | — | 3c |
| (1)-142 | 1n | 2c | — | — | 3c |
| (1)-143 | 1p | 2c | — | — | 3c |
| (1)-144 | 1aa | 2c | — | — | 3c |
| (1)-145 | 1h | 2b | — | — | 3a |
| (1)-146 | 1n | 2b | — | — | 3a |
| (1)-147 | 1p | 2b | — | — | 3a |
| (1)-148 | 1aa | 2b | — | — | 3a |
| (1)-149 | 1h | 2c | — | — | 3a |
| (1)-150 | 1n | 2c | — | — | 3a |
| (1)-151 | 1p | 2c | — | — | 3a |
| (1)-152 | 1aa | 2c | — | — | 3a |
| (1)-153 | — | — | 5a | — | 3a |
| (1)-154 | — | — | 5e | — | 3a |
| (1)-155 | — | — | 5i | — | 3a |
| (1)-156 | — | — | 5q | — | 3a |
| (1)-157 | — | — | 5a | — | 3c |
| (1)-158 | — | — | 5e | — | 3a |
| (1)-159 | — | — | 5i | — | 3a |
| (1)-160 | — | — | 5q | — | 3a |
| (1)-161 | — | 2b | 5a | — | 3a |
| (1)-162 | — | 2b | 5e | — | 3a |
| (1)-163 | — | 2b | 5i | — | 3a |
| (1)-164 | — | 2b | 5q | — | 3a |
| (1)-165 | — | 2b | 5a | — | 3c |
| (1)-166 | — | 2b | 5e | — | 3a |
| (1)-167 | — | 2b | 5i | — | 3a |
| (1)-168 | — | 2b | 5q | — | 3a |
| (1)-169 | — | 2c | 5a | — | 3a |
| (1)-170 | — | 2c | 5e | — | 3a |
| (1)-171 | — | 2c | 5i | — | 3a |
| (1)-172 | — | 2c | 5q | — | 3a |
| (1)-173 | — | 2c | 5a | — | 3c |
| (1)-174 | — | 2c | 5e | — | 3a |
| (1)-175 | — | 2c | 5i | — | 3a |
| (1)-176 | — | 2c | 5q | — | 3a |
| (1)-177 | 1h | 2o | x | 4c | x |
| (1)-178 | 1n | 2o | x | 4c | x |
| (1)-179 | 1p | 2o | x | 4c | x |
| (1)-180 | 1aa | 2o | x | 4c | x |
| (1)-181 | 1h | 2r | x | 4c | x |
| (1)-182 | 1n | 2r | x | 4c | x |
| (1)-183 | 1p | 2r | x | 4c | x |
| (1)-184 | 1aa | 2r | x | 4c | x |
| (1)-185 | 1h | 2o | x | 4n | x |
| (1)-186 | 1n | 2o | x | 4n | x |
| (1)-187 | 1p | 2o | x | 4n | x |
| (1)-188 | 1aa | 2o | x | 4n | x |
| (1)-189 | 1h | 2r | x | 4n | x |
| (1)-190 | 1n | 2r | x | 4n | x |
| (1)-191 | 1p | 2r | x | 4n | x |
| (1)-192 | 1aa | 2r | x | 4n | x |
| (1)-193 | 1h | 2o | x | — | x |
| (1)-194 | 1n | 2o | x | — | x |
| (1)-195 | 1p | 2o | x | — | x |
| (1)-196 | 1aa | 2o | x | — | x |
| (1)-197 | 1h | 2r | x | — | x |
| (1)-198 | 1n | 2r | x | — | x |
| (1)-199 | 1p | 2r | x | — | x |
| (1)-200 | 1aa | 2r | x | — | x |

In some embodiments of the disclosure, the BKI is:

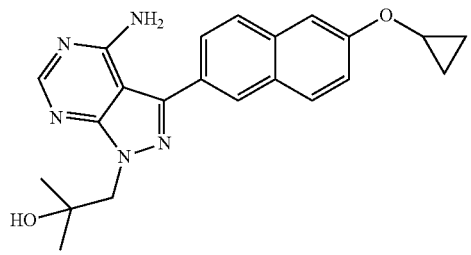 [SMILES: CC(C)(O)Cn1nc(-c2ccc3cc(OC4CC4)ccc3c2)c2c(N)ncnc21]

1-(4-amino-3-(6-cyclopropoxynaphthalen-2-yl)-1H-pyrazolo[3,4-d]pyrimidin-1-yl)-2-methylpropan-2-ol;

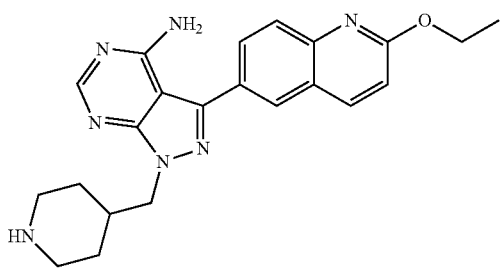 [SMILES: CCOc1ccc2cc(-c3nn(CC4CCNCC4)c4ncnc(N)c34)ccc2n1]

3-(2-ethoxyquinolin-6-yl)-1-(piperidin-4-ylmethyl)-1H-pyrazolo[3,4-d]pyrimidin-4-amine;

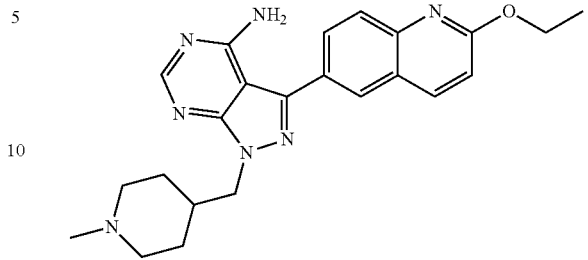

3-(2-ethoxyquinolin-6-yl)-1-((1-methylpiperidin-4-yl)methyl)-1H-pyrazolo[3,4-d]pyrimidin-4-amine; or

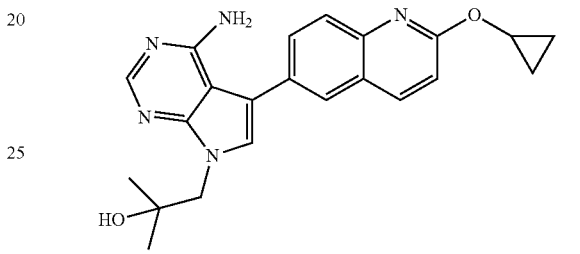

1-(4-amino-5-(2-cyclopropoxyquinolin-6-yl)-7H-pyrrolo[2,3-d]pyrimidin-7-yl)-2-methylpropan-2-ol.

Examples of BKIs suitable for use in the methods and compositions of the disclosure include, but are not limited to compounds listed in Table 1.

TABLE 1

| Bumped kinase inhibitor (BKI) compounds |
|---|
| 1-(6-ethoxynaphthalen-2-yl)-3-isopropylimidazo[1,5-a]pyrazin-8-amine |
| 3-(6-isopropoxynaphthalen-2-yl)-1-isopropyl-1H-pyrazolo[3,4-d]pyrimidin-4-amine |
| 1-isopropyl-3-(6-propoxynaphthalen-2-yl)-1H-pyrazolo[3,4-d]pyrimidin-4-amine |
| 1-isopropyl-3-(6-methoxynaphthalen-2-yl)-1H-pyrazolo[3,4-d]pyrimidin-4-amine |
| 3-(6-ethoxynaphthalen-2-yl)-1-isopropyl-1H-pyrazolo[3,4-d]pyrimidin-4-amine |
| 3-(1H-indol-2-yl)-1-isopropyl-1H-pyrazolo[3,4-d]pyrimidin-4-amine |
| 1-isopropyl-3-(4-methyl-1H-indol-2-yl)-1H-pyrazolo[3,4-d]pyrimidin-4-amine |
| 3-(4-chloro-1H-indol-2-yl)-1-isopropyl-1H-pyrazolo[3,4-d]pyrimidin-4-amine |
| 1-isopropyl-3-(5-methoxy-1H-indol-2-yl)-1H-pyrazolo[3,4-d]pyrimidin-4-amine |
| 3-(naphthalen-2-yl)-1-(piperidin-4-ylmethyl)-1H-pyrazolo[3,4-d]pyrimidin-4-amine |
| 3-(6-methoxynaphthalen-2-yl)-1-(piperidin-4-ylmethyl)-1H-pyrazolo[3,4-d]pyrimidin-4-amine |
| 3-(6-ethoxynaphthalen-2-yl)-1-(piperidin-4-ylmethyl)-1H-pyrazolo[3,4-d]pyrimidin-4-amine |
| 3-(6-ethoxynaphthalen-2-yl)-1-((1-methylpiperidin-4-yl)methyl)-1H-pyrazolo[3,4-d]pyrimidin-4-amine |
| 3-(6-isopropoxynaphthalen-2-yl)-1-(piperidin-4-ylmethyl)-1H-pyrazolo[3,4-d]pyrimidin-4-amine |
| 1-(piperidin-4-ylmethyl)-3-(6-propoxynaphthalen-2-yl)-1H-pyrazolo[3,4-d]pyrimidin-4-amine |
| 3-(6-(benzyloxy)naphthalen-2-yl)-1-(piperidin-4-ylmethyl)-1H-pyrazolo[3,4-d]pyrimidin-4-amine |
| 3-(6-butoxynaphthalen-2-yl)-1-(piperidin-4-ylmethyl)-1H-pyrazolo[3,4-d]pyrimidin-4-amine |
| 3-(6-(allyloxy)naphthalen-2-yl)-1-(piperidin-4-ylmethyl)-1H-pyrazolo[3,4-d]pyrimidin-4-amine |
| 3-(6-(2-chlorobenzyloxy)naphthalen-2-yl)-1-(piperidin-4-ylmethyl)-1H-pyrazolo[3,4-d]pyrimidin-4-amine |
| 3-(6-(3-chlorobenzyloxy)naphthalen-2-yl)-1-(piperidin-4-ylmethyl)-1H-pyrazolo[3,4-d]pyrimidin-4-amine |
| 3-(6-(4-chlorobenzyloxy)naphthalen-2-yl)-1-(piperidin-4-ylmethyl)-1H-pyrazolo[3,4-d]pyrimidin-4-amine |
| 3-(6-(benzyloxy)naphthalen-2-yl)-1-isopropyl-1H-pyrazolo[3,4-d]pyrimidin-4-amine |
| 3-(6-(allyloxy)naphthalen-2-yl)-1-isopropyl-1H-pyrazolo[3,4-d]pyrimidin-4-amine |
| 3-(6-butoxynaphthalen-2-yl)-1-isopropyl-1H-pyrazolo[3,4-d]pyrimidin-4-amine |
| 3-(6-isobutoxynaphthalen-2-yl)-1-isopropyl-1H-pyrazolo[3,4-d]pyrimidin-4-amine |

TABLE 1-continued

Bumped kinase inhibitor (BKI) compounds 3-(6-isobutoxynaphthalen-2-yl)-1-(piperidin-4-ylmethyl)-1H-pyrazolo[3,4-d]pyrimidin-4-amine
3-(6-(2-chlorobenzyloxy)naphthalen-2-yl)-1-isopropyl-1H-pyrazolo[3,4-d]pyrimidin-4-amine
3-(6-(3-chlorobenzyloxy)naphthalen-2-yl)-1-isopropyl-1H-pyrazolo[3,4-d]pyrimidin-4-amine
3-(6-(2,5-dimethylbenzyloxy)naphthalen-2-yl)-1-isopropyl-1H-pyrazolo[3,4-d]pyrimidin-4-amine
1-isopropyl-3-(6-(2-methylbenzyloxy)naphthalen-2-yl)-1H-pyrazolo[3,4-d]pyrimidin-4-amine
1-isopropyl-3-(6-(2-methyl-5-(trifluoromethyl)benzyloxy)naphthalen-2-yl)-1H-pyrazolo[3,4-d]pyrimidin-4-amine
3-(6-(3-chloro-4-(2,2,2-trifluoroethyl)benzyloxy)naphthalen-2-yl)-1-isopropyl-1H-pyrazolo[3,4-d]pyrimidin-4-amine
3-(6-(3-chloro-5-fluorobenzyloxy)naphthalen-2-yl)-1-isopropyl-1H-pyrazolo[3,4-d]pyrimidin-4-amine
1-isopropyl-3-(6-(1-phenylethoxy)naphthalen-2-yl)-1H-pyrazolo[3,4-d]pyrimidin-4-amine
3-(6-(4-tert-butylbenzyloxy)naphthalen-2-yl)-1-isopropyl-1H-pyrazolo[3,4-d]pyrimidin-4-amine
1-isopropyl-3-(6-(pyridin-4-ylmethoxy)naphthalen-2-yl)-1H-pyrazolo[3,4-d]pyrimidin-4-amine
3-(6-(4-chlorobenzyloxy)naphthalen-2-yl)-1-isopropyl-1H-pyrazolo[3,4-d]pyrimidin-4-amine
6-(4-amino-1-(piperidin-4-ylmethyl)-1H-pyrazolo[3,4-d]pyrimidin-3-yl)-N,N-dimethylquinolin-2-amine
3-tert-butyl-1-(6-ethoxynaphthalen-2-yl)imidazo[1,5-a]pyrazin-8-amine
3-tert-butyl-1-(6-methoxynaphthalen-2-yl)imidazo[1,5-a]pyrazin-8-amine
3-(2-methoxyquinolin-6-yl)-1-((tetrahydro-2H-pyran-4-yl)methyl)-1H-pyrazolo[3,4-d]pyrimidin-4-amine
3-(2-(cyclopropylmethoxy)quinolin-6-yl)-1-((tetrahydro-2H-pyran-4-yl)methyl)-1H-pyrazolo[3,4-d]pyrimidin-4-amine
3-(6-(cyclopropylmethoxy)naphthalen-2-yl)-1-((tetrahydro-2H-pyran-4-yl)methyl)-1H-pyrazolo[3,4-d]pyrimidin-4-amine
3-(6-cyclobutoxynaphthalen-2-yl)-1-((tetrahydro-2H-pyran-4-yl)methyl)-1H-pyrazolo[3,4-d]pyrimidin-4-amine
3-(6-(oxetan-3-yloxy)naphthalen-2-yl)-1-((tetrahydro-2H-pyran-4-yl)methyl)-1H-pyrazolo[3,4-d]pyrimidin-4-amine
3-(6-cyclopropoxynaphthalen-2-yl)-1-((tetrahydro-2H-pyran-4-yl)methyl)-1H-pyrazolo[3,4-d]pyrimidin-4-amine
3-(6-ethoxynaphthalen-2-yl)-1-isobutyl-1H-pyrazolo[3,4-d]pyrimidin-4-amine
1-(4-amino-3-(6-ethoxynaphthalen-2-yl)-1H-pyrazolo[3,4-d]pyrimidin-1-yl)-2-methylpropan-2-ol
3-(6-cyclopropoxynaphthalen-2-yl)-1-isobutyl-1H-pyrazolo[3,4-d]pyrimidin-4-amine
3-(4-amino-3-(6-ethoxynaphthalen-2-yl)-1H-pyrazolo[3,4-d]pyrimidin-1-yl)-2,2-dimethylpropan-1-ol
3-(4-amino-3-(6-cyclopropoxynaphthalen-2-yl)-1H-pyrazolo[3,4-d]pyrimidin-1-yl)-2,2-dimethylpropan-1-ol
1-(6-(4-amino-1-isobutyl-1H-pyrazolo[3,4-d]pyrimidin-3-yl)naphthalen-2-yloxy)-2-methylpropan-2-ol
2-(6-(4-amino-1-isobutyl-1H-pyrazolo[3,4-d]pyrimidin-3-yl)naphthalen-2-yloxy)ethanol
1-isobutyl-3-(6-(oxetan-3-yloxy)naphthalen-2-yl)-1H-pyrazolo[3,4-d]pyrimidin-4-amine
1-isobutyl-3-(6-(2-methoxyethoxy)naphthalen-2-yl)-1H-pyrazolo[3,4-d]pyrimidin-4-amine
3-(4-amino-3-(2-ethoxyquinolin-6-yl)-1H-pyrazolo[3,4-d]pyrimidin-1-yl)-2,2-dimethylpropan-1-ol
1-(4-amino-3-(2-ethoxyquinolin-6-yl)-1H-pyrazolo[3,4-d]pyrimidin-1-yl)-2-methylpropan-2-ol
3-(2-(2-methoxyethoxy)quinolin-6-yl)-1-neopentyl-1H-pyrazolo[3,4-d]pyrimidin-4-amine
3-(4-Amino-3-(2-cyclopropoxyquinolin-6-yl)-1H-pyrazolo[3,4-d]pyrimidin-1-yl)-2,2-dimethylpropan-1-ol
3-(2-cyclopropoxyquinolin-6-yl)-1-(piperidin-4-ylmethyl)-1H-pyrazolo[3,4-d]pyrimidin-4-amine
3-(2-cyclopropoxyquinolin-6-yl)-1-((1-methylpiperidin-4-yl)methyl)-1H-pyrazolo[3,4-d]pyrimidin-4-amine
1-(4-amino-3-(6-cyclopropoxynaphthalen-2-yl)-1H-pyrazolo[3,4-d]pyrimidin-1-yl)-2-methylpropan-2-ol
3-(2-cyclopropoxyquinolin-6-yl)-1-isobutyl-1H-pyrazolo[3,4-d]pyrimidin-4-amine
3-(2-cyclopropoxyquinolin-6-yl)-1-((tetrahydro-2H-pyran-4-yl)methyl)-1H-pyrazolo[3,4-d]pyrimidin-4-amine
1-(azetidin-3-ylmethyl)-3-(2-cyclopropoxyquinolin-6-yl)-1H-pyrazolo[3,4-d]pyrimidin-4-amine
3-(2-cyclopropoxyquinolin-6-yl)-1-((1-methylazetidin-3-yl)methyl)-1H-pyrazolo[3,4-d]pyrimidin-4-amine
3-(2-(2-methoxyethoxy)quinolin-6-yl)-1-((1-methylpiperidin-4-yl)methyl)-1H-pyrazolo[3,4-d]pyrimidin-4-amine
1-(4-Amino-3-(2-cyclopropoxyquinolin-6-yl)-1H-pyrazolo[3,4-d]pyrimidin-1-yl)-2-methylpropan-2-ol
1-isobutyl-3-(2-(2,2,2-trifluoroethoxy)quinolin-6-yl)-1H-pyrazolo[3,4-d]pyrimidin-4-amine
1-(piperidin-4-ylmethyl)-3-(2-(2,2,2-trifluoroethoxy)quinolin-6-yl)-1H-pyrazolo[3,4-d]pyrimidin-4-amine
1-((1-methylpiperidin-4-yl)methyl)-3-(2-(2,2,2-trifluoroethoxy)quinolin-6-yl)-1H-pyrazolo[3,4-d]pyrimidin-4-amine TABLE 1-continued Bumped kinase inhibitor (BKI) compounds 2-(3-(4-amino-3-(2-cyclopropoxyquinolin-6-yl)-1H-pyrazolo[3,4-d]pyrimidin-1-yl)-2,2-dimethylpropoxy)ethanol
1-(4-amino-3-(2-(2,2,2-trifluoroethoxy)quinolin-6-yl)-1H-pyrazolo[3,4-d]pyrimidin-1-yl)-2-methylpropan-2-ol
3-(4-amino-3-(2-(2,2,2-trifluoroethoxy)quinolin-6-yl)-1H-pyrazolo[3,4-d]pyrimidin-1-yl)-2,2-dimethylpropan-1-ol
3-(2-cyclopropoxyquinolin-6-yl)-1-(3-(dimethylamino)-2,2-dimethylpropyl)-1H-pyrazolo[3,4-d]pyrimidin-4-amine
3-(7-ethoxynaphthalen-2-yl)-1-isobutyl-1H-pyrazolo[3,4-d]pyrimidin-4-amine
3-(7-ethoxynaphthalen-2-yl)-1-(piperidin-4-ylmethyl)-1H-pyrazolo[3,4-d]pyrimidin-4-amine
3-(6-cyclopropoxynaphthalen-2-yl)-1-((3-methyloxetan-3-yl)methyl)-1H-pyrazolo[3,4-d]pyrimidin-4-amine
3-(6-ethoxynaphthalen-2-yl)-1-((3-methyloxetan-3-yl)methyl)-1H-pyrazolo[3,4-d]pyrimidin-4-amine
3-(2-cyclopropoxyquinolin-6-yl)-1-((3-methyloxetan-3-yl)methyl)-1H-pyrazolo[3,4-d]pyrimidin-4-amine
2-(4-amino-3-(6-ethoxynaphthalen-2-yl)-1H-pyrazolo[3,4-d]pyrimidin-1-yl)-1-morpholinoethanone
2-(4-amino-3-(6-cyclopropoxynaphthalen-2-yl)-1H-pyrazolo[3,4-d]pyrimidin-1-yl)-1-morpholinoethanone
2-((4-amino-3-(6-(methoxymethyl)naphthalen-2-yl)-1H-pyrazolo[3,4-d]pyrimidin-1-yl)methyl)-1,1,1,3,3,3-hexafluoropropan-2-ol
2-((4-Amino-3-(6-cyclopropoxynaphthalen-2-yl)-1H-pyrazolo[3,4-d]pyrimidin-1-yl)methyl)-1,1,1,3,3,3-hexafluoropropan-2-ol
2-((4-amino-3-(2-cyclopropoxyquinolin-6-yl)-1H-pyrazolo[3,4-d]pyrimidin-1-yl)methyl)-1,1,1,3,3,3-hexafluoropropan-2-ol
1-(3-(6-cyclopropoxynaphthalen-2-yl)-1H-pyrrolo[3,2-c]pyridin-1-yl)-2-methylpropan-2-ol
1-(4-amino-5-(2-cyclopropoxyquinolin-6-yl)-7H-pyrrolo[2,3-d]pyrimidin-7-yl)-2-methylpropan-2-ol
4-(4-amino-3-(2-cyclopropoxyquinolin-6-yl)-1H-pyrazolo[3,4-d]pyrimidin-1-yl)-2,3,3-trimethylbutan-2-ol
1-((4-amino-3-(2-cyclopropoxyquinolin-6-yl)-1H-pyrazolo[3,4-d]pyrimidin-1-yl)methyl)cyclobutanol
1-(4-amino-5-(6-cyclopropoxynaphthalen-2-yl)-7H-pyrrolo[2,3-d]pyrimidin-7-yl)-2-methylpropan-2-ol
1-((4-amino-3-(6-cyclopropoxynaphthalen-2-yl)-1H-pyrazolo[3,4-d]pyrimidin-1-yl)methyl)cyclobutanol
1-((4-amino-3-(2-cyclopropoxyquinolin-6-yl)-1H-pyrazolo[3,4-d]pyrimidin-1-yl)methyl)cyclopentanol
1-((4-amino-3-(6-cyclopropoxynaphthalen-2-yl)-1H-pyrazolo[3,4-d]pyrimidin-1-yl)methyl)cyclopentanol
4-((4-amino-3-(2-cyclopropoxyquinolin-6-yl)-1H-pyrazolo[3,4-d]pyrimidin-1-yl)methyl)-tetrahydro-2H-pyran-4-ol
4-((4-amino-3-(6-cyclopropoxynaphthalen-2-yl)-1H-pyrazolo[3,4-d]pyrimidin-1-yl)methyl)-tetrahydro-2H-pyran-4-ol
(3-((4-amino-3-(2-cyclopropoxyquinolin-6-yl)-1H-pyrazolo[3,4-d]pyrimidin-1-yl)methyl)oxetan-3-yl)methanol
(3-((4-amino-3-(6-cyclopropoxynaphthalen-2-yl)-1H-pyrazolo[3,4-d]pyrimidin-1-yl)methyl)oxetan-3-yl)methanol
3-(6-cyclopropoxynaphthalen-2-yl)-1-(2-methoxy-2-methylpropyl)-1H-pyrazolo[3,4-d]pyrimidin-4-amine
3-(2-cyclopropoxyquinolin-6-yl)-1-(2-methoxy-2-methylpropyl)-1H-pyrazolo[3,4-d]pyrimidin-4-amine
methyl 3-(4-amino-3-(6-cyclopropoxynaphthalen-2-yl)-1H-pyrazolo[3,4-d]pyrimidin-1-yl)-2,2-dimethylpropanoate
methyl 3-(4-amino-3-(2-cyclopropoxyquinolin-6-yl)-1H-pyrazolo[3,4-d]pyrimidin-1-yl)-2,2-dimethylpropanoate
4-((4-amino-3-(6-ethoxynaphthalen-2-yl)-1H-pyrazolo[3,4-d]pyrimidin-1-yl)methyl)piperidin-4-ol
4-((4-amino-3-(6-ethoxynaphthalen-2-yl)-1H-pyrazolo[3,4-d]pyrimidin-1-yl)methyl)-1-methylpiperidin-4-ol
methyl 2-((6-(4-amino-1-((1-methylpiperidin-4-yl)methyl)-1H-pyrazolo[3,4-d]pyrimidin-3-yl)naphthalen-2-yl)oxy)acetate
2-((6-(4-amino-1-((1-methylpiperidin-4-yl)methyl)-1H-pyrazolo[3,4-d]pyrimidin-3-yl)naphthalen-2-yl)oxy)acetonitrile
4-((4-amino-3-(6-ethoxynaphthalen-2-yl)-1H-pyrazolo[3,4-d]pyrimidin-1-yl)methyl)piperidine-4-carbonitrile
4-((4-amino-3-(6-ethoxynaphthalen-2-yl)-1H-pyrazolo[3,4-d]pyrimidin-1-yl)methyl)-1-methylpiperidine-4-carbonitrile
3-(4-amino-3-(6-cyclopropoxynaphthalen-2-yl)-1H-pyrazolo[3,4-d]pyrimidin-1-yl)-2,2-dimethylpropanoic acid
3-(6-cyclopropoxynaphthalen-2-yl)-1-(2-fluoro-2-methylpropyl)-1H-pyrazolo[3,4-d]pyrimidin-4-amine
4-((4-amino-3-(6-cyclopropoxynaphthalen-2-yl)-1H-pyrazolo[3,4-d]pyrimidin-1-yl)methyl)piperidin-4-ol
4-((4-amino-3-(6-cyclopropoxynaphthalen-2-yl)-1H-pyrazolo[3,4-d]pyrimidin-1-yl)methyl)-1-methylpiperidin-4-ol TABLE 1-continued Bumped kinase inhibitor (BKI) compounds 4-((4-amino-3-(2-ethoxyquinolin-6-yl)-1H-pyrazolo[3,4-d]pyrimidin-1-yl)methyl)-1-methylpiperidin-4-ol
4-((4-amino-3-(2-ethoxyquinolin-6-yl)-1H-pyrazolo[3,4-d]pyrimidin-1-yl)methyl)-1-methylpiperidin-4-ol
4-((4-amino-3-(2-cyclopropoxyquinolin-6-yl)-1H-pyrazolo[3,4-d]pyrimidin-1-yl)methyl)piperidin-4-ol
4-((4-amino-3-(6-cyclopropoxynaphthalen-2-yl)-1H-pyrazolo[3,4-d]pyrimidin-1-yl)methyl)-1-methylpiperidine-4-carbonitrile
4-((4-amino-3-(2-ethoxyquinolin-6-yl)-1H-pyrazolo[3,4-d]pyrimidin-1-yl)methyl)piperidin-4-ol
4-((4-amino-3-(2-cyclopropoxyquinolin-6-yl)-1H-pyrazolo[3,4-d]pyrimidin-1-yl)methyl)-1-methylpiperidin-4-ol
4-((4-amino-3-(2-ethoxyquinolin-6-yl)-1H-pyrazolo[3,4-d]pyrimidin-1-yl)methyl)piperidine-4-carbonitrile
4-((4-amino-3-(2-ethoxyquinolin-6-yl)-1H-pyrazolo[3,4-d]pyrimidin-1-yl)methyl)-1-methylpiperidine-4-carbonitrile
2-(6-(4-amino-1-(2-hydroxy-2-methylpropyl)-1H-pyrazolo[3,4-d]pyrimidin-3-yl)naphthalen-2-yloxy)acetonitrile
methyl 2-(6-(4-amino-1-(piperidin-4-ylmethyl)-1H-pyrazolo[3,4-d]pyrimidin-3-yl)quinolin-2-yloxy)acetate
3-((4-amino-3-(6-cyclopropoxynaphthalen-2-yl)-1H-pyrazolo[3,4-d]pyrimidin-1-yl)methyl)azetidin-3-ol
3-((4-amino-3-(6-cyclopropoxynaphthalen-2-yl)-1H-pyrazolo[3,4-d]pyrimidin-1-yl)methyl)-1-methylazetidin-3-ol
4-((4-amino-3-(2-cyclopropoxyquinolin-6-yl)-1H-pyrazolo[3,4-d]pyrimidin-1-yl)methyl)-1-methylpiperidine-4-carbonitrile
3-((4-amino-3-(2-ethoxyquinolin-6-yl)-1H-pyrazolo[3,4-d]pyrimidin-1-yl)methyl)azetidin-3-ol
3-(6-(difluoromethoxy)naphthalen-2-yl)-1-(piperidin-4-ylmethyl)-1H-pyrazolo[3,4-d]pyrimidin-4-amine
3-(6-(difluoromethoxy)naphthalen-2-yl)-1-((1-methylpiperidin-4-yl)methyl)-1H-pyrazolo[3,4-d]pyrimidin-4-amine
3-((4-amino-3-(6-ethoxynaphthalen-2-yl)-1H-pyrazolo[3,4-d]pyrimidin-1-yl)methyl)azetidin-3-ol
3-((4-amino-3-(6-ethoxynaphthalen-2-yl)-1H-pyrazolo[3,4-d]pyrimidin-1-yl)methyl)-1-methylazetidin-3-ol
4-((4-amino-3-(6-(difluoromethoxy)naphthalen-2-yl)-1H-pyrazolo[3,4-d]pyrimidin-1-yl)methyl)piperidin-4-ol
4-((4-amino-3-(6-(difluoromethoxy)naphthalen-2-yl)-1H-pyrazolo[3,4-d]pyrimidin-1-ylmethyl)1H-methylpiperidin-4-ol
4-((4-amino-3-(6-(difluoromethoxy)naphthalen-2-yl)-1H-pyrazolo[3,4-d]pyrimidin-1-yl)methyl)piperidine-4-carbonitrile
3-((4-amino-3-(2-cyclopropoxyquinolin-6-yl)-1H-pyrazolo[3,4-d]pyrimidin-1-yl)methyl)azetidin-3-ol
4-((4-amino-3-(6-(difluoromethoxy)naphthalen-2-yl)-1H-pyrazolo[3,4-d]pyrimidin-1-ylmethyl)1H-methylpiperidine-4-carbonitrile
3-((4-amino-3-(2-cyclopropoxyquinolin-6-yl)-1H-pyrazolo[3,4-d]pyrimidin-1-yl)methyl)-1-methylazetidin-3-ol
1-(3-(6-ethoxynaphthalen-2-yl)1H-((1-(methylcarbamoyl)piperidin-4-yl)methyl)-1H-pyrazolo[3,4-d]pyrimidin-4-yl)-3-methylurea
4-((4-amino-3-(2-ethoxyquinolin-6-yl)-1H-pyrazolo[3,4-d]pyrimidin-1-yl)methyl)-N-methylpiperidine-1-carboxamide
3-(6-ethoxynaphthalen-2-yl)-1-(1-ethylpiperidin-4-yl)-1H-pyrazolo[3,4-d]pyrimidin-4-amine
3-(2-ethoxyquinolin-6-yl)-1-isopropyl-1H-pyrazolo[3,4-d]pyrimidin-4-amine
3-(6-ethoxynaphthalen-2-yl)-1-(piperidin-4-yl)-1H-pyrazolo[3,4-d]pyrimidin-4-amine
3-(6-ethoxynaphthalen-2-yl)-1-(1-methylpiperidin-4-yl)-1H-pyrazolo[3,4-d]pyrimidin-4-amine
3-(6-ethoxynaphthalen-2-yl)-1-(2-(piperidin-4-yl)ethyl)-1H-pyrazolo[3,4-d]pyrimidin-4-amine
3-(6-ethoxynaphthalen-2-yl)-1-(2-(1-methylpiperidin-4-yl)ethyl)-1H-pyrazolo[3,4-d]pyrimidin-4-amine
3-(6-ethoxynaphthalen-2-yl)-1-(2-(1-ethylpiperidin-4-yl)ethyl)-1H-pyrazolo[3,4-d]pyrimidin-4-amine
3-(6-ethoxynaphthalen-2-yl)-1-(2-(1-propylpiperidin-4-yl)ethyl)-1H-pyrazolo[3,4-d]pyrimidin-4-amine
1-(2-(1-(3-aminopropyl)piperidin-4-yl)ethyl)-3-(6-ethoxynaphthalen-2-yl)-1H-pyrazolo[3,4-d]pyrimidin-4-amine
3-(6-ethoxynaphthalen-2-yl)-1-(1-propylpiperidin-4-yl)-1H-pyrazolo[3,4-d]pyrimidin-4-amine
1-(1-(3-aminopropyl)piperidin-4-yl)-3-(6-ethoxynaphthalen-2-yl)-1H-pyrazolo[3,4-d]pyrimidin-4-amine
1-(6-ethoxynaphthalen-2-yl)-3-(piperidin-4-ylmethyl)imidazo[1,5-a]pyrazin-8-amine
1-(6-ethoxynaphthalen-2-yl)-3-((1-methylpiperidin-4-yl)methyl)imidazo[1,5-a]pyrazin-8-amine
1-isopropyl-3-(6-(oxetan-3-yloxy)naphthalen-2-yl)-1H-pyrazolo[3,4-d]pyrimidin-4-amine
3-(6-cyclopropoxynaphthalen-2-yl)-1-((1-methylpiperidin-4-yl)methyl)-1H-pyrazolo[3,4-d]pyrimidin-4-amine
1-((6-(4-amino-1-isopropyl-1H-pyrazolo[3,4-d]pyrimidin-3-yl)naphthalen-2-yl)oxy)-2-methylpropan-2-ol TABLE 1-continued Bumped kinase inhibitor (BKI) compounds 2-((6-(4-amino-1-isopropyl-1H-pyrazolo[3,4-d]pyrimidin-3-yl)naphthalen-2-yl)oxy)ethan-1-ol
3-(6-(cyclopropylmethoxy)naphthalen-2-yl)-1-((1-methylpiperidin-4-yl)methyl)-1H-pyrazolo[3,4-d]pyrimidin-4-amine
3-(6-cyclobutoxynaphthalen-2-yl)-1-((1-methylpiperidin-4-yl)methyl)-1H-pyrazolo[3,4-d] pyrimidin-4-amine
3-(6-(2-methoxyethoxy)naphthalen-2-yl)1H-((1-methylpiperidin-4-yl)methyl)-1H-pyrazolo[3,4-d]pyrimidin-4-amine
1-((1-methylpiperidin-4-yl)methyl)-3-(6-(oxetan-3-yloxy)naphthalen-2-yl)-1H-pyrazolo[3,4-d]pyrimidin-4-amine
2-(6-(4-amino-1-((1-methylpiperidin-4-yl)methyl)-1H-pyrazolo[3,4-d]pyrimidin-3-yl)naphthalen-2-yloxy)ethanol
1-(6-(4-amino-1-((1-methylpiperidin-4-yl)methyl)-1H-pyrazolo[3,4-d]pyrimidin-3-yl)naphthalen-2-yloxy)-2-methylpropan-2-ol
3-(2-methoxyquinolin-6-yl)-1-((tetrahydro-2H-pyran-4-yl)methyl)-1H-pyrazolo[3,4-d]pyrimidin-4-amine and
3-(2-(cyclopropylmethoxy)quinolin-6-yl)-1-((tetrahydro-2H-pyran-4-yl)methyl)-1H-pyrazolo[3,4-d]pyrimidin-4-amine.

Pharmaceutical Compositions

In some embodiments, the method comprises the administration of BKI in a pharmaceutical composition having at least one pharmaceutically acceptable carrier, solvent, adjuvant or diluent.

The compounds described herein may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. The pharmaceutical compositions described herein may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compositions disclosed herein may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. The compounds of the present invention may be administered alone or in combination with at least one anti-cancer agent. The compounds of the present invention may be combined with one or more anti-cancer agents simultaneously or sequentially.

Definitions

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3 (4H)-on-5-yl, 2H-benzo[b][1,4]oxazin3 (4H)-on-6-yl, 2H-benzo[b][1,4]oxazin3 (4H)-on-7-yl, 2H-benzo[b][1,4]oxazin3 (4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl and phenanthren-9-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. In certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, acridin-9-yl, The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "nitro" as used herein, means a $-NO_2$ group.

The term "oxo" as used herein means a $=O$ group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a $=S$ group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used here, the terms "treatment" and "treating" means:
(i) inhibiting the progression the disease;
(ii) prophylactic use for example, preventing or limiting development of a disease, condition or disorder in an individual who may be predisposed or otherwise at risk to the disease, condition or disorder but does not yet experience or display the pathology or symptomatology of the disease;
(iii) inhibiting the disease; for example, inhibiting a disease, condition or disorder in an individual who is experiencing or displaying the pathology or symptomatology of the disease, condition or disorder;
(iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
(v) eliciting the referenced biological effect.

EXAMPLES

The methods of the disclosure are illustrated further by the following examples, which are not to be construed as limiting the disclosure in scope or spirit to the specific procedures and in them. It is understood that the nature of the substituents required for the desired target compound often determines the preferred method of synthesis.

General Synthetic Procedures

All chemicals were purchased from commercial suppliers and used without further purification unless otherwise stated. Reactions were monitored with thin-layer chromatography using silica gel 60 F254 coated glass plates (EM Sciences). Compound purification was performed with an IntelliFlash 280 automated flash chromatography system using pre-packed Varian Super Flash silica gel columns (hexanes/EtOAc or CH$_2$Cl$_2$/MeOH gradient solvent systems). A Varian Dynamax Microsorb 100-5 C$_{18}$ column (250 mm×21.4 mm), eluting with H$_2$O/CH$_3$CN or H$_2$O/MeOH gradient solvent systems (+0.05% TFA) was used for preparatory HPLC purification. Products were detected by UV at λ=254 nm, with all final compounds displaying >95% purity. NMR spectra were recorded on Bruker 300 or 500 MHz spectrometers at ambient temperature. Chemical shifts are reported in parts per million (δ) and coupling constants in Hz. $^1$H-NMR spectra were referenced to the residual solvent peaks as internal standards (7.26 ppm for CDCl$_3$, 2.50 ppm for d$_6$-DMSO, and 3.34 ppm for CD$_3$OD). Mass spectra were recorded with a Bruker Esquire Liquid Chromatograph-Ion Trap Mass Spectrometer.

In some examples and embodiments, the BKI compounds of the disclosure have been previously described in International Patent Publication WO 2011/0094628 and the U.S. Patent Publication 2013/0018040, both incorporated herein by reference in their entirety.

Methods of Preparation

The exemplary synthetic routes described below can be used to generate derivatives that contain varying substituents at the 1- and 3-positions of the pyrazolopyrimidine or imidazopyrazine core.

General R$_2$ Alkylation Procedure:

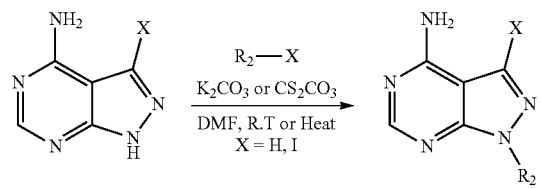

Pyrazolopyrimidine (1 equiv.), K$_2$CO$_3$, Cs$_2$CO$_3$ or K$_2$CO$_3$:NaH$_2$PO$_4$ (1.5-2 equiv.), and an alkylhalide (1.1 equiv.) or alkylmesylate (1.1 equiv.) were stirred in dry DMF at room temperature or 80° C. The reaction was monitored by thin layer chromatography. After completion, ethyl acetate and water were added and the organic phase was separated. The water phase was extracted with ethyl acetate. The combined organic phases were washed with brine, dried over Na$_2$SO$_4$ and evaporated under reduced pressure. The crude product was then purified via flash chromatography over silica, eluting with either a hexanes/EtOAc or CH$_2$Cl$_2$/MeOH gradient. If necessary, further purification was performed with preparatory RP-HPLC.

General Suzuki Coupling Procedure:

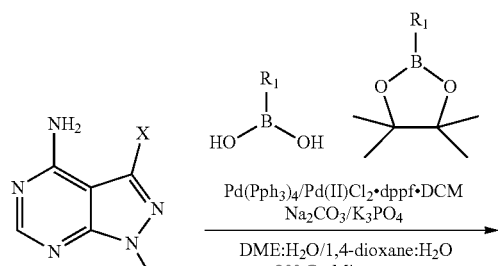

3-Iodopyrazolopyrimidines or 3-Bromopyrazolopyrimidines (1 equiv.), Na$_2$CO$_3$/K$_3$PO$_4$ (2-4 equiv.), Pd(PPh$_3$)$_4$/Pd(II)Cl$_2$dppf.DCM, (0.05 equiv.), and boronic acids or boronate pinacol esters (1-2 equiv.) were dissolved in a mixture of dimethoxyethane (1.5 mL) and water (0.5 mL) and then heated in a microwave at 80° C. for one hour. After cooling, ethyl acetate and water were added and the organic phase was separated. The water phase was extracted with ethyl acetate. The combined organic phases were washed with brine, dried over Na$_2$SO$_4$ and evaporated under reduced pressure. The crude product was then purified via flash chromatography over silica, eluting with either a hexanes/EtOAc or CH$_2$Cl$_2$/MeOH gradient. If necessary, further purification was performed with preparatory RP-HPLC.

General Naphthol Alkylation Procedure:

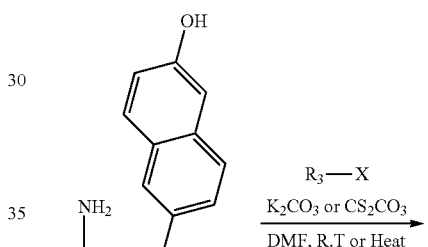

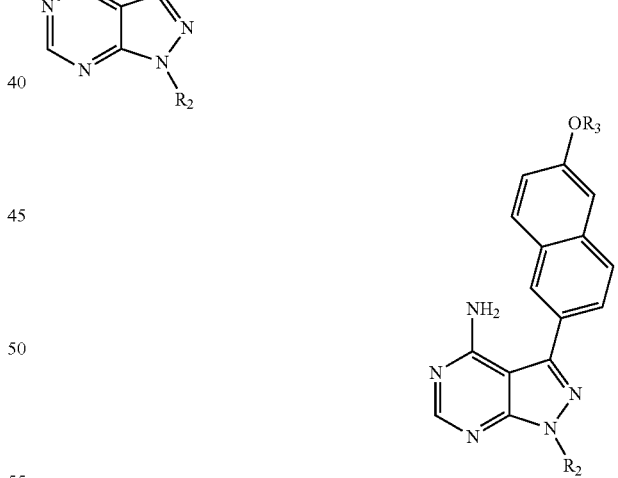

6-Hydroxy-2-naphthalene pyrazolopyrimidines (1 equiv.), K$_2$CO$_3$/CS$_2$CO$_3$ or (1.5-2 equiv.), and alkyl halides/epoxides (1.1 equiv.), NaH$_2$PO$_4$: K$_2$CO$_3$ (1:1 equiv.), were stirred in dry DMF at room temperature or 60-80° C. and monitored by thin layer chromatography. After completion, ethyl acetate and water were added and the organic phase was separated. The water phase was extracted with ethyl acetate. The combined organic phases were washed with brine, dried over Na$_2$SO$_4$ and evaporated under reduced pressure. The crude product was then purified via flash chromatography over silica, eluting with either a hexanes/

EtOAc or CH₂Cl₂/MeOH gradient. If necessary, further purification was performed with preparatory RP-HPLC.

General Boc-Deprotection Procedure:

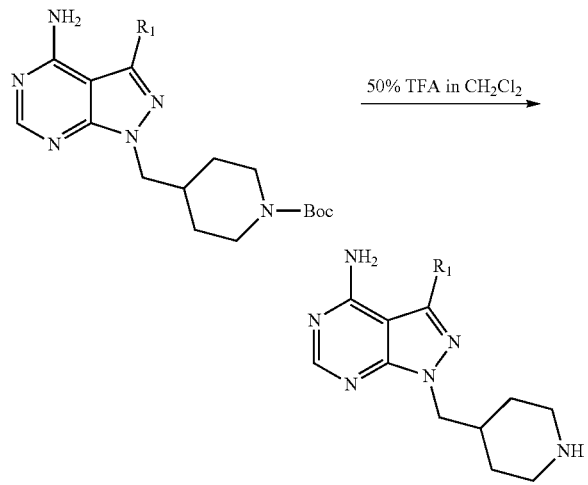

Boc-amine-containing pyrazolopyrimidines was stirred in a TFA/CH₂Cl₂ (1:1) mixture for ~3 h. The reaction was then concentrated and purified via preparatory RP-HPLC. After HPLC purification, the product was then re-concentrated from 1.25 M HCl in EtOH to afford the final, purified product as a bis-HCl salt.

General Reductive Amination Procedure:

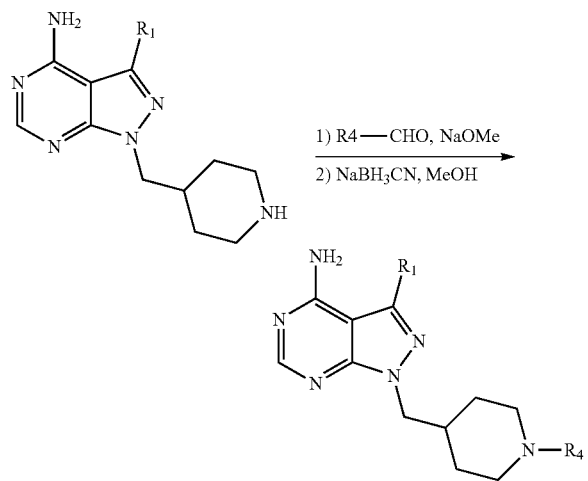

Deprotected pyrazolopyrimidines (1 equiv.) were dissolved in methanol and neutralized with sodium methoxide. A solution containing 2% acetic acid and an aldehyde or ketone (5-10 equiv.) was stirred at room temperature for 10 min. Sodium cyanoborohydride (5 equiv.) was then added and the reaction was stirred until reaching completion, as determined by thin layer chromatography (typically ~2 h). The reaction crude was then purified via preparatory RP-HPLC. After HPLC purification, the residue was dissolved in a small amount of 2 M HCl in methanol and, after concentration in vacuo, the final product was obtained as an HCl salt.

General Pinacol Ester Formation Procedure:

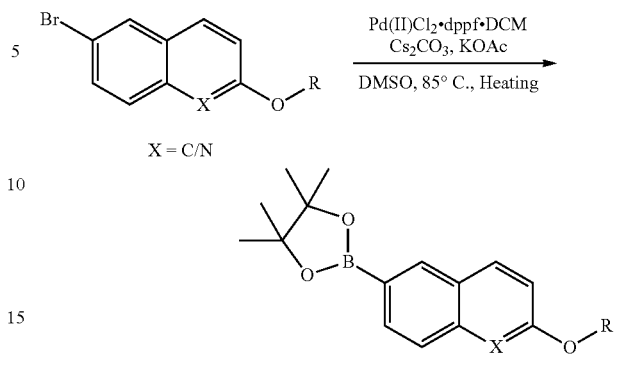

Alkylated naphthols or quinolones (1 equiv.), Cs₂CO₃ (1.5-2 equiv.), pinacolatodiborane (2.0 equiv.), Pd(II)Cl₂(dppf).DCM (0.05 equiv.), and KOAc (1 equiv.) in dry DMSO were heated at 85° C. for 5-8 h. After completion, ethyl acetate and water were added and the organic phase was separated. The water phase was extracted with ethyl acetate. The combined organic phases were washed with brine, dried over Na₂SO₄ and evaporated under reduced pressure. The crude product was then purified via flash chromatography over silica, eluting with a hexanes/EtOAc solvent gradient.

General Procedure for Boronylation Using Triisopropylborate:

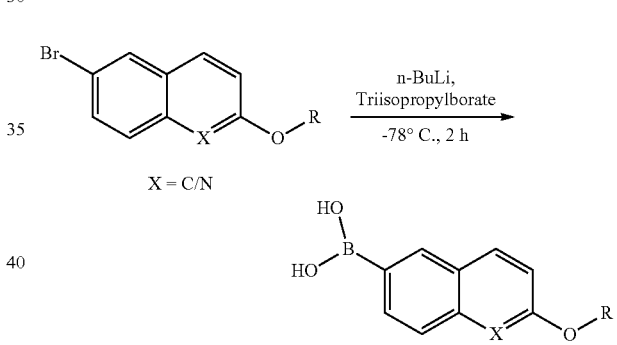

Aryl halides (1 equiv.) and triisopropylborate (1.5 equiv.) were dissolved in tetrahydrofuran:toluene (2:8), cooled to −78° C., and n-Buli (1.7 equiv.) was added dropwise over 30-40 min. After addition, the reaction was stirred at −78° C. for 1 h. After 1 h, the reaction was allowed to warm to 0° C. and stirred for 15-25 min followed by addition of 2N HCl slowly. The organic layer was separated and concentrated in vacuo to afford the desired crude product as a white crystalline product or by collecting and washing with water the white crystalline solid that forms upon addition of 2N HCl.

Example 1: 3-(6-Cyclobutoxynaphthalen-2-yl)-1-((1-methylpiperidin-4-yl)methyl)-1H-pyrazolo[3,4-d]pyrimidin-4-amine

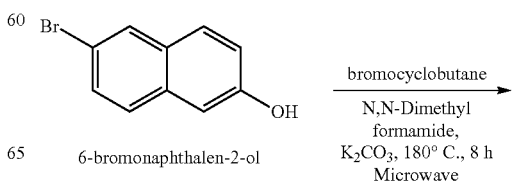

6-bromonaphthalen-2-ol

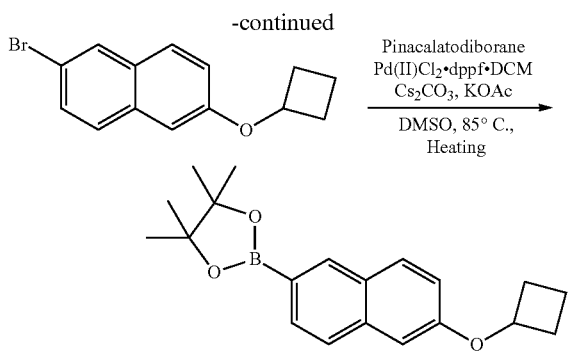

2-Bromo-6-cyclobutoxynaphthalene: 6-bromonaphthalene (700 mg, 3.1 mmol), K$_2$CO$_3$ (2.140 g, 15.5 mmol), and bromocyclobutane (1.75 mL, 18.6 mmol) in dry DMF were heated at 180° C. in a microwave for 8 h. After completion, ethyl acetate and water were added and the organic phase was separated. The aqueous phase was extracted with ethyl acetate (2×10 mL). The combined organic phases were washed with brine, dried over Na$_2$SO$_4$ and evaporated under reduced pressure. The crude product was then purified via flash chromatography over silica, eluting with a hexanes/EtOAc solvent gradient to afford 693 mg (80% yield) of pure product. $^1$H NMR (300 MHz, CDCl$_3$) δ7.88 (s, 1H), 7.65-7.43 (m, 3H), 7.10 (dd, 1H), 6.94 (s, 1H), 4.74 (m, 1H), 2.58-2.45 (m, 2H), 2.30-2.13 (m, 2H), 1.95-1.69 (m, 2H); MS (ESI) 278.5 m/z [MH$^+$], C$_{14}$H$_{14}$BrO requires 278.2.

2-(6-Cyclobutoxynaphthalen-2-yl)-4,4,5,5-tetramethyl-1,3,2-dioxaborolane: 2-Bromo-6-cyclobutoxynaphthalene and pinacolatodiborane were subjected to general pinacol ester formation procedure to afford the desired pure product (631 mg, 60% yield); $^1$H NMR (300 MHz, CDCl$_3$) δ8.26 (s, 1H), 7.93-7.61 (m, 3H), 7.2-6.93 (m, 2H), 4.80 (m, 1H), 2.67-2.36 (m, 2H), 2.41-2.11 (m, 2H), 2.01-1.60 (m, 2H), 1.37 (s, 12H); MS (ESI) 325.1 m/z [MH$^+$], C$_{20}$H$_{26}$BO$_3$ requires 325.1.

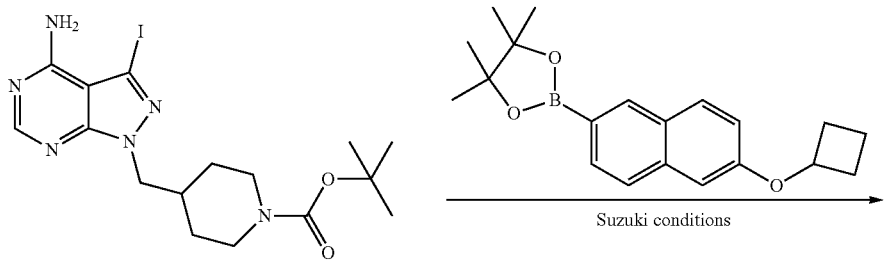

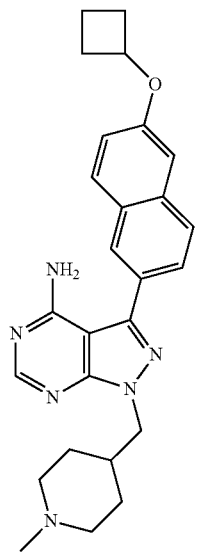

2-(6-Cyclobutoxynaphthalen-2-yl)-4,4,5,5-tetramethyl-1,3,2-dioxaborolane and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(6-cyclobutoxy-naphthalen-2-yl)-1-((1-methylpiperidin-4-yl)methyl)-1H-pyrazolo[3,4-d]pyrimidin-4-amine. $^1$H NMR (300 MHz, CD$_3$OD) δ 8.47 (s, 1H), 8.15 (s, 1H), 7.99 (d, J=8.3 Hz, 1H), 7.92 (d, J=9.5 Hz, 1H), 7.80 (d, J=8.9 Hz, 1H), 7.24 (m, 2H), 4.53 (d, J=6.6 Hz, 2H), 3.56 (m, 2H), 3.03 (m, 2H), 2.86 (s, 3H), 2.62 (m, 2H), 2.44 (m, 1H), 2.22 (m, 2H), 2.04-1.60 (m, 6H); MS (ESI) 443.4 m/z [MH+], C$_{26}$H$_{31}$N$_6$O requires 443.2.

Example 2: 3-(4-Amino-3-(2-(2,2,2-trifluoroethoxy)quinolin-6-yl)-1H-pyrazolo[3,4-d]pyrimidin-1-yl)-2,2-dimethylpropan-1-ol

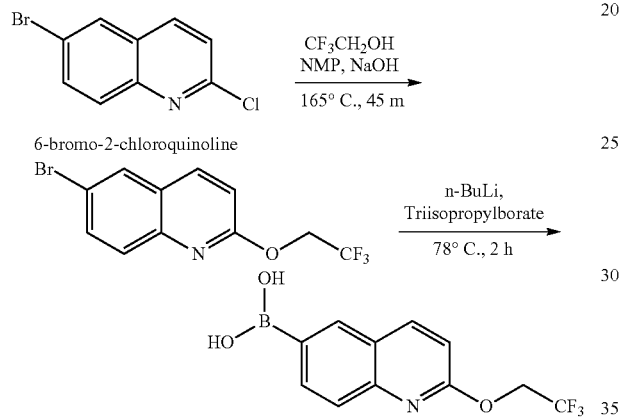

6-Bromo-2-(2,2,2-trifluoroethoxy)quinolone: 6-bromo-2-chloroquinoline (1.00 g, 4.1 mmol), CF$_3$CH$_2$OH (0.95 mL, 12.3 mmol), N-Methylmorpholine (12 mL), and NaOH (330 mg, 8.2 mmol) were taken in microwave tube and then heated at 165° C. for 45 min. After addition of water, the reaction mixture was extracted with ethyl acetate (3×20 mL). The organic layer was washed with brine, dried over sodium sulfate, and evaporated under reduced pressure. The crude compound was then taken to the next step without further purification.

Synthesis of 2-(2,2,2-Trifluoroethoxy)quinolin-6-ylboronic acid: 6-Bromo-2-(2,2,2-trifluoroethoxy)quinoline was subjected to the general procedure for boronylation using triisopropylborate to afford a white crystalline product (354 mg, 80% yield,). $^1$H NMR (300 MHz, CD$_3$OD) δ 6.91 (s, 1H), 6.82 (d, J=8.5 Hz, 1H), 6.45 (s, 2H) 6.61 (d, J=7.04 Hz, 1H), 3.5 (q, J=8.7 Hz, 2H); MS (ESI) 272.4 m/z [MH+], C$_{11}$H$_{10}$BF$_3$NO$_3$ requires 272.2.

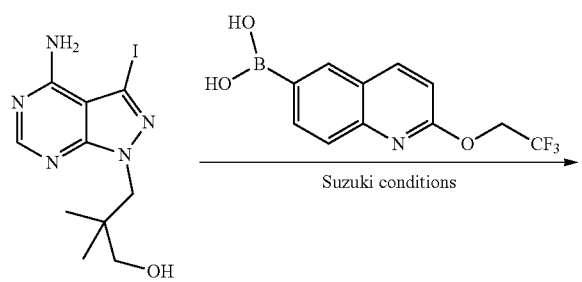

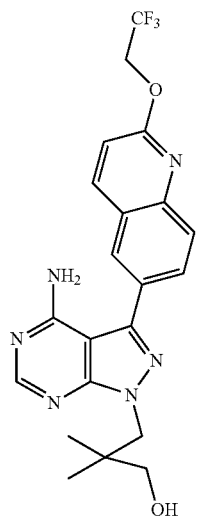

2-(2,2,2-Trifluoroethoxy)quinolin-6-ylboronic acid and 3-(4-amino-3-iodo-1H-pyrazolo-[3,4-d]pyrimidin-1-yl)-2,2-dimethylpropan-1-ol were subjected to the general Suzuki coupling procedure in order to afford 3-(4-Amino-3-(2-(2,2,2-trifluoroethoxy)quinolin-6-yl)-1H-pyrazolo[3,4-d]pyrimidin-1-yl)-2,2-dimethylpropan-1-ol. $^1$H NMR (300 MHz, CD$_3$OD) δ 8.40 (s, 1H), 8.17 (d, J=8.7 Hz, 1H), 8.07 (d, J=1.6 Hz, 1H), 8.01-7.95 (m, 2H), 7.12 (d, J=8.9 Hz, 1H), 4.98 (q, J=8.5 Hz, 2H), 4.35 (s, 2H), 3.15 (s, 2H), 1.05 (s, 6H); MS (ESI) 447.5 m/z [MH+], C$_{21}$H$_{21}$F$_3$N$_6$O$_2$ requires 447.4.

Example 3: 3-(2-Cyclopropoxyquinolin-6-yl)-1-((1-methylpiperidin-4-yl)methyl)-1H-pyrazolo[3,4-d]pyrimidin-4-amine

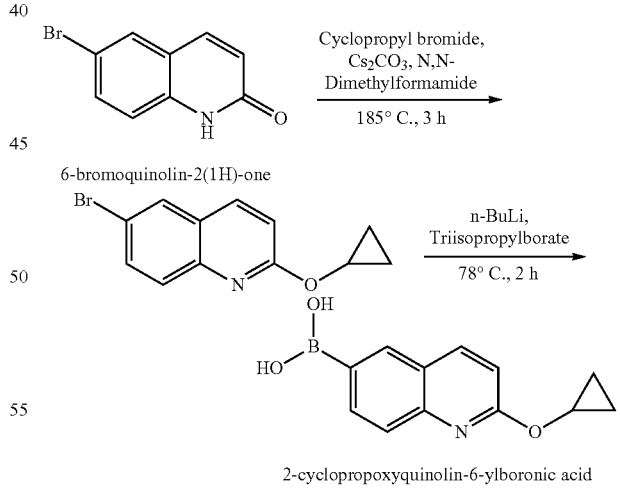

6-Bromo-2-cyclopropoxyquinoline: 6-Bromo-quinolin-2(1H)-one (1.00 g, 4.4 mmol, 1 equiv.), Cs$_2$CO$_3$ (5.08 g, 17.8 mmol), and bromocyclopropane (1.06 g, 13.3 mmol) in dry DMF (10 mL) were heated at 180° C. in a microwave for 3 h. After completion, ethyl acetate and water were added and the organic phase was separated. The water phase was further extracted with ethyl acetate. The combined organic phases were washed with brine, dried over Na$_2$SO$_4$ and evaporated under reduced pressure. The crude product was then purified via flash chromatography over silica, eluting with a hexanes/EtOAc solvent gradient to afford 0.235 mg (20% yield) of pure product. $^1$H NMR (300 MHz, CDCl$_3$) δ 7.89 (s, 1H), 7.87-7.82 (m, 1H), 7.78-7.65 (m, 2H), 6.88 (d, J=8.91 Hz, 1H), 4.54-4.44 (m, 1H), 0.94-0.77 (m, 4H); MS (ESI) 265.5 m/z [MH$^+$], C$_{12}$H$_{11}$BrNO requires 265.2.

2-Cyclopropoxyquinolin-6-ylboronic acid: 6-Bromo-2-cyclopropoxyquinoline (2.01 g, 7.95 mmol, 1 equiv.) and triisopropylborate (2.05 mg, 13.5 mmol, 1.69 equiv.) were subjected to General procedure for boronylation using tri-isopropylborate to afford the desired pure product (1.05 g, 80% yield); $^1$H NMR (300 MHz, DMSO) δ 8.37-8.28 (m, 2H), 8.10-8.04 (m, 1H), 7.77 (d, J=8.5 Hz, 1H), 7.06 (d, J=8.9 Hz, 1H), 4.55-4.45 (m, 1H), 0.91-0.81 (m, 2H), 0.80-0.73 (m, 2H); MS (ESI) 230.2 m/z [MH$^+$], C$_{12}$H$_{13}$BNO$_3$ requires 230.2.

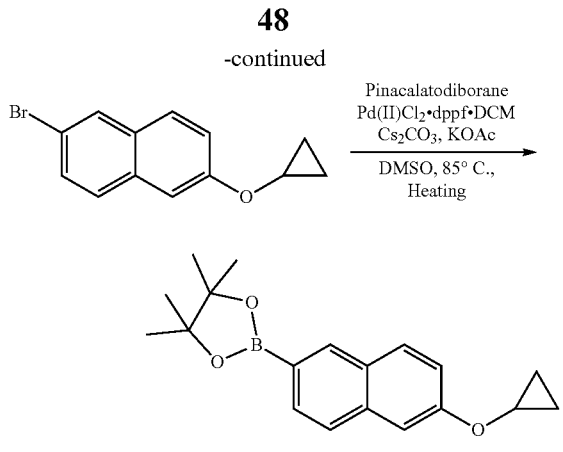

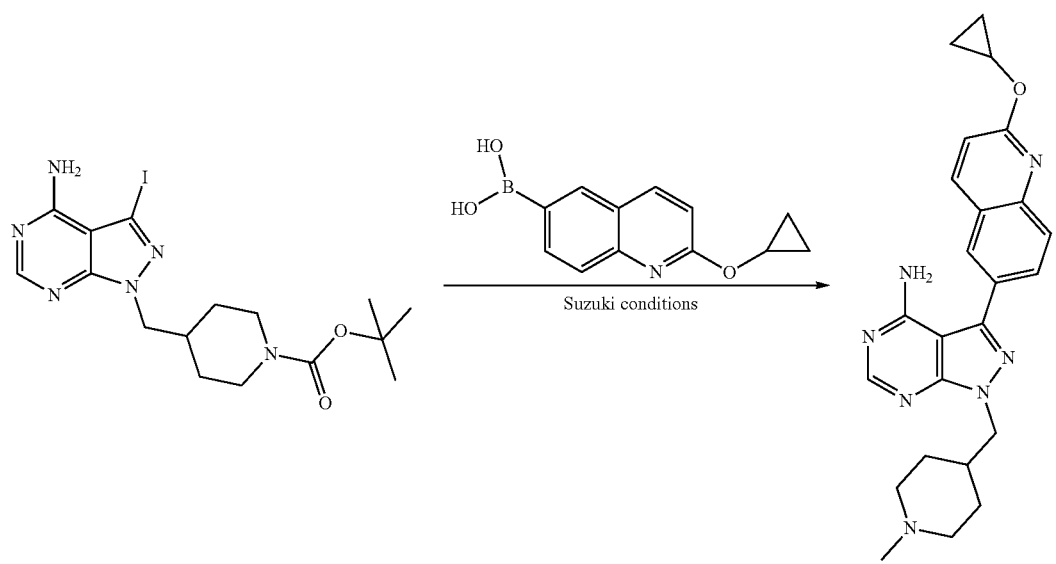 [SMILES: CC(C)(C)OC(=O)N1CCC(Cn2nc(I)c3c(N)ncnc32)CC1 ; OB(O)c1ccc2nc(OC3CC3)ccc2c1 ; CN1CCC(Cn2nc(-c3ccc4nc(OC5CC5)ccc4c3)c3c(N)ncnc32)CC1]

2-Cyclopropoxyquinolin-6-ylboronic acid and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(2-cyclopropoxyquinolin-6-yl)-1-((1-methylpiperidin-4-yl)methyl)-1H-pyrazolo[3,4-d]pyrimidin-4-amine. $^1$H NMR (300 MHz, CD$_3$OD) δ 9.17 (s, 1H), 8.75-8.33 (m, 3H), 8.28-7.98 (m, 2H), 4.72 (m, 1H), 4.54 (d, J=6.0 Hz, 2H), 3.56 (m, 2H), 3.10 (m, 2H), 3.00 (s, 3H), 2.48 (m, 1H), 2.00 (m, 2H), 1.60 (m, 2H), 1.20-1.10 (m, 4H); MS (ESI) 430.5 m/z [MH+], C$_{24}$H$_{28}$N$_7$O requires 430.6.

Example 4: 3-(6-Cyclopropoxynaphthalen-2-yl)-1-((1-methylpiperidin-4-yl)methyl)-1H-pyrazolo[3,4-d]pyrimidin-4-amine

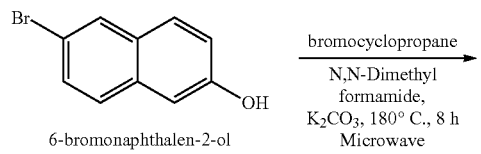

2-Bromo-6-cyclopropoxynaphthalene: 6-Bromonaphthalen-2-ol (3.00 g, 13.0 mmol), Cs$_2$CO$_3$ (1.29 g, 39.6 mmol) and bromocyclopropane (4.07 g, 39.0 mmol) were taken in a microwave tube and heated at 180° C. for 30 min. After completion, ethyl acetate and water were added and the organic phase was separated. The water phase was further extracted with ethyl acetate. The combined organic phases were washed with brine, dried over Na$_2$SO$_4$ and evaporated under reduced pressure. The crude product was then purified via flash chromatography over silica, eluting with a hexanes/EtOAc solvent gradient to afford 2.50 g (71% yield) of pure product. $^1$H NMR (300 MHz, CDCl$_3$): δ ppm 7.91 (m, 1H), 7.66-7.58 (dd, J=8.9, 4.6 Hz, 2H), 7.53-7.46 (dd, J=8.7, 1.9 Hz, 1H), 7.39 (d, J=2.1 Hz, 1H), 7.18-7.12 (dd, J=8.9, 2.3 Hz, 1H), 3.83 (m, 1H), 0.87-0.78 (m, 4H); MS (ESI): 264.2 m/z [MH+], C$_{13}$H$_{12}$BrO requires 264.2.

2-(6-Cyclopropoxynaphthalen-2-yl)-4,4,5,5-tetramethyl-1,3,2-dioxaborolane: 2-Bromo-6-cyclopropoxynaphthalene was subjected to the general pinacol ester formation procedure to afford 1.01 g, (65% yield) of a white crystalline product. $^1$H NMR (300 MHz, CDCl$_3$): δ ppm 8.27 (s, 1H), 7.77 (m, 3H) 7.45 (d, J=2.3 Hz, 1H), 7.14 (dd, J=8.9, 2.48 Hz, 1H), 3.88 (m, 1H), 1.40 (s, 12H), 0.87 (m, 2H), 0.82 (m, 2H); MS (ESI): 311.5 m/z [MH+], C$_{19}$H$_{24}$BO$_3$ requires 311.2.

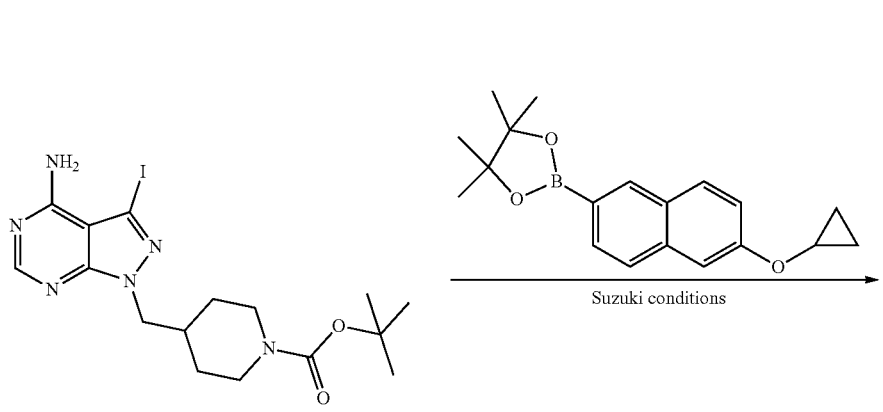

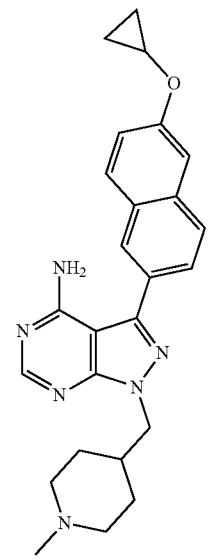

2-(6-Cyclopropoxynaphthalen-2-yl)-4,4,5,5-tetramethyl-1,3,2-dioxaborolane and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford 3-(6-cyclopropoxynaphthalen-2-yl)-1-((1-methylpiperidin-4-yl)methyl)-1H-pyrazolo[3,4-d]pyrimidin-4-amine. $^{1}$H NMR (300 MHz, CD$_3$OD) δ 8.49 (s, 1H), 8.17 (s, 1H), 8.03 (d, J=8.5 Hz, 1H), 7.92 (d, J=9.1 Hz, 1H), 7.80 (d, J=8.5 Hz, 1H), 7.64 (d, J=2.0 Hz, 1H), 7.27 (dd, J=8.9, 1.8 Hz, 1H), 4.52 (d, J=6.0 Hz, 2H), 3.98 (m, 1H), 3.56 (m, 2H), 3.05 (m, 2H), 2.87 (s, 3H), 2.44 (m, 1H), 2.00 (m, 2H), 1.76 (m, 2H), 0.92 (m, 2H), 0.80 (m, 2H); MS (ESI) 429.5 m/z [MH+], C$_{25}$H$_{29}$N$_6$O requires 429.6.

Example 5: 3-(2-Cyclopropoxyquinolin-6-yl)-1-(3-(dimethylamino)-2,2-dimethylpropyl)-1H-pyrazolo[3,4-d]pyrimidin-4-amine 1-(3-(Dimethylamino)-2,2-dimethylpropyl)-3-iodo-1H-pyrazolo[3,4-d]pyrimidin-4-amine was generated with 3-iodo-1H-pyrazolo[3,4-d]pyrimidin-4-amine and 3-bromo-N,N,2,2-tetramethylpropan-1-amine using the general R$_2$ alkylation procedure, to afford the product as pale yellow solid, (286 mg, 40% yield); $^{1}$H NMR (300 MHz, MeOD4) δ 8.38 (s, 1H), 4.46 (s, 2H), 3.22 (s, 2H), 3.06 (s, 6H), 1.16 (s, 6H); MS (ESI) 375.2 [MH+], C$_{12}$H$_{20}$IN$_6$ requires 375.2.

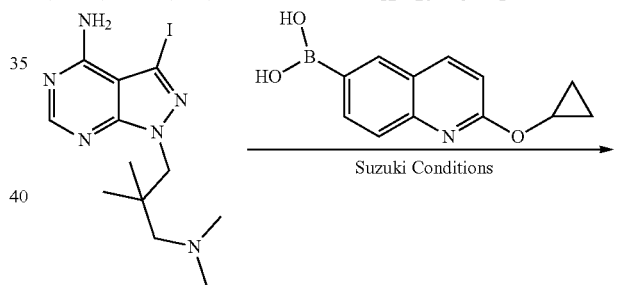

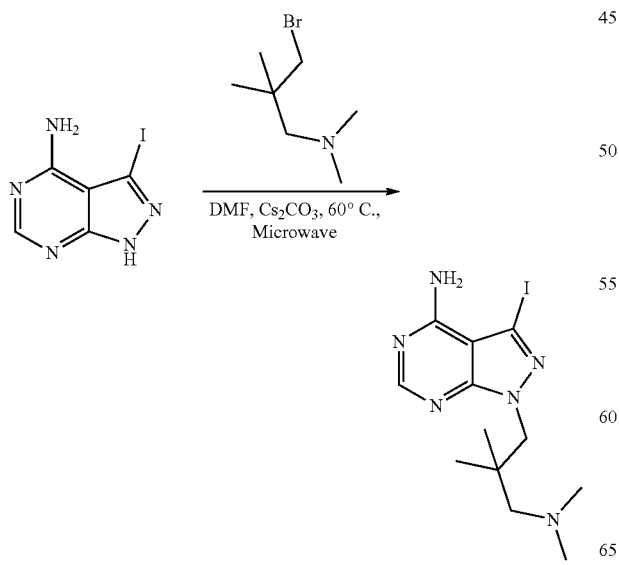

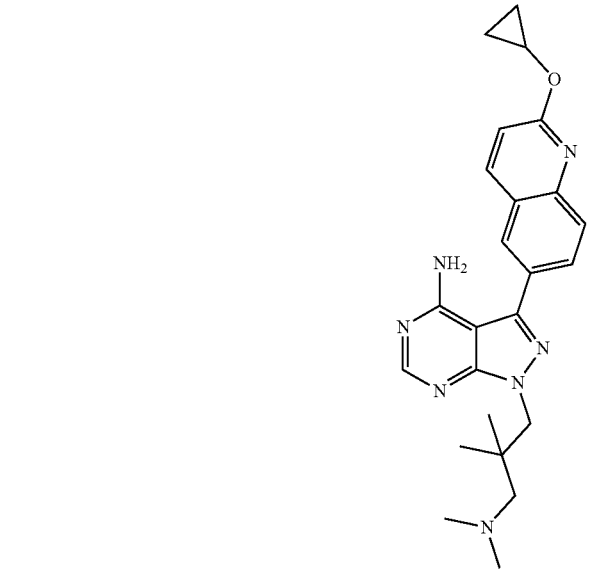

2-Cyclopropoxyquinolin-6-ylboronic acid and 1-(3-(dimethylamino)-2,2-dimethylpropyl)-3-iodo-1H-pyrazolo[3,4-d]pyrimidin-4-amine were subjected to the general Suzuki coupling procedure to afford 3-(2-cyclopropoxyquinolin-6-yl)-1-(3-(dimethylamino)-2,2-dimethylpropyl)-1H-pyrazolo[3,4-d]pyrimidin-4-amine. $^1$H NMR (300 MHz, CD$_3$OD) δ 8.29 (s, 1H), 8.22 (d, J=8.9 Hz, 1H), 8.11 (d, J=1.6 Hz, 1H) 8.01 (s, 1H), 8.00 (dd, J=8.5, 1.5 Hz, 1H), 7.07 (d, J=8.9 Hz, 1H), 4.46 (m, 1H), 4.36 (s, 2H), 2.46 (s, 2H), 2.44 (s, 6H), 1.03 (s, 6H), 0.93-0.82 (m, 4H). MS (ESI) 432.6 m/z [MH+], C$_{24}$H$_{30}$N$_7$O requires 432.5.

Example 6: 1-(4-amino-3-(6-ethoxynaphthalen-2-yl)-1H-pyrazolo[3,4-d]pyrimidin-1-yl)-2-methylpropan-2-ol

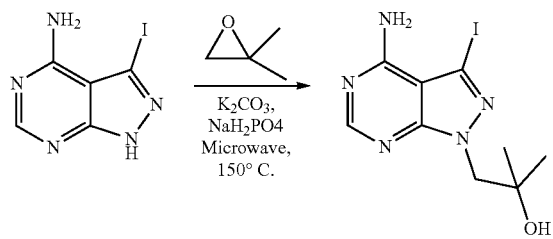

1-(4-Amino-3-iodo-1H-pyrazolo[3,4-d]pyrimidin-1-yl)-2-methylpropan-2-ol was generating using the general R$_2$ alkylation procedure using 3-iodo-1H-pyrazolo[3,4-d]pyrimidin-4-amine (500 mg, 1.92 mmol), 2,2-dimethyloxirane (0.276 mg, 3.80 mmol), and K$_2$CO$_3$:NaH$_2$PO$_4$ (0.262 mg, 1.90 mmol) in 3 mL of a acetonitrile:water (8.5:1.5) mixture. The reaction was stirred at 150° C. for 3 h in a microwave, affording 1-(4-amino-3-iodo-1H-pyrazolo[3,4-d]pyrimidin-1-yl)-2-methylpropan-2-ol (150 mg, yield, 23.4% yield) as a white solid after purification using a methanol/dichloromethane solvent gradient. $^1$H NMR (300 MHz, CD$_3$OD) δ 8.26 (s, 1H), 4.37 (s, 2H), 1.29 (s, 6H). MS (ESI) m/z 334.2 [MH$^+$], C$_9$H$_{13}$IN$_5$O requires 334.1.

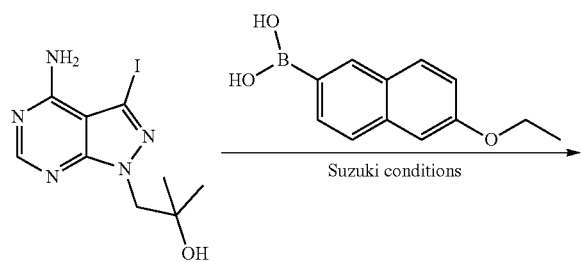

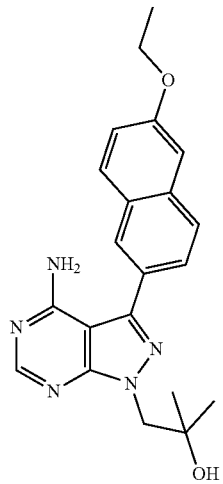

6-ethoxynaphthalen-2-ylboronic acid and 1-(4-amino-3-iodo-1H-pyrazolo[3,4-d]pyrimidin-1-yl)-2-methylpropan-2-ol were subjected to the general Suzuki coupling procedure to afford compound 1-(4-amino-3-(6-ethoxynaphthalen-2-yl)-1H-pyrazolo[3,4-d]pyrimidin-1-yl)-2-methylpropan-2-ol; $^1$H NMR (300 MHz, CD$_3$OD) δ 8.26 (s, 1H), 8.09 (s, 1H), 7.97-7.83 (m, 2H), 7.76 (dd, J=8.2, 1.4 Hz, 1H), 7.30 (d, J=2.0 Hz, 1H), 7.20 (dd, J=8.9, 1.4 Hz, 1H), 4.41 (s, 2H), 4.19 (q, J=7.0 Hz, 2H), 1.47 (t, J=6.8 Hz, 3H), 1.28 (s, 6H). MS (ESI) 378.2 m/z [MH+], C$_{21}$H$_{24}$N$_5$O$_2$ requires 378.1.

Example 7: 3-(6-cyclopropoxynaphthalen-2-yl)-1-((3-methyloxetan-3-yl)methyl)-1H-pyrazolo[3,4-d]pyrimidin-4-amine

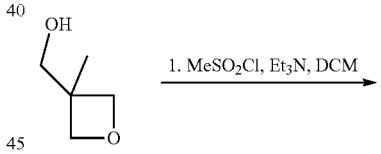

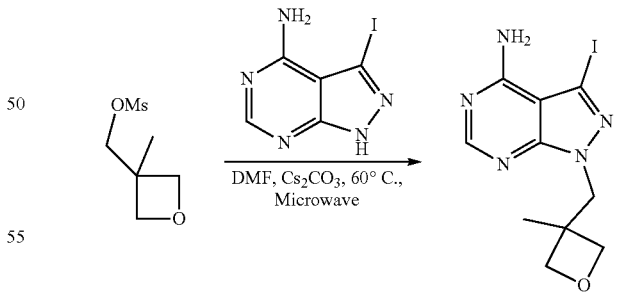

Methanesulfonyl chloride (7.54 mL, 97.9 mmol) was added slowly at 0° C. to a solution of (3-methyloxetan-3-yl)methanol (5.00 mg, 48.9 mmol) and triethylamine (13 mL, 97 mmol) in dichloromethane (20 mL). The reaction was stirred for 5 h at room temperature. After completion of the reaction, dichloromethane was removed by reduced pressure and the reaction was diluted with ethyl acetate. The ethyl acetate was washed with NaHCO$_3$ (25 mL), 1N HCl, brine (50 mL), dried over sodium sulfate, and concentrated. The crude product was subjected to flash chromatography using a hexane/ethyl acetate solvent gradient to afford pure 3-methyloxetan-3-yl)methyl methanesulfonate (4.40 g, 50% yield). $^1$H NMR (301 MHz, CDCl$_3$) δ 4.70-4.12 (m, 6H), 3.07 (s, 3H), 1.39 (s, 3H); MS (ESI) 181.1 [MH+], C$_6$H$_{13}$O$_4$S requires 181.0.

3-Iodo-1-((3-methyloxetan-3-yl)methyl)-1H-pyrazolo[3,4-d]pyrimidin-4-amine was generated by subjecting 3-iodo-1H-pyrazolo[3,4-d]pyrimidin-4-amine (150 mg, 0.60 mmol) and (3-methyloxetan-3-yl)methyl methanesulfonate (83 mg, 0.46 mmol) to the general R$_2$ alkylation procedure (110 mg, 55% yield). $^1$H NMR (300 MHz, CDCl$_3$) δ 8.33 (s, 1H), 5.94 (s, 2H), 4.79 (d, J=6.4 Hz, 2H), 4.56 (s, 2H), 4.41 (d, J=6.1 Hz, 2H), 1.28 (s, 3H); MS (ESI) m/z 346.2 [MH$^+$], C$_{10}$H$_{13}$IN$_5$O requires 346.1.

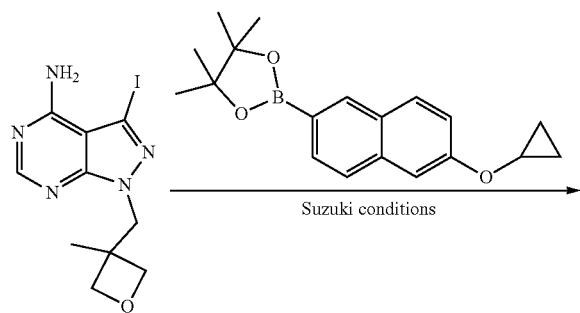

2-(6-cyclopropoxynaphthalen-2-yl)-4,4,5,5-tetramethyl-1,3,2-dioxaborolane and 3-iodo-1-((3-methyloxetan-3-yl)methyl)-1H-pyrazolo[3,4-d]pyrimidin-4-amine were subjected to the general Suzuki coupling procedure in order to afford 3-(6-cyclopropoxynaphthalen-2-yl)-1-((3-methyloxetan-3-yl)methyl)-1H-pyrazolo[3,4-d]pyrimidin-4-amine. $^1$H NMR (300 MHz, CDCl$_3$) δ 8.39 (s, 1H), 8.08 (s, 1H), 7.93 (d, J=8.7 Hz, 1H), 7.83 (d, J=8.9 Hz, 1H), 7.77 (d, J=9.4 Hz, 1H), 7.52 (s, 1H), 7.24 (dd, J=10.0, 3.0 Hz, 1H), 5.68 (s, 2H), 4.90 (d, J=6.1 Hz, 2H), 4.64 (s, 2H), 4.45 (d, J=6.1 Hz, 2H), 3.91 (m, 1H), 1.36 (3, 3H), 0.96-0.83 (m, 4H); MS (ESI) 402.2 m/z [MH+], C$_{23}$H$_{24}$N$_5$O$_2$ requires 402.4.

Example 8: 2-((4-Amino-3-(6-cyclopropoxynaphthalen-2-yl)-1H-pyrazolo[3,4-d]pyrimidin-1-yl)methyl)-1,1,1,3,3,3-hexafluoropropan-2-ol

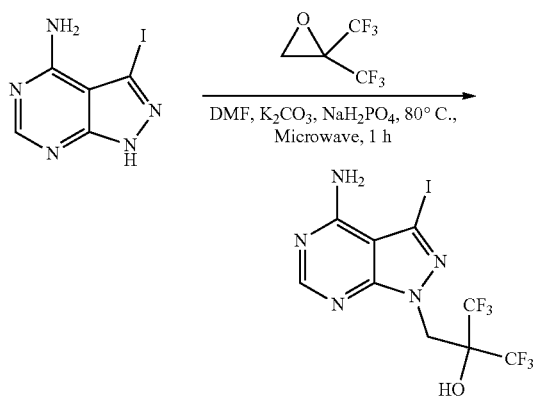

2-((4-Amino-3-iodo-1H-pyrazolo[3,4-d]pyrimidin-1-yl)methyl)-1,1,1,3,3,3-hexafluoropropan-2-ol was generated by subjecting 3-iodo-1H-pyrazolo[3,4-d]pyrimidin-4-amine (250 mg, 0.96 mmol), 2,2-bis(trifluoromethyl)oxirane (0.17 mL, 1.44 mmol), and K$_2$CO$_3$:NaH$_2$PO$_4$ (198 mg, 1.44 mmol) to the general R$_2$ alkylation procedure (126 mg, 30% yield). $^1$H-NMR (301 MHz, CDCl$_3$) δ 8.33 (s, 1H), 8.02 (s, 1H), 6.33 (s, 2H); MS (ESI) m/z 442.1 [MH$^+$], C$_9$H$_6$F$_6$IN$_5$O requires 442.2.

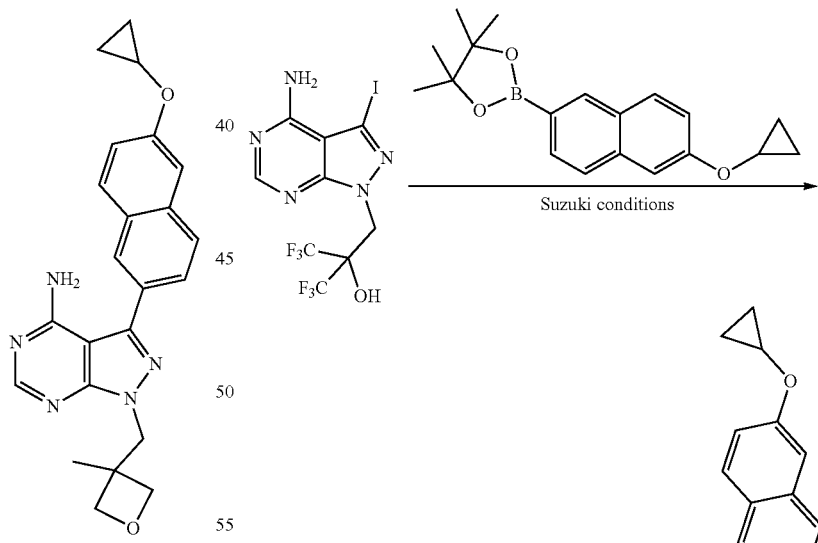

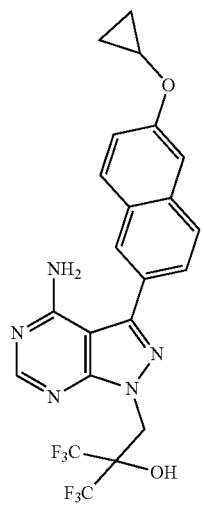

2-(6-Cyclopropoxynaphthalen-2-yl)-4,4,5,5-tetramethyl-1,3,2-dioxaborolane and 2-((4-amino-3-iodo-1H-pyrazolo[3,4-d]pyrimidin-1-yl)methyl)-1,1,1,3,3,3-hexafluoropropan-2-ol were subjected to the general Suzuki coupling procedure in order to afford 2-((4-amino-3-(6-cyclopropoxynaphthalen-2-yl)-1H-pyrazolo[3,4-d]pyrimidin-1-yl)methyl)-1,1,1,3,3,3-hexafluoropropan-2-ol. $^1$H NMR (300 MHz, CD$_3$OD) δ 8.32 (s, 1H), 8.11 (s, 1H), 7.97 (d, J=8.5 Hz, 1H), 7.87 (d, J=9.1 Hz, 1H), 7.76 (dd, J=8.5, 1.6 Hz, 1H), 7.59 (d, J=2.0, 1H), 7.23 (dd, J=8.9, 2.2 Hz, 1H), 5.03 (s, 2H), 3.94 (m, 1H), 0.94-0.76 (m, 4H); MS (ESI) 498.2 m/z [MH+], $C_{22}H_{18}F_6N_5O_2$ requires 498.2.

Example 9: 3-(6-cyclopropoxynaphthalen-2-yl)-1-isobutyl-1H-pyrazolo[3,4-d]pyrimidin-4-amine

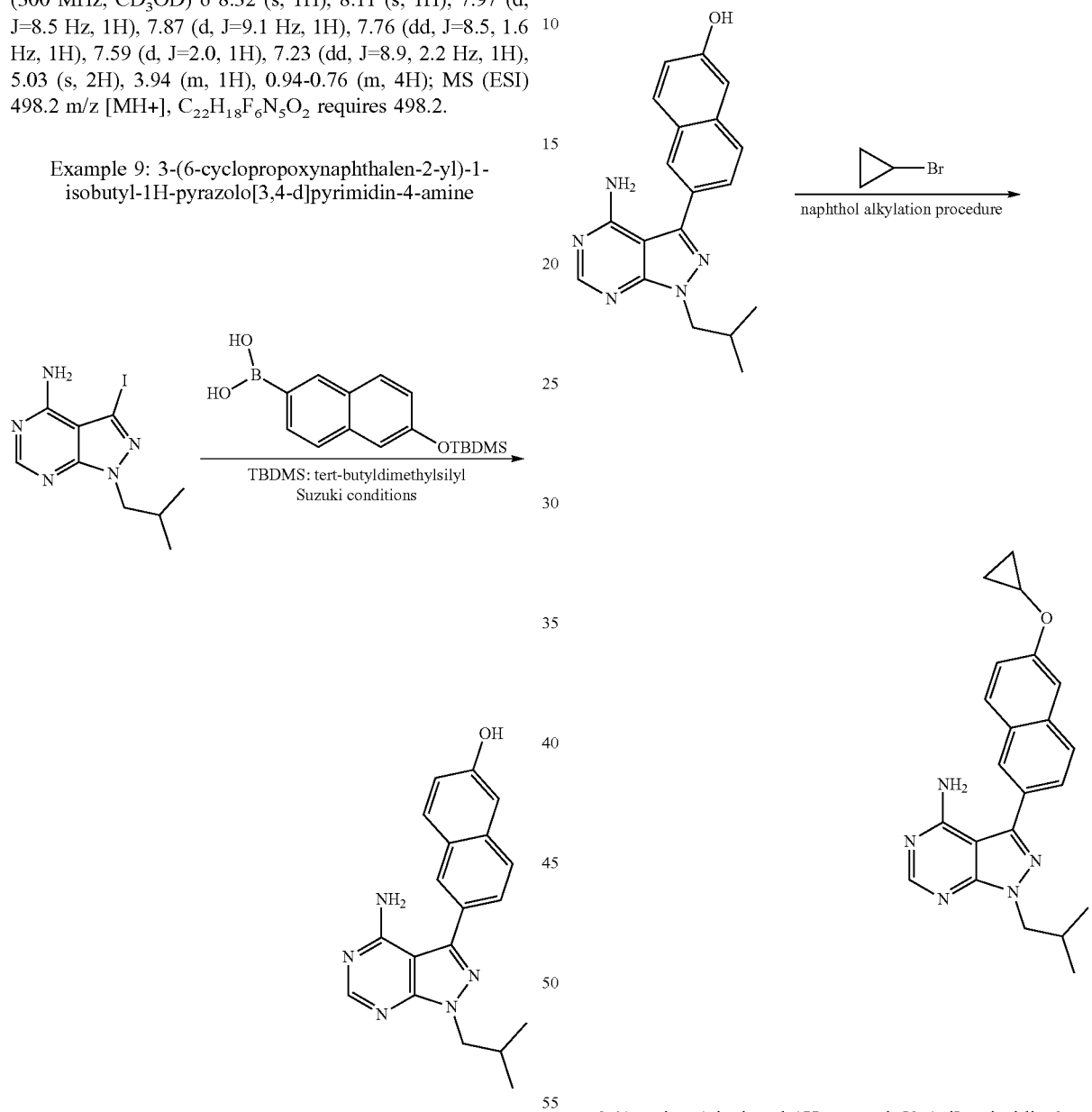

6-tert-butyldimethylsilyloxy-2-naphthaleneboronic acid and 3-iodo-1-isobutyl-1H-pyrazolo[3,4-d]pyrimidin-4-amine[2] were subjected to the general Suzuki coupling procedure. The crude product was purified by silica gel using dichloromethane/methanol gradient (note: deprotection of the tert-butyldimethylsilyloxy protecting group was observed after purification). $^1$H NMR (300 MHz, CD$_3$OD) δ 8.27 (s, 1H), 8.03 (s, 1H), 7.82 (m, 2H), 7.71 (m, 1H), 7.18 (m, 2H), 4.21 (d, J=4.2 Hz, 2H), 2.39 (m, 1H), 0.96 (d, J=6.5 Hz, 6H); MS (ESI) 334.4 m/z [MH+], $C_{19}H_{19}N_5O$ requires 334.2.

6-(4-amino-1-isobutyl-1H-pyrazolo[3,4-d]pyrimidin-3-yl)naphthalen-2-ol and bromocyclopropane were subjected to the general naphthol alkylation procedure in order to afford 3-(6-cyclopropoxynaphthalen-2-yl)-1-isobutyl-1H-pyrazolo[3,4-d]pyrimidin-4-amine. $^1$H NMR (300 MHz, CD$_3$OD) δ 8.27 (s, 1H), 8.10 (s, 1H), 7.98 (d, J=8.7 Hz, 1H), 7.89 (d, J=8.9 Hz, 1H), 7.76 (dd, J=8.5, 1.6 Hz, 1H), 7.61 (d, J=2.2 Hz, 1H), 7.25-7.18 (dd, J=8.9, 2.2 Hz, 1H), 4.24 (d, J=7.25 Hz, 2H), 3.95 (m, 1H), 2.38 (m, 1H), 0.97 (d, J=6.6 Hz, 6H), 0.90 (m, 2H), 0.79 (m, 2H); MS (ESI) 374.2 m/z [MH+], $C_{22}H_{24}N_5O$ requires 374.4.

Example 10: 3-(6-(Cyclopropylmethoxy)naphthalen-2-yl)-1-((1-methylpiperidin-4-yl)methyl)-1H-pyrazolo[3,4-d]pyrimidin-4-amine

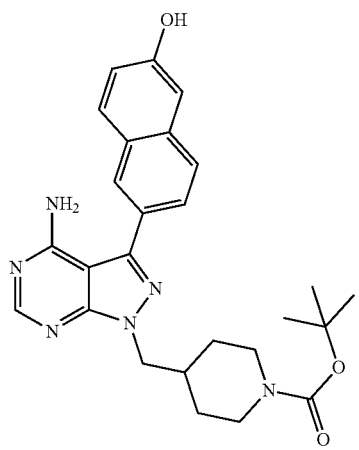

Tert-butyl 4-((4-amino-3-(6-hydroxynaphthalen-2-yl)-1H-pyrazolo[3,4-d]pyrimidin-1-yl)methyl)piperidine-1-carboxylate and (bromomethyl)cyclopropane were subjected to the general naphthol alkylation procedure followed by the general boc-deprotection procedure and general reductive amination procedure in order to afford the product. $^1$H NMR (300 MHz, CD$_3$OD) δ 8.51 (s, 1H), 8.17 (s, 1H), 8.01 (d, J=8.5 Hz, 1H), 7.93 (d, J=9.1 Hz, 1H), 7.81 (d, J=9.3 Hz, 1H), 7.36 (s, 1H), 7.30 (d, J=9.3 Hz, 1H), 4.56 (d, J=6.4 Hz, 2H), 4.03 (d, J=6.6 Hz, 2H), 3.57 (m, 2H), 3.06 (m, 2H), 2.88 (s, 3H), 2.45 (m, 1H), 2.02 (m, 2H), 1.77 (m, 2H), 1.44 (m, 1H), 0.71 (m, 2H), 0.46 (m, 2H); MS (ESI) 443.5 m/z [MH+], C$_{26}$H$_{31}$N$_6$O requires 443.5.

Example 11: 3-(6-(2-Methoxyethoxy)naphthalen-2-yl)-1-((1-methylpiperidin-4-yl)methyl)-1H-pyrazolo[3,4-d]pyrimidin-4-amine

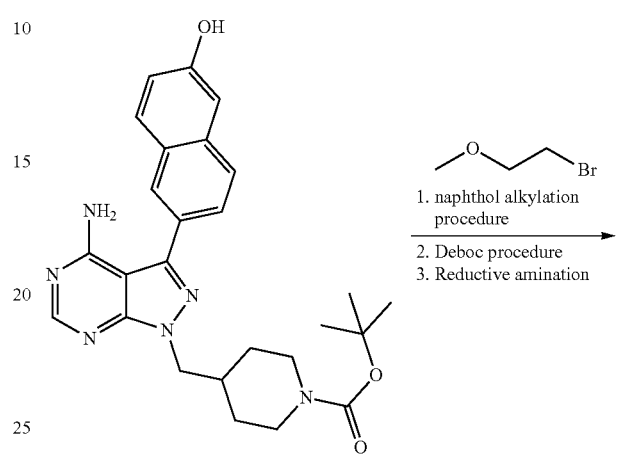

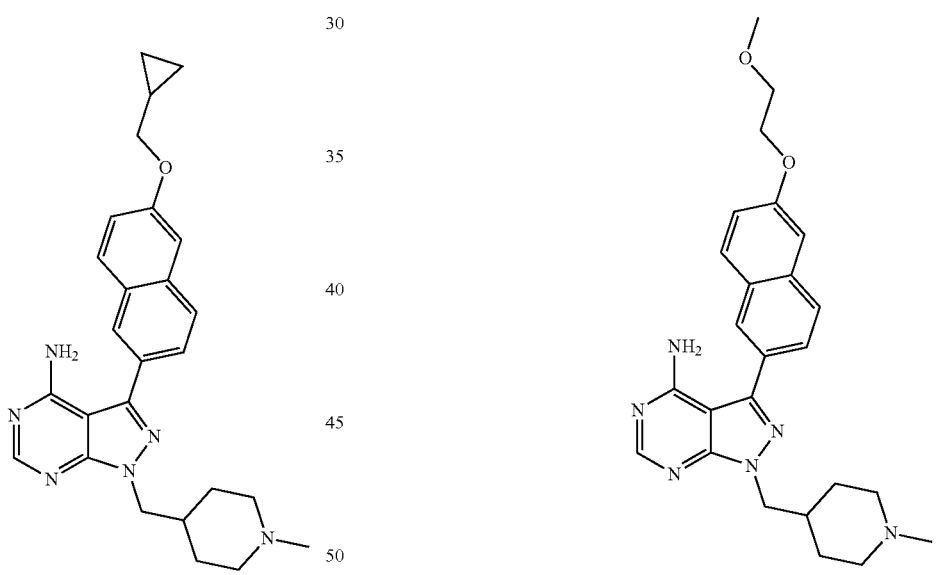

Tert-butyl 4-((4-amino-3-(6-hydroxynaphthalen-2-yl)-1H-pyrazolo[3,4-d]pyrimidin-1-yl)methyl)piperidine-1-carboxylate and bromomethoxyethane were subjected to the general naphthol alkylation procedure followed by the general boc-deprotection procedure and general reductive amination procedure in order to afford the product. $^1$H NMR (300 MHz, CD$_3$OD) δ 8.50 (s, 1H), 8.16 (s, 1H), 8.01 (d, J=7.8 Hz, 1H), 7.93 (d, J=8.5 Hz, 1H), 7.80 (d, J=8.3 Hz, 1H), 7.40 (s, 1H), 7.30 (d, J=7.8 Hz, 1H), 4.52 (d, J=4.2 Hz, 2H), 4.31 (m, 2H), 3.86 (m, 2H), 3.62 (m, 2H), 3.54 (s, 3H), 3.04 (m, 2H), 2.87 (s, 3H), 2.44 (m, 1H), 1.99 (m, 2H), 1.77 (m, 2H); MS (ESI) 447.5 m/z [MH+], C$_{25}$H$_{31}$N$_6$O$_2$ requires 447.5.

Example 12: 1-((1-Methylpiperidin-4-yl)methyl)-3-(6-(oxetan-3-yloxy)naphthalen-2-yl)-1H-pyrazolo[3,4-d]pyrimidin-4-amine

Example 13: 2-(6-(4-Amino-1-((1-methylpiperidin-4-yl)methyl)-1H-pyrazolo[3,4-d]pyrimidin-3-yl)naphthalen-2-yloxy)ethanol

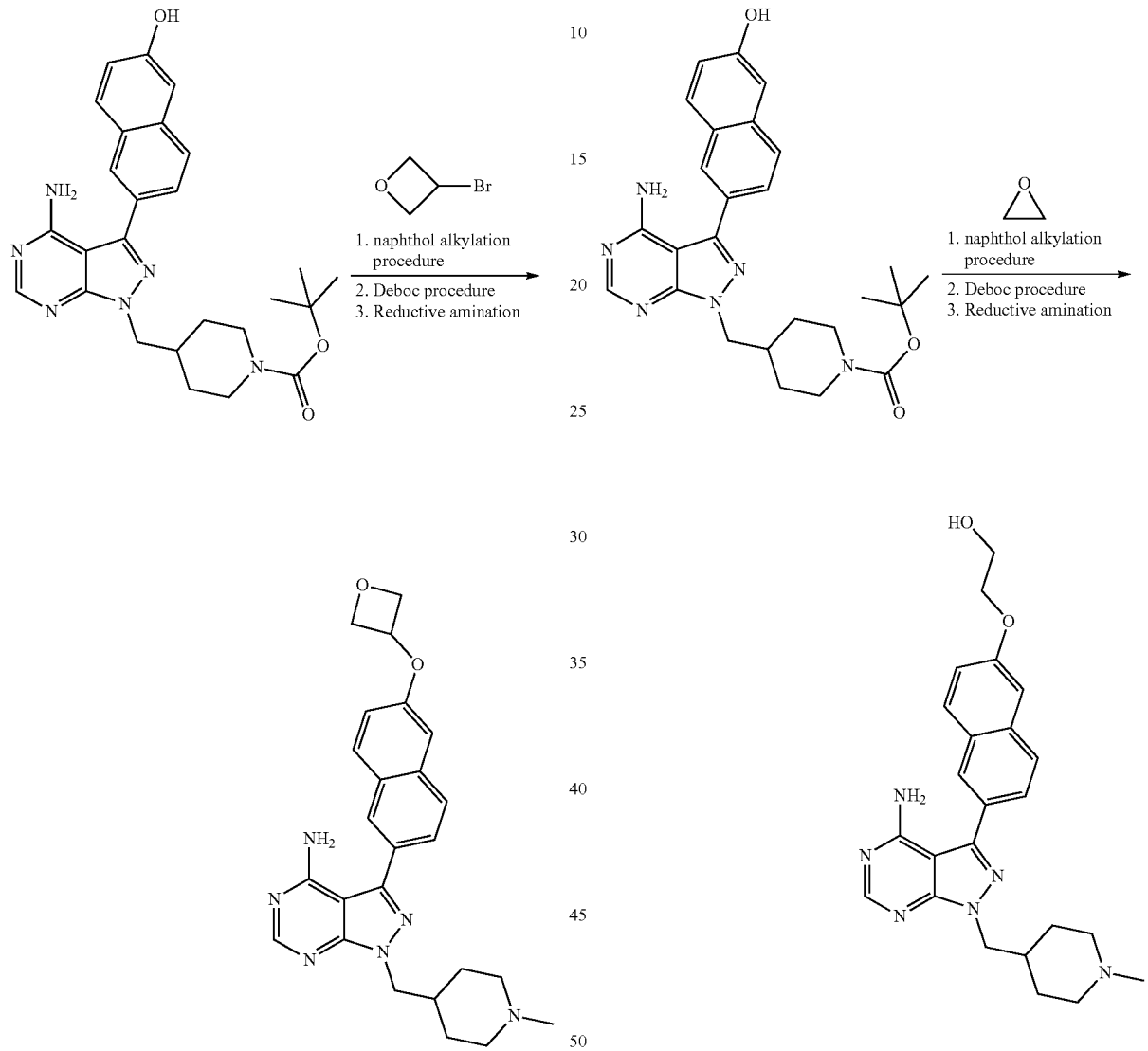

Tert-butyl4-((4-amino-3-(6-hydroxynaphthalen-2-yl)-1H-pyrazolo[3,4-d]pyrimidin-1-yl)methyl)piperidine-1-carboxylate and 3-bromooxetane were subjected to the general naphthol alkylation procedure followed by the general boc-deprotection procedure and general reductive amination procedure in order to afford the product. $^1$H NMR (300 MHz, CD$_3$OD) δ 8.49 (s, 1H), 8.18 (s, 1H), 8.06-7.92 (m, 2H), 7.82 (d, J=8.5 Hz, 1H), 7.51 (s, 1H), 7.36 (d, J=9.1 Hz, 1H), 4.81 (m, 1H), 4.53 (d, J=5.6 Hz, 2H), 3.99-3.84 (m, 4H), 3.57 (m, 2H), 3.05 (m, 2H), 2.86 (s, 3H), 2.44 (m, 1H), 2.00 (m, 2H), 1.74 (m, 2H); MS (ESI) 445.2 m/z [MH+], C$_{25}$H$_{29}$N$_6$O$_2$ requires 445.2.

Tert-butyl4-((4-amino-3-(6-hydroxynaphthalen-2-yl)-1H-pyrazolo[3,4-d]pyrimidin-1-yl)methyl)piperidine-1-carboxylate and oxirane were subjected to the general naphthol alkylation procedure followed by the general boc-deprotection procedure and general reductive amination procedure in order to afford the product. $^1$H NMR (300 MHz, CD$_3$OD) δ 8.50 (s, 1H), 8.17 (s, 1H), 8.02 (d, J=8.3 Hz, 1H), 7.94 (d, J=8.9 Hz, 1H), 7.80 (d, J=8.9 Hz, 1H), 7.41 (d, J=2.2 Hz, 1H), 7.34 (dd, J=8.7, 2.0 Hz, 1H), 4.53 (d, J=6.4 Hz, 2H), 4.25 (t, J=4.5 Hz, 2H), 3.99 (t, J=4.5 Hz, 2H), 3.56 (m, 2H), 3.04 (m, 2H), 2.86 (s, 3H), 2.44 (m, 1H), 2.00 (m, 2H), 1.72 (m, 2H); MS (ESI) 433.3 m/z [MH+], C$_{24}$H$_{29}$N$_6$O$_2$ requires 433.5.

Example 14: 1-(6-(4-Amino-1-((1-methylpiperidin-4-yl)methyl)-1H-pyrazolo[3,4-d]pyrimidin-3-yl)naphthalen-2-yloxy)-2-methylpropan-2-ol

Example 15: 3-(2-Ethoxyquinolin-6-yl)-1-((1-methylpiperidin-4-yl)methyl)-1H-pyrazolo[3,4-d]pyrimidin-4-amine

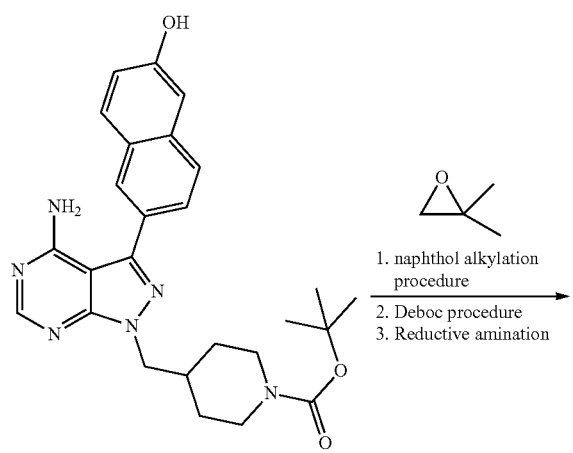

1. naphthol alkylation procedure
2. Deboc procedure
3. Reductive amination

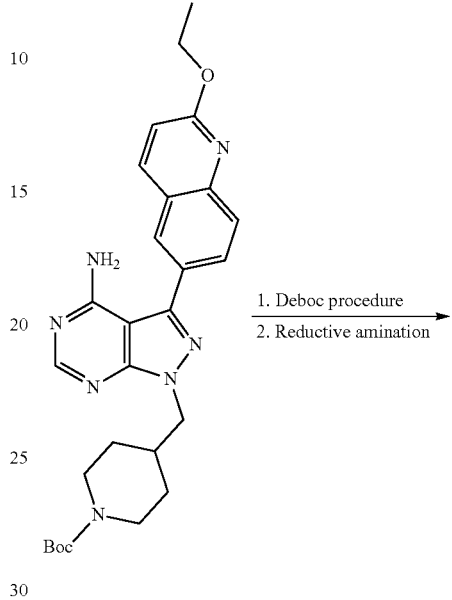

1. Deboc procedure
2. Reductive amination

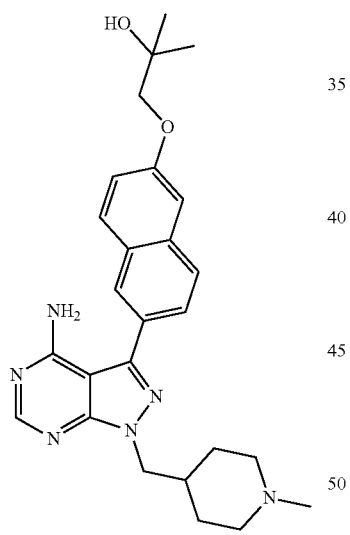

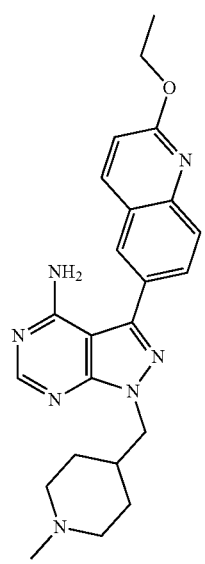

Tert-butyl4-((4-amino-3-(6-hydroxynaphthalen-2-yl)-1H-pyrazolo[3,4-d]pyrimidin-1-yl)methyl)piperidine-1-carboxylate and 2,2-dimethyloxirane were subjected to the general naphthol alkylation procedure followed by the general boc-deprotection procedure and general reductive amination procedure in order to afford the product. $^1$H NMR (300 MHz, CD$_3$OD) δ 8.48 (s, 1H), 8.17 (s, 1H), 8.02 (d, J=8.9 Hz, 1H), 7.94 (d, J=8.7 Hz, 1H), 7.79 (d, J=8.5 Hz, 1H), 7.43-7.32 (m, 2H), 4.53 (d, J=6.8 Hz, 2H), 3.98 (s, 2H), 3.56 (m, 2H), 3.04 (m, 2H), 2.87 (s, 3H), 2.44 (m, 1H), 2.00 (m, 2H), 1.77 (m, 2H), 1.41 (s, 6H); MS (ESI) 461.5 m/z [MH+], C$_{26}$H$_{33}$N$_6$O$_2$ requires 461.5.

Tert-butyl4-((4-amino-3-(2-ethoxyquinolin-6-yl)-1H-pyrazolo[3,4-d]pyrimidin-1-yl)methyl)piperidine-1-carboxylate was subjected to the general boc-deprotection procedure and general reductive amination procedure in order to afford the product. $^1$H NMR (300 MHz, CD$_3$OD) δ 8.29 (s, 1H), 8.22 (d, J=8.2 Hz, 1H), 8.12 (s, 1H), 7.98 (m, 2H), 7.04 (d, J=8.5 Hz, 1H), 4.55 (q, J=6.8 Hz, 2H), 4.38 (d, J=4.3 Hz, 2H), 2.95 (m, 2H), 2.30 (s, 3H), 2.99 (m, 2H), 1.67 (m, 2H), 1.48 (m, 4H); MS (ESI) 418.3 m/z [MH+], C$_{23}$H$_{28}$N$_7$O requires 418.5.

Example 16: 1-((1-Methylpiperidin-4-yl)methyl)-3-(2-(2,2,2-trifluoroethoxy)quinolin-6-yl)-1H-pyrazolo[3,4-d]pyrimidin-4-amine

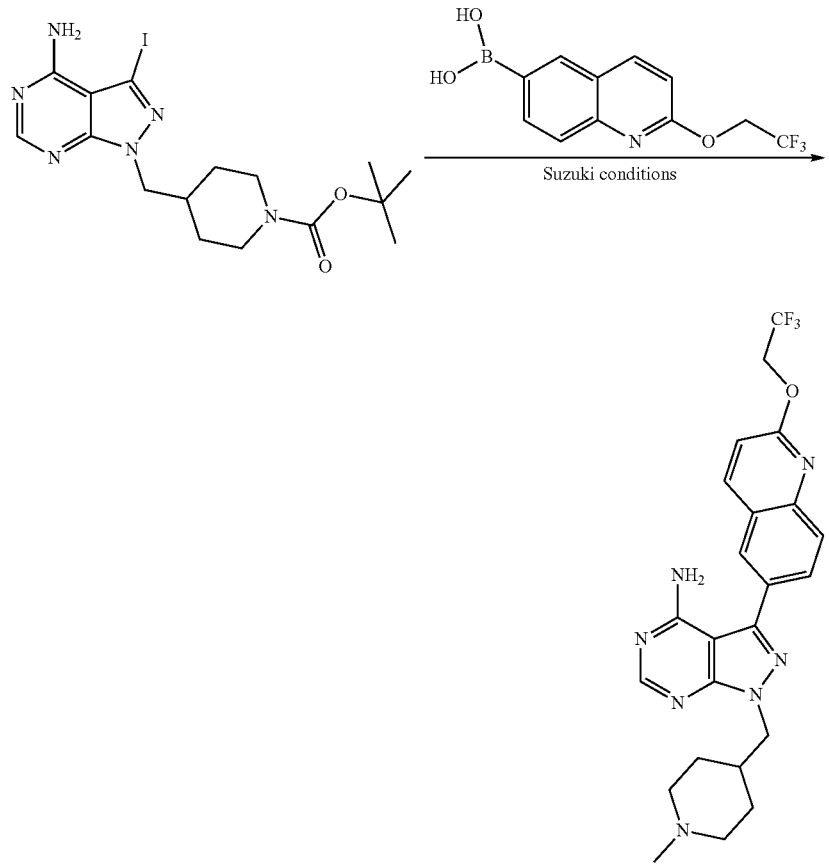 [SMILES: CC(C)(C)OC(=O)N1CCC(Cn2nc(I)c3c(N)ncnc32)CC1 ; OB(O)c1ccc2nc(OCC(F)(F)F)ccc2c1 ; CN1CCC(Cn2nc(-c3ccc4nc(OCC(F)(F)F)ccc4c3)c3c(N)ncnc32)CC1]

2-(2,2,2-Trifluoroethoxy)quinolin-6-ylboronic acid and tert-butyl 4-((4-amino-3-iodo-1H-pyrazolo[3,4-d]pyrimidin-1-yl)methyl)piperidine-1-carboxylate were subjected to the general Suzuki coupling procedure followed by the general boc-deprotection procedure and general reductive amination procedure in order to afford the product. $^1$H NMR (300 MHz, CD$_3$OD) δ 8.49 (s, 1H), 8.39 (d, J=8.5 Hz, 1H), 8.24 (s, 1H), 8.04 (s, 2H), 7.18 (d, J=7.0 Hz, 1H), 5.09 (q, J=8.7 Hz, 2H), 4.52 (s, 2H), 3.54 (m, 2H), 3.04 (m, 2H), 2.84 (s, 3H), 2.45 (m, 1H), 1.98 (m, 2H), 1.75 (m, 2H); MS (ESI) 472.2 m/z [MH+], C$_{23}$H$_{25}$F$_3$N$_7$O requires 472.5.

Example 17: 3-(6-ethoxynaphthalen-2-yl)-1-isobutyl-1H-pyrazolo[3,4-d]pyrimidin-4-amine

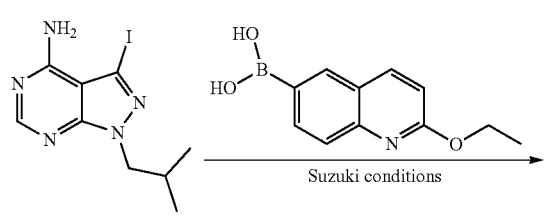

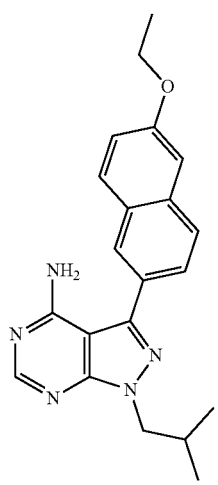

6-ethoxynaphthalen-2-ylboronic acid and 3-iodo-1-isobutyl-1H-pyrazolo[3,4-d]pyrimidin-4-amine were subjected to the general Suzuki coupling procedure in order to afford the product. $^1$H NMR (300 MHz, CD$_3$OD) δ 8.27 (s, 1H), 8.09 (s, 1H), 7.96 (d, J=8.1 Hz, 1H), 7.89 (d, J=9.1 Hz, 1H), 7.75 (dd, J=8.2, 2.0 Hz, 1H), 7.32 (s, 1H), 7.22 (dd, J=9.1, 2.4 Hz, 1H), 4.28-4.17 (m, 4H), 2.39 (m, 1H), 1.48 (t, J=6.8 Hz, 3H), 0.96 (d, J=6.6 Hz, 6H); MS (ESI) 362.4 m/z [MH+], C$_{21}$H$_{24}$N$_5$O requires 362.2.

Example 18: 3-(2-Cyclopropoxyquinolin-6-yl)-1-isobutyl-1H-pyrazolo[3,4-d]pyrimidin-4-amine

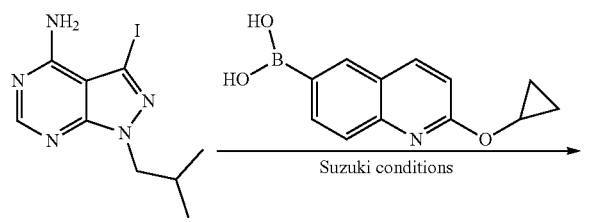

2-Cyclopropoxyquinolin-6-ylboronic acid and 3-iodo-1-isobutyl-1H-pyrazolo[3,4-d]pyrimidin-4-amine were subjected to the general Suzuki coupling procedure in order to afford the product. $^1$H NMR (300 MHz, CD$_3$OD) δ 8.25 (s, 1H), 8.23 (d, J=8.9 Hz, 1H), 8.10 (s, 1H), 8.00-7.91 (m, 2H), 7.02 (d, J=8.7 Hz, 1H), 4.46 (s, 1H), 4.22 (d, J=7.4 Hz, 2H), 2.36 (m, 1H), 0.96 (d, J=6.6 Hz, 6H), 0.91-0.72 (m, 4H); MS (ESI) 375.4 m/z [MH+], C$_{21}$H$_{23}$N$_6$O requires 375.4.

Example 19: 3-(4-Amino-3-(2-cyclopropoxyquinolin-6-yl)-1H-pyrazolo[3,4-d]pyrimidin-1-yl)-2,2-dimethylpropan-1-ol

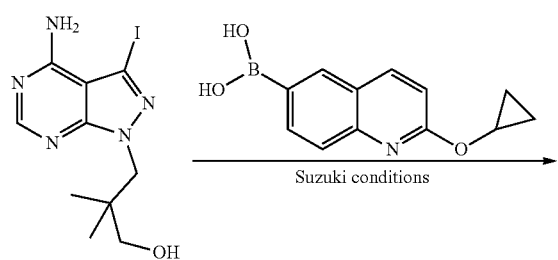

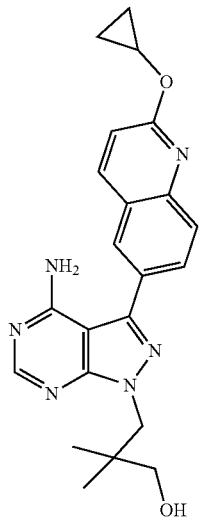

2-Cyclopropoxyquinolin-6-ylboronic acid and previously reported 3-(4-amino-3-iodo-1H-pyrazolo[3,4-d]pyrimidin-1-yl)-2,2-dimethylpropan-1-ol were subjected to the general Suzuki coupling procedure in order to afford the product. $^1$H NMR (300 MHz, CD$_3$OD) δ 8.65 (s, 1H), 8.50 (s, 1H), 8.36 (m, 1H), 8.21-8.05 (m, 2H), 7.51 (d, J=8.3 Hz, 1H), 4.59 (s, 2H), 4.47 (s, 2H), 4.46 (m, 1H), 1.01 (s, 6H), 0.70 (m, 4H); MS (ESI) 405.2 m/z [MH+], C$_{22}$H$_{25}$N$_6$O$_2$ requires 405.4.

Example 20: 3-(2-Cyclopropoxyquinolin-6-yl)-1-((3-methyloxetan-3-yl)methyl)-1H-pyrazolo[3,4-d]pyrimidin-4-amine

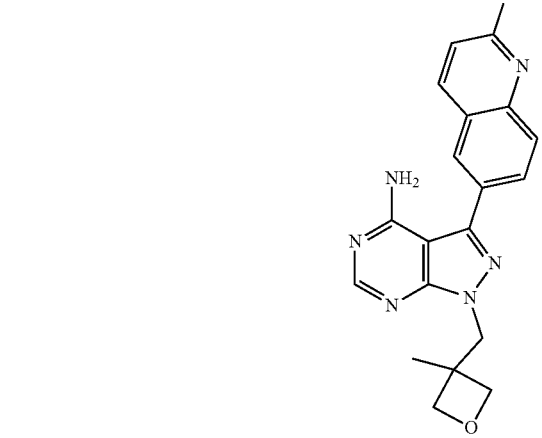

2-Cyclopropoxyquinolin-6-ylboronic acid and 3-iodo-1-((3-methyloxetan-3-yl)methyl)-1H-pyrazolo[3,4-d]pyrimidin-4-amine were subjected to the general Suzuki coupling procedure in order to afford the product. $^1$H NMR (300 MHz, CDCl$_3$) δ 8.41 (s, 1H), 8.12-8.01 (m, 3H), 7.96 (d, J=8.3 Hz, 1H), 6.97 (d, J=8.0 Hz, 1H), 5.54 (s, 2H), 4.91 (d, J=6.1 Hz, 2H), 4.64 (s, 2H), 4.56 (m, 1H), 4.45 (d, J=6.1 Hz, 2H), 1.36 (s, 3H), 0.95-0.82 (m, 4H); MS (ESI) 403.2 m/z [MH+], C$_{22}$H$_{23}$N$_6$O$_2$ requires 403.4.

Example 21: 3-(6-Cyclopropoxynaphthalen-2-yl)-1-((tetrahydro-2H-pyran-4-yl)methyl)-1H-pyrazolo[3,4-d]pyrimidin-4-amine

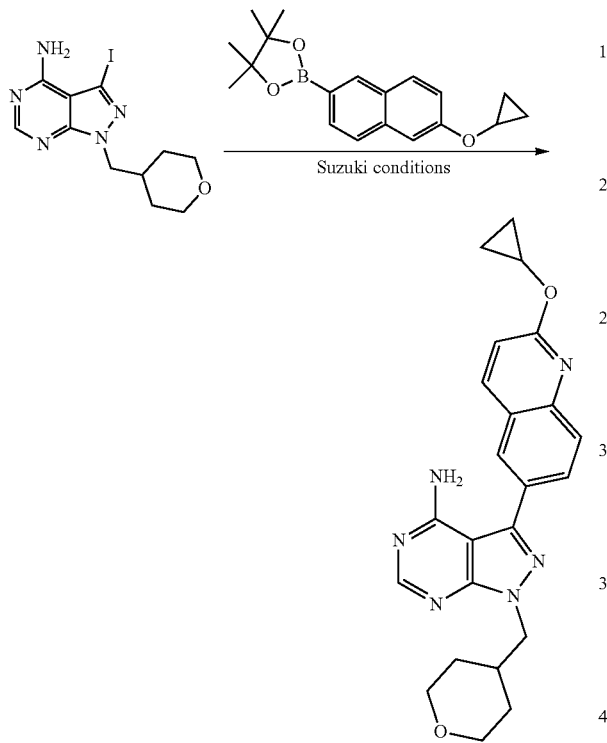

2-(6-Cyclopropoxynaphthalen-2-yl)-4,4,5,5-tetramethyl-1,3,2-dioxaborolane and 3-iodo-1-((tetrahydro-2H-pyran-4-yl)methyl)-1H-pyrazolo[3,4-d]pyrimidin-4-amine were subjected to the general Suzuki coupling procedure in order to afford the product. $^1$H NMR (300 MHz, CD$_3$OD) δ 8.47 (s, 1H), 8.16 (s, 1H), 8.03 (d, J=8.2 Hz, 1H), 7.92 (d, J=9.1 Hz, 1H), 7.78 (d, J=8.2 Hz, 1H), 7.64 (s, 1H), 7.27 (dd, J=9.1, 2.2 Hz, 1H) 4.45 (d, J=6.8 Hz, 2H), 3.99 (m, 1H), 3.76 (m, 2H), 3.05 (m, 2H), 2.40 (m, 1H), 1.61 (m, 2H), 1.46 (m, 2H), 0.93-0.80 (m, 4H); MS (ESI) 416.4 m/z [MH+], C$_{24}$H$_{25}$N$_5$O$_2$ requires 416.4.

Example 22: 3-(2-Cyclopropoxyquinolin-6-yl)-1-((tetrahydro-2H-pyran-4-yl)methyl)-1H-pyrazolo[3,4-d]pyrimidin-4-amine

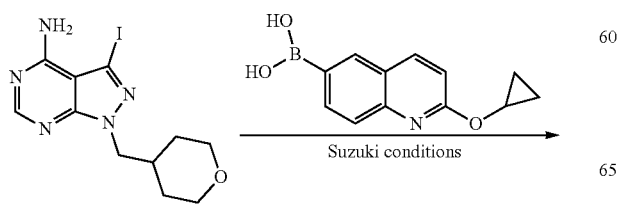

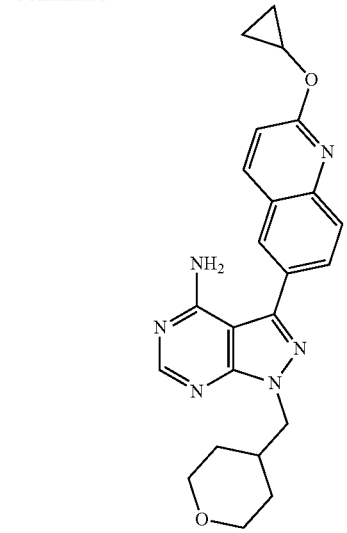

2-cyclopropoxyquinolin-6-ylboronic acid and 3-iodo-1-((tetrahydro-2H-pyran-4-yl)methyl)-1H-pyrazolo[3,4-d]pyrimidin-4-amine were subjected to the general Suzuki coupling procedure in order to afford the product. $^1$H NMR (300 MHz, CD$_3$OD) δ 8.31 (s, 1H), 8.22 (d, J=8.9 Hz, 1H), 8.12 (d, J=1.8 Hz, 1H), 8.06 (d, J=8.7 Hz, 1H), 8.00 (dd, J=8.5, 1.2 Hz, 1H), 7.07 (d, J=8.9 Hz, 1H), 4.47 (m, 1H) 4.36 (d, J=7.2 Hz, 2H), 3.98 (m, 2H), 3.42 (m, 2H), 2.34 (m, 1H), 1.59 (m, 2H), 1.49 (m, 2H), 0.93-0.83 (m, 4H); MS (ESI) 416.4 m/z [MH+], C$_{23}$H$_{24}$N$_6$O$_2$ requires 416.4.

Example 23: 1-(4-amino-3-(2-ethoxyquinolin-6-yl)-1H-pyrazolo[3,4-d]pyrimidin-1-yl)-2-methylpropan-2-ol

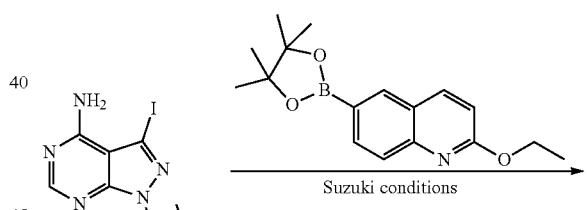

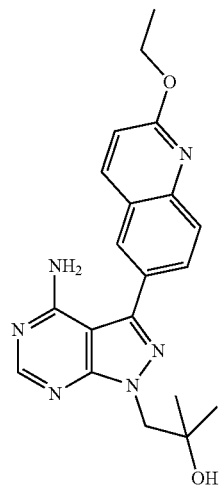

2-ethoxy-6-(4,4,5,5-tetramethyl-1,3,2-dioxaborolan-2-yl) quinoline and 1-(4-amino-3-iodo-1H-pyrazolo[3,4-d]pyrimidin-1-yl)-2-methylpropan-2-ol were subjected to the general Suzuki coupling procedure to afford compound the product. ¹H NMR (300 MHz, CD₃OD) δ 8.69 (d, J=9.1 Hz, 1H), 8.45 (s, 1H), 8.34 (s, 1H), 8.17 (d, J=8.0 Hz, 1H), 8.04 (d, J=7.4 Hz, 1H), 7.45 (d, J=7.4 Hz, 1H), 4.67 (q, J=6.0 Hz, 2H), 4.50 (s, 2H), 1.54 (t, J=6.5 Hz, 3H), 1.31 (s, 6H). MS (ESI) 379.2 m/z [MH+], $C_{20}H_{23}N_6O_2$ requires 379.1.

Example 24: 1-(4-Amino-3-(6-cyclopropoxynaphthalen-2-yl)-1H-pyrazolo[3,4-d]pyrimidin-1-yl)-2-methylpropan-2-ol

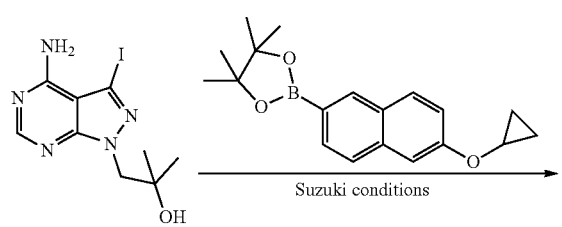

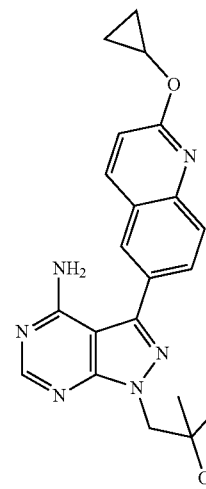

2-(6-Cyclopropoxynaphthalen-2-yl)-4,4,5,5-tetramethyl-1,3,2-dioxaborolane and 1-(4-amino-3-iodo-1H-pyrazolo[3,4-d]pyrimidin-1-yl)-2-methylpropan-2-ol were subjected to the general Suzuki coupling procedure to afford title compound the product; ¹H NMR (500 MHz, CD₃OD) δ 8.26 (s, 1H), 8.08 (s, 1H), 7.93 (d, J=8.4 Hz, 1H), 7.85 (d, J=8.81 Hz, 1H), 7.76 (d, J=8.4 Hz, 1H), 7.57 (s, 1H), 7.20 (dd, J=8.8, 1.8 Hz, 1H), 4.40 (s, 2H), 3.91 (m, 1H), 1.27 (s, 6H), 0.88 (m, 2H), 0.78 (m, 2H). MS (ESI) 390.2 m/z [MH+], $C_{22}H_{24}N_5O_2$ requires 390.1.

Example 25: 1-(4-Amino-3-(2-cyclopropoxyquinolin-6-yl)-1H-pyrazolo[3,4-d]pyrimidin-1-yl)-2-methylpropan-2-ol

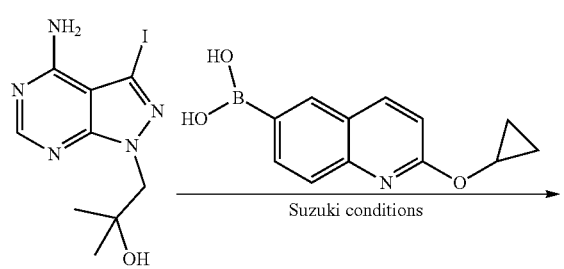

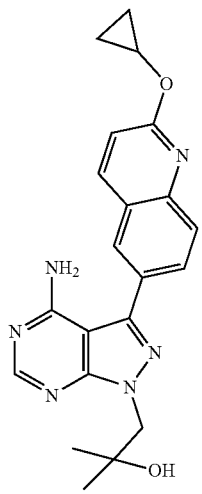

2-Cyclopropoxyquinolin-6-ylboronic acid and 1-(4-amino-3-iodo-1H-pyrazolo[3,4-d]pyrimidin-1-yl)-2-methylpropan-2-ol were subjected to the general Suzuki coupling procedure in order to afford the product. NMR (300 MHz, CD₃OD) δ8.28 (s, 1H), 8.28-8.24 (d, J=8.9 Hz, 1H), 8.15 (t, J=1.4 Hz, 1H), 8.01 (d, J=1.2 Hz, 2H), 7.06 (d, J=8.7 Hz, 1H), 4.53-4.45 (m, 1H), 4.42 (s, 2H), 1.28 (s, 6H), 0.92-0.85 (m, 2H), 0.85-0.77 (m, 2H); MS (ESI) 391.1 m/z [MH⁺], $C_{21}H_{23}N_6O_2$ requires 391.2.

Example 26: 3-(4-Amino-3-(6-cyclopropoxynaphthalen-2-yl)-1H-pyrazolo[3,4-d]pyrimidin-1-yl)-2,2-dimethylpropan-1-ol

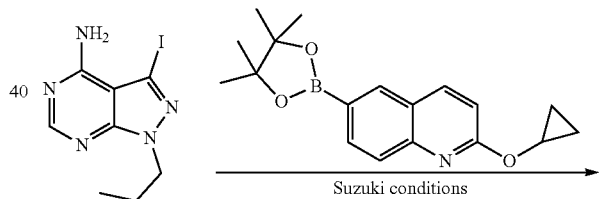

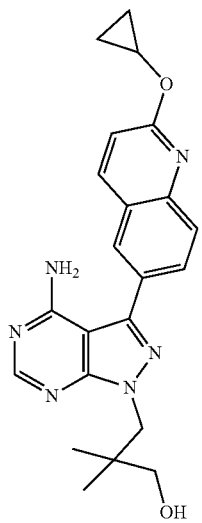

2-(6-Cyclopropoxynaphthalen-2-yl)-4,4,5,5-tetramethyl-1,3,2-dioxaborolane and previously reported 3-(4-amino-3-iodo-1H-pyrazolo[3,4-d]pyrimidin-1-yl)-2,2-dimethylpropan-1-ol were subjected to the general Suzuki coupling procedure in order to afford the product. $^1$H NMR (300 MHz, CD$_3$OD) δ 8.30 (s, 1H), 8.12 (s, 1H), 8.00 (d, J=8.7 Hz, 1H), 7.90 (d, J=8.9 Hz, 1H), 7.78 (dd, J=8.2, 1.5 Hz, 1H), 7.62 (d, J=2.4, 1H), 7.24 (dd, J=9.1, 2.4 Hz, 1H), 4.33 (s, 2H), 3.97 (m, 1H), 3.32 (s, 2H), 1.22 (s, 6H), 0.94-0.81 (m, 4H); MS (ESI) 404.5 m/z [MH+], C$_{23}$H$_{26}$N$_5$O$_2$ requires 404.4.

Examples 27-130

The following compounds were prepared by the methods disclosed herein:

| Ex. No. | Compound |
|---|---|
| 27 | 6-(4-amino-1-(piperidin-4-ylmethyl)-1H-pyrazolo[3,4-d]pyrimidin-3-yl)-N,N-dimethylquinolin-2-amine; |
| 28 | 3-tert-butyl-1-(6-ethoxynaphthalen-2-yl)imidazo[1,5-a]pyrazin-8-amine; |
| 29 | 3-tert-butyl-1-(6-methoxynaphthalen-2-yl)imidazo[1,5-a]pyrazin-8-amine; |
| 30 | 3-(2-methoxyquinolin-6-yl)-1-((tetrahydro-2H-pyran-4-yl)methyl)-1H-pyrazolo[3,4-d]pyrimidin-4-amine |
| 31 | 3-(2-(cyclopropylmethoxy)quinolin-6-yl)-1-((tetrahydro-2H-pyran-4-yl)methyl)-1H-pyrazolo[3,4-d]pyrimidin-4-amine |
| 32 | 3-(6-(cyclopropylmethoxy)naphthalen-2-yl)-1-((tetrahydro-2H-pyran-4-yl)methyl)-1H-pyrazolo[3,4-d]pyrimidin-4-amine |
| 33 | 3-(6-cyclobutoxynaphthalen-2-yl)-1-((tetrahydro-2H-pyran-4-yl)methyl)-1H-pyrazolo[3,4-d]pyrimidin-4-amine |
| 34 | 3-(6-(oxetan-3-yloxy)naphthalen-2-yl)-1-((tetrahydro-2H-pyran-4-yl)methyl)-1H-pyrazolo[3,4-d]pyrimidin-4-amine |
| 35 | 3-(4-amino-3-(6-ethoxynaphthalen-2-yl)-1H-pyrazolo[3,4-d]pyrimidin-1-yl)-2,2-dimethylpropan-1-ol |
| 36 | 1-(6-(4-amino-1-isobutyl-1H-pyrazolo[3,4-d]pyrimidin-3-yl)naphthalen-2-yloxy)-2-methylpropan-2-ol |
| 37 | 2-(6-(4-amino-1-isobutyl-1H-pyrazolo[3,4-d]pyrimidin-3-yl)naphthalen-2-yloxy)ethanol |
| 38 | 1-isobutyl-3-(6-(oxetan-3-yloxy)naphthalen-2-yl)-1H-pyrazolo[3,4-d]pyrimidin-4-amine |
| 39 | 1-isobutyl-3-(6-(2-methoxyethoxy)naphthalen-2-yl)-1H-pyrazolo[3,4-d]pyrimidin-4-amine |
| 40 | 3-(4-amino-3-(2-ethoxyquinolin-6-yl)-1H-pyrazolo[3,4-d]pyrimidin-1-yl)-2,2-dimethylpropan-1-ol |
| 41 | 3-(2-(2-methoxyethoxy)quinolin-6-yl)-1-neopentyl-1H-pyrazolo[3,4-d]pyrimidin-4-amine |
| 42 | 3-(2-cyclopropoxyquinolin-6-yl)-1-(piperidin-4-ylmethyl)-1H-pyrazolo[3,4-d]pyrimidin-4-amine |
| 43 | 1-(azetidin-3-ylmethyl)-3-(2-cyclopropoxyquinolin-6-yl)-1H-pyrazolo[3,4-d]pyrimidin-4-amine |
| 44 | 3-(2-cyclopropoxyquinolin-6-yl)-1-((1-methylazetidin-3-yl)methyl)-1H-pyrazolo[3,4-d]pyrimidin-4-amine |
| 45 | 3-(2-(2-methoxyethoxy)quinolin-6-yl)-1-((1-methylpiperidin-4-yl)methyl)-1H-pyrazolo[3,4-d]pyrimidin-4-amine |
| 46 | 1-isobutyl-3-(2-(2,2,2-trifluoroethoxy)quinolin-6-yl)-1H-pyrazolo[3,4-d]pyrimidin-4-amine |
| 47 | 1-(piperidin-4-ylmethyl)-3-(2-(2,2,2-trifluoroethoxy)quinolin-6-yl)-1H-pyrazolo[3,4-d]pyrimidin-4-amine |
| 48 | 2-(3-(4-amino-3-(2-cyclopropoxyquinolin-6-yl)-1H-pyrazolo[3,4-d]pyrimidin-1-yl)-2,2-dimethylpropoxy)ethanol |
| 49 | 1-(4-amino-3-(2-(2,2,2-trifluoroethoxy)quinolin-6-yl)-1H-pyrazolo[3,4-d]pyrimidin-1-yl)-2-methylpropan-2-ol |
| 50 | 3-(7-ethoxynaphthalen-2-yl)-1-isobutyl-1H-pyrazolo[3,4-d]pyrimidin-4-amine |
| 51 | 3-(7-ethoxynaphthalen-2-yl)-1-(piperidin-4-ylmethyl)-1H-pyrazolo[3,4-d]pyrimidin-4-amine |
| 52 | 3-(6-ethoxynaphthalen-2-yl)-1-((3-methyloxetan-3-yl)methyl)-1H-pyrazolo[3,4-d]pyrimidin-4-amine |
| 53 | 2-(4-amino-3-(6-ethoxynaphthalen-2-yl)-1H-pyrazolo[3,4-d]pyrimidin-1-yl)-1-morpholinoethanone |
| 54 | 2-(4-amino-3-(6-cyclopropoxynaphthalen-2-yl)-1H-pyrazolo[3,4-d]pyrimidin-1-yl)-1-morpholinoethanone |
| 55 | 2-((4-amino-3-(6-(methoxymethyl)naphthalen-2-yl)-1H-pyrazolo[3,4-d]pyrimidin-1-yl)methyl)-1,1,1,3,3,3-hexafluoropropan-2-ol |
| 56 | 2-((4-amino-3-(2-cyclopropoxyquinolin-6-yl)-1H-pyrazolo[3,4-d]pyrimidin-1-yl)methyl)-1,1,1,3,3,3-hexafluoropropan-2-ol |
| 57 | 1-(3-(6-cyclopropoxynaphthalen-2-yl)-1H-pyrrolo[3,2-c]pyridin-1-yl)-2-methylpropan-2-ol |
| 58 | 1-(4-amino-5-(2-cyclopropoxyquinolin-6-yl)-7H-pyrrolo[2,3-d]pyrimidin-7-yl)-2-methylpropan-2-ol |
| 59 | 4-(4-amino-3-(2-cyclopropoxyquinolin-6-yl)-1H-pyrazolo[3,4-d]pyrimidin-1-yl)-2,3,3-trimethylbutan-2-ol |
| 60 | 1-((4-amino-3-(2-cyclopropoxyquinolin-6-yl)-1H-pyrazolo[3,4-d]pyrimidin-1-yl)methyl)cyclobutanol |
| 61 | 1-(4-amino-5-(6-cyclopropoxynaphthalen-2-yl)-7H-pyrrolo[2,3-d]pyrimidin-7-yl)-2-methylpropan-2-ol |

| Ex. No. | Compound |
|---|---|
| 62 | 1-((4-amino-3-(6-cyclopropoxynaphthalen-2-yl)-1H-pyrazolo[3,4-d]pyrimidin-1-yl)methyl)cyclobutanol |
| 63 | 1-((4-amino-3-(2-cyclopropoxyquinolin-6-yl)-1H-pyrazolo[3,4-d]pyrimidin-1-yl)methyl)cyclopentanol |
| 64 | 1-((4-amino-3-(6-cyclopropoxynaphthalen-2-yl)-1H-pyrazolo[3,4-d]pyrimidin-1-yl)methyl)cyclopentanol |
| 65 | 4-((4-amino-3-(2-cyclopropoxyquinolin-6-yl)-1H-pyrazolo[3,4-d]pyrimidin-1-yl)methyl)-tetrahydro-2H-pyran-4-ol |
| 66 | 4-((4-amino-3-(6-cyclopropoxynaphthalen-2-yl)-1H-pyrazolo[3,4-d]pyrimidin-1-yl)methyl)-tetrahydro-2H-pyran-4-ol |
| 67 | (3-((4-amino-3-(2-cyclopropoxyquinolin-6-yl)-1H-pyrazolo[3,4-d]pyrimidin-1-yl)methyl)oxetan-3-yl)methanol |
| 68 | (3-((4-amino-3-(6-cyclopropoxynaphthalen-2-yl)-1H-pyrazolo[3,4-d]pyrimidin-1-yl)methyl)oxetan-3-yl)methanol |
| 69 | 3-(6-cyclopropoxynaphthalen-2-yl)-1-(2-methoxy-2-methylpropyl)-1H-pyrazolo[3,4-d]pyrimidin-4-amine |
| 70 | 3-(2-cyclopropoxyquinolin-6-yl)-1-(2-methoxy-2-methylpropyl)-1H-pyrazolo[3,4-d]pyrimidin-4-amine |
| 71 | methyl 3-(4-amino-3-(6-cyclopropoxynaphthalen-2-yl)-1H-pyrazolo[3,4-d]pyrimidin-1-yl)-2,2-dimethylpropanoate |
| 72 | methyl 3-(4-amino-3-(2-cyclopropoxyquinolin-6-yl)-1H-pyrazolo[3,4-d]pyrimidin-1-yl)-2,2-dimethylpropanoate |
| 73 | 4-((4-amino-3-(6-ethoxynaphthalen-2-yl)-1H-pyrazolo[3,4-d]pyrimidin-1-yl)methyl)piperidin-4-ol |
| 74 | 4-((4-amino-3-(6-ethoxynaphthalen-2-yl)-1H-pyrazolo[3,4-d]pyrimidin-1-ylmethyl)1H-methylpiperidin-4-ol |
| 75 | methyl 2-((6-(4-amino-1-((1-methylpiperidin-4-yl)methyl)-1H-pyrazolo[3,4-d]pyrimidin-3-yl)naphthalen-2-yl)oxy)acetate |
| 76 | 2-((6-(4-amino-1-((1-methylpiperidin-4-yl)methyl)-1H-pyrazolo[3,4-d]pyrimidin-3-yl)naphthalen-2-yl)oxy)acetonitrile |
| 77 | 4-((4-amino-3-(6-ethoxynaphthalen-2-yl)-1H-pyrazolo[3,4-d]pyrimidin-1-yl)methyl)piperidine-4-carbonitrile |
| 78 | 4-((4-amino-3-(6-ethoxynaphthalen-2-yl)-1H-pyrazolo[3,4-d]pyrimidin-1-ylmethyl)1H-methylpiperidine-4-carbonitrile |
| 79 | 3-(4-amino-3-(6-cyclopropoxynaphthalen-2-yl)-1H-pyrazolo[3,4-d]pyrimidin-1-yl)-2,2-dimethylpropanoic acid |
| 80 | 3-(6-cyclopropoxynaphthalen-2-yl)-1-(2-fluoro-2-methylpropyl)-1H-pyrazolo[3,4-d]pyrimidin-4-amine |
| 81 | 4-((4-amino-3-(6-cyclopropoxynaphthalen-2-yl)-1H-pyrazolo[3,4-d]pyrimidin-1-yl)methyl)piperidin-4-ol |
| 82 | 4-((4-amino-3-(6-cyclopropoxynaphthalen-2-yl)-1H-pyrazolo[3,4-d]pyrimidin-1-ylmethyl)1H-methylpiperidin-4-ol |
| 83 | 4-((4-amino-3-(2-ethoxyquinolin-6-yl)-1H-pyrazolo[3,4-d]pyrimidin-1-yl)methyl)-1-methylpiperidin-4-ol |
| 84 | 4-((4-amino-3-(2-ethoxyquinolin-6-yl)-1H-pyrazolo[3,4-d]pyrimidin-1-yl)methyl)-1-methylpiperidin-4-ol |
| 85 | 4-((4-amino-3-(2-cyclopropoxyquinolin-6-yl)-1H-pyrazolo[3,4-d]pyrimidin-1-yl)methyl)piperidin-4-ol |
| 86 | 4-((4-amino-3-(6-cyclopropoxynaphthalen-2-yl)-1H-pyrazolo[3,4-d]pyrimidin-1-ylmethyl)1H-methylpiperidine-4-carbonitrile |
| 87 | 4-((4-amino-3-(2-ethoxyquinolin-6-yl)-1H-pyrazolo[3,4-d]pyrimidin-1-yl)methyl)piperidin-4-ol |
| 88 | 4-((4-amino-3-(2-cyclopropoxyquinolin-6-yl)-1H-pyrazolo[3,4-d]pyrimidin-1-ylmethyl)1H-methylpiperidin-4-ol |
| 89 | 4-((4-amino-3-(2-ethoxyquinolin-6-yl)-1H-pyrazolo[3,4-d]pyrimidin-1-yl)methyl)piperidine-4-carbonitrile |
| 90 | 4-((4-amino-3-(2-ethoxyquinolin-6-yl)-1H-pyrazolo[3,4-d]pyrimidin-1-yl)methyl)-1-methylpiperidine-4-carbonitrile |
| 91 | 2-(6-(4-amino-1-(2-hydroxy-2-methylpropyl)-1H-pyrazolo[3,4-d]pyrimidin-3-yl)naphthalen-2-yloxy)acetonitrile |
| 92 | methyl 2-(6-(4-amino-1-(piperidin-4-ylmethyl)-1H-pyrazolo[3,4-d]pyrimidin-3-yl)quinolin-2-yloxy)acetate |
| 93 | 3-((4-amino-3-(6-cyclopropoxynaphthalen-2-yl)-1H-pyrazolo[3,4-d]pyrimidin-1-yl)methyl)azetidin-3-ol |
| 94 | 3-((4-amino-3-(6-cyclopropoxynaphthalen-2-yl)-1H-pyrazolo[3,4-d]pyrimidin-1-yl)methyl)-1-methylazetidin-3-ol |
| 95 | 4-((4-amino-3-(2-cyclopropoxyquinolin-6-yl)-1H-pyrazolo[3,4-d]pyrimidin-1-ylmethyl)-1-methylpiperidine-4-carbonitrile |
| 96 | 3-((4-amino-3-(2-ethoxyquinolin-6-yl)-1H-pyrazolo[3,4-d]pyrimidin-1-yl)methyl)azetidin-3-ol |
| 97 | 3-(6-(difluoromethoxy)naphthalen-2-yl)-1-(piperidin-4-ylmethyl)-1H-pyrazolo[3,4-d]pyrimidin-4-amine |
| 98 | 3-(6-(difluoromethoxy)naphthalen-2-yl)-1-((1-methylpiperidin-4-yl)methyl)-1H-pyrazolo[3,4-d]pyrimidin-4-amine |
| 99 | 3-((4-amino-3-(6-ethoxynaphthalen-2-yl)-1H-pyrazolo[3,4-d]pyrimidin-1-yl)methyl)azetidin-3-ol |

-continued

| Ex. No. | Compound |
|---|---|
| 100 | 3-((4-amino-3-(6-ethoxynaphthalen-2-yl)-1H-pyrazolo[3,4-d]pyrimidin-1-yl)methyl)-1-methylazetidin-3-ol |
| 101 | 4-((4-amino-3-(6-(difluoromethoxy)naphthalen-2-yl)-1H-pyrazolo[3,4-d]pyrimidin-1-yl)methyl)piperidin-4-ol |
| 102 | 4-((4-amino-3-(6-(difluoromethoxy)naphthalen-2-yl)-1H-pyrazolo[3,4-d]pyrimidin-1-yl)methyl)-1-methylpiperidin-4-ol |
| 103 | 4-((4-amino-3-(6-(difluoromethoxy)naphthalen-2-yl)-1H-pyrazolo[3,4-d]pyrimidin-1-yl)methyl)piperidine-4-carbonitrile |
| 104 | 3-((4-amino-3-(2-cyclopropoxyquinolin-6-yl)-1H-pyrazolo[3,4-d]pyrimidin-1-yl)methyl)azetidin-3-ol |
| 105 | 4-((4-amino-3-(6-(difluoromethoxy)naphthalen-2-yl)-1H-pyrazolo[3,4-d]pyrimidin-1-yl)methyl)-1-methylpiperidine-4-carbonitrile |
| 106 | 3-((4-amino-3-(2-cyclopropoxyquinolin-6-yl)-1H-pyrazolo[3,4-d]pyrimidin-1-yl)methyl)-1-methylazetidin-3-ol |
| 107 | 1-(3-(6-ethoxynaphthalen-2-yl)-1-((1-(methylcarbamoyl)piperidin-4-yl)methyl)-1H-pyrazolo[3,4-d]pyrimidin-4-yl)-3-methylurea |
| 108 | 4-((4-amino-3-(2-ethoxyquinolin-6-yl)-1H-pyrazolo[3,4-d]pyrimidin-1-yl)methyl)-N-methylpiperidine-1-carboxamide |
| 109 | 3-(6-ethoxynaphthalen-2-yl)-1-(1-ethylpiperidin-4-yl)-1H-pyrazolo[3,4-d]pyrimidin-4-amine |
| 110 | 3-(2-ethoxyquinolin-6-yl)-1-isopropyl-1H-pyrazolo[3,4-d]pyrimidin-4-amine |
| 111 | 3-(6-ethoxynaphthalen-2-yl)-1-(piperidin-4-yl)-1H-pyrazolo[3,4-d]pyrimidin-4-amine |
| 112 | 3-(6-ethoxynaphthalen-2-yl)-1-(1-methylpiperidin-4-yl)-1H-pyrazolo[3,4-d]pyrimidin-4-amine |
| 113 | 3-(6-ethoxynaphthalen-2-yl)-1-(2-(piperidin-4-yl)ethyl)-1H-pyrazolo[3,4-d]pyrimidin-4-amine |
| 114 | 3-(6-ethoxynaphthalen-2-yl)-1-(2-(1-methylpiperidin-4-yl)ethyl)-1H-pyrazolo[3,4-d]pyrimidin-4-amine |
| 115 | 3-(6-ethoxynaphthalen-2-yl)-1-(2-(1-ethylpiperidin-4-yl)ethyl)-1H-pyrazolo[3,4-d]pyrimidin-4-amine |
| 116 | 3-(6-ethoxynaphthalen-2-yl)-1-(2-(1-propylpiperidin-4-yl)ethyl)-1H-pyrazolo[3,4-d]pyrimidin-4-amine |
| 117 | 1-(2-(1-(3-aminopropyl)piperidin-4-yl)ethyl)-3-(6-ethoxynaphthalen-2-yl)-1H-pyrazolo[3,4-d]pyrimidin-4-amine |
| 118 | 3-(6-ethoxynaphthalen-2-yl)-1-(1-propylpiperidin-4-yl)-1H-pyrazolo[3,4-d]pyrimidin-4-amine |
| 119 | 1-(1-(3-aminopropyl)piperidin-4-yl)-3-(6-ethoxynaphthalen-2-yl)-1H-pyrazolo[3,4-d]pyrimidin-4-amine |
| 120 | 1-(6-ethoxynaphthalen-2-yl)-3-(piperidin-4-ylmethyl)imidazo[1,5-a]pyrazin-8-amine |
| 121 | 1-(6-ethoxynaphthalen-2-yl)-3-((1-methylpiperidin-4-yl)methyl)imidazo[1,5-a]pyrazin-8-amine |
| 122 | 1-isopropyl-3-(6-(oxetan-3-yloxy)naphthalen-2-yl)-1H-pyrazolo[3,4-d]pyrimidin-4-amine |
| 123 | 1-((6-(4-amino-1-isopropyl-1H-pyrazolo[3,4-d]pyrimidin-3-yl)naphthalen-2-yl)oxy)-2-methylpropan-2-ol |
| 124 | 2-((6-(4-amino-1-isopropyl-1H-pyrazolo[3,4-d]pyrimidin-3-yl)naphthalen-2-yl)oxy)ethan-1-ol |
| 125 | 3-(2-methoxyquinolin-6-yl)-1-((tetrahydro-2H-pyran-4-yl)methyl)-1H-pyrazolo[3,4-d]pyrimidin-4-amine |
| 126 | 3-(2-(cyclopropylmethoxy)quinolin-6-yl)-1-((tetrahydro-2H-pyran-4-yl)methyl)-1H-pyrazolo[3,4-d]pyrimidin-4-amine |
| 127 | 3-(2-ethoxyquinolin-6-yl)-1-(piperidin-4-ylmethyl)-1H-pyrazolo[3,4-d]pyrimidin-4-amine |
| 128 | 3-(6-ethoxynaphthalen-2-yl)-1-((1-methylpiperidin-4-yl)methyl)-1H-pyrazolo[3,4-d]pyrimidin-4-amine. |
| 129 | 1-(piperidin-4-ylmethyl)-3-(6-propoxynaphthalen-2-yl)-1H-pyrazolo[3,4-d]pyrimidin-4-amine |
| 130 | 3-(6-isopropoxynaphthalen-2-yl)-1-(piperidin-4-ylmethyl)-1H-pyrazolo[3,4-d]pyrimidin-4-amine |

Biological Example 1: Antitumor Activity

Anti-tumor activity was determined by screening a series of BKIs against the castrate-resistant, androgen-receptor-positive, prostate cancer cell line LNCaP95. This line is of special interest as it has been shown to be castration-resistant due to the generation of constitutively active AR splice variants, in particular AR-V7. In addition, the LNCaP cell line and its sublines express all three isoforms of PKD. Inhibition of proliferation was determined based on the level of LNCaP95 cell growth suppression using an MTT assay (mitochondrial respiration) read at 72 and 96 hrs after addition of BKIs. Cells were be plated in 96 well plates at 2500 cells/well in 10% FBS and RPMI-1640 with insulin/transferrin/and selenium added. Each cell line was be tested in quadruplicate.

Several compounds suppressed LNCaP95 cell growth between 40-90% at 10 μM concentration (e.g., compounds of Examples 7, 15, 18, 24, 25, 39, 58, 109, 110, 118, 119, 121, 122, 124, 123, 127, 128); and five compounds screened showed greater than 50% inhibition of LNCaP95 cells. Example 24 compound (FIG. 1) was chosen as a lead compound. Example 24 has an $IC_{50}$ of 0.15 uM inhibition of PKD3, reaches inhibitory blood levels in mice and calves after a single oral dose with no identifiable toxicity after 4 weeks every other day treatment (FIG. 2).

Figure 2:
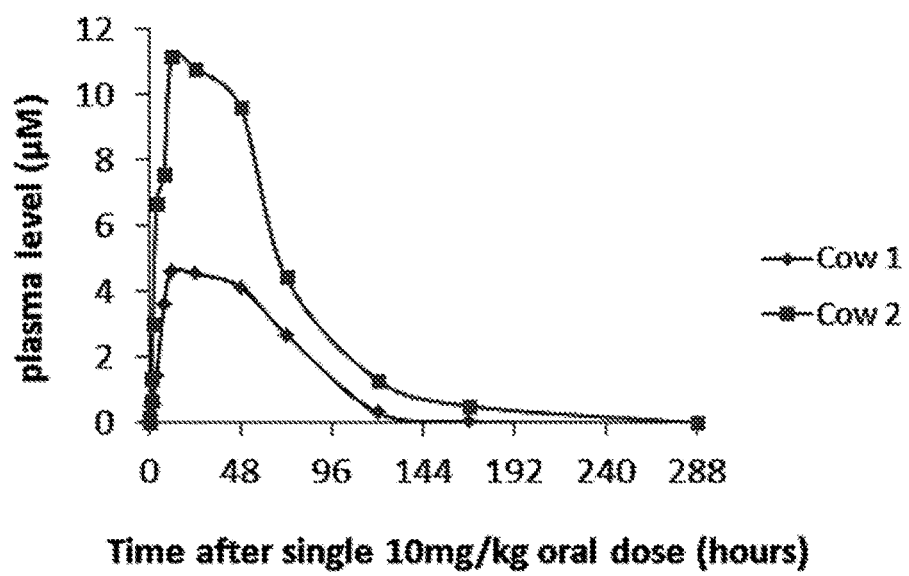
FIG. 2 shows mean plasma concentrations of Example 24 compound. (A) Example 24 concentrations after oral dosing with 30 mg/kg once daily for 5 days in mice. (B) Example 24 plasma serum level concentrations after a single oral dose (10 mg/kg) in calves.

Studies demonstrated similar inhibition of LNCaP cells (FIG. 1). No effect was noted on AR-negative prostate cancer cell lines. BKI was tested against 360 human protein kinases and only PKD3 was targeted. This finding was surprising since it contrasted with recent reports on three known PKD inhibitors, 1NM-PP1, 1NA-PP1, SD-208, which all potently blocked PKD kinase activity and prostate cancer cell growth/proliferation AR– as well as AR+ lines (Tandon et al., 2015). Reasons for differences in selectivity of prostate cancer lines between Example 24 compound and these inhibitors could be due to the off-target effects of the other compounds; 1NM-PP1 and 1NA-PP1 target other human kinases beyond PKDs, including mutated Src, and SD-208 is also a potent inhibitor of TGF-βRI.

Biological Example 2: Effects on AR Transactivation

Figure 3:
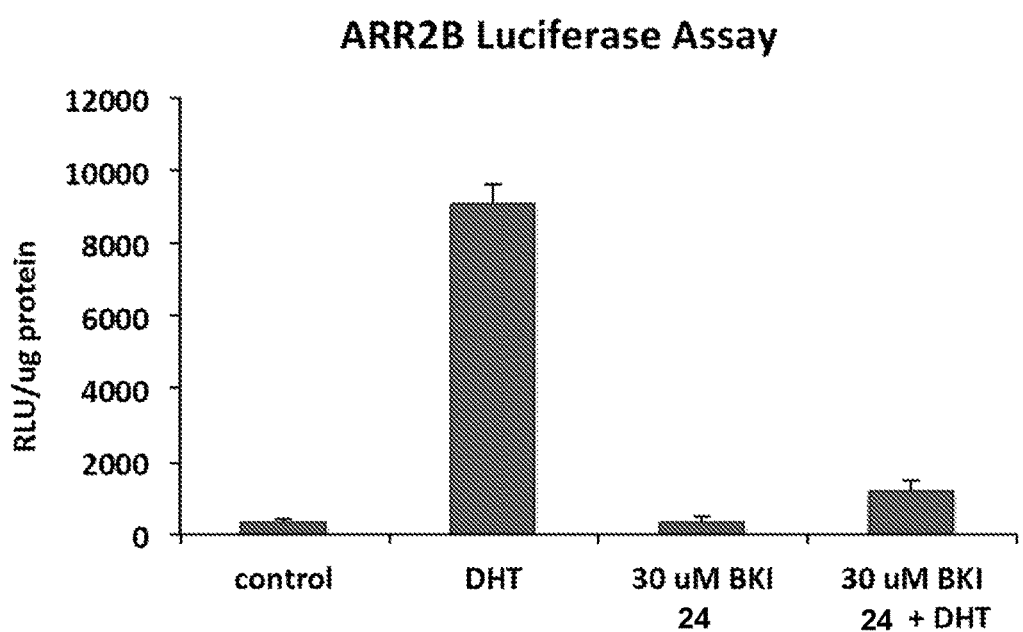
FIG. 3 shows AR transcriptional activity by treatment with Example 24. LNCaP cells were transfected with a probasin luciferase reporter plasmid and then treated with vehicle, dihydrotestosterone (DHT), 24 (30 μM), or 24+DHT for 24 hours. AR is activated by its ligand, DHT.
Figure 4:
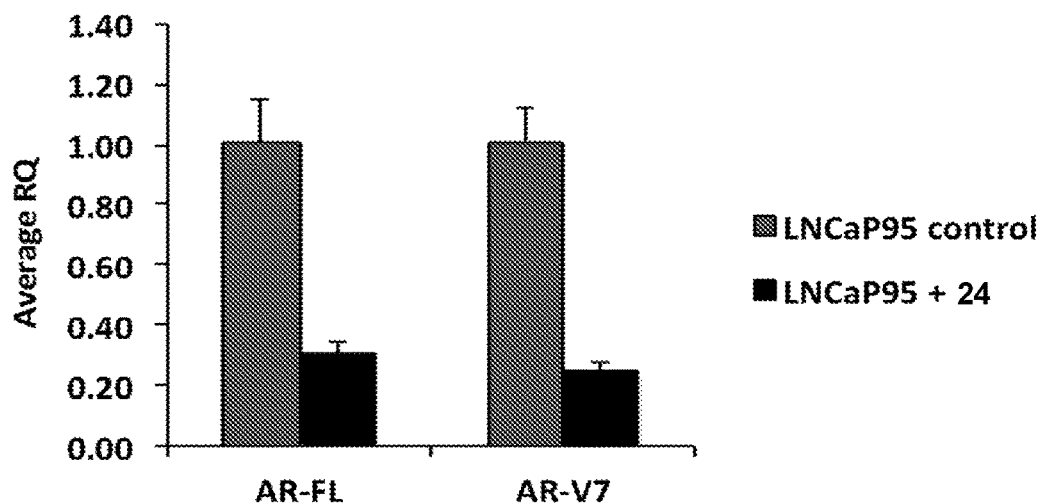
FIG. 4 shows mRNA and protein levels of AR-FL and AR-V7 following Example 24 treatment. (A) Quantitative RT-PCR of mRNA from LNCaP95 cells with and without addition of 24 (30 μM). Note marked decrease in mRNA for both AR-FL (left) and AR-V7 (right) after addition.
Figure 4:
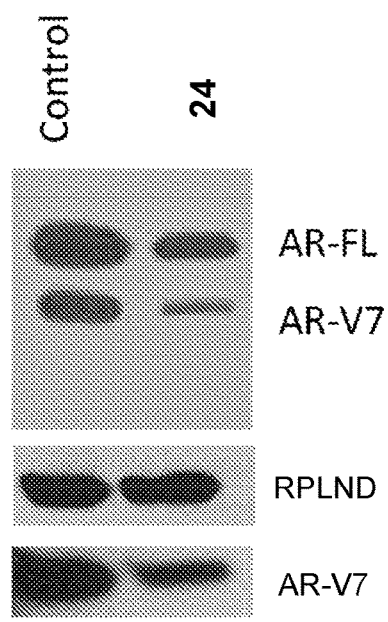

Because BKIs selectively inhibited AR+ prostate cancer cell lines, the effects of Example 24 compound on AR transactivation was examined using the LNCaP cell line. A plasmid containing a probasin promoter linked to a luciferase reporter was used to examine transcriptional activity of the AR. Probasin is one of several genes that is activated by the AR when it is bound to ligand. AR binds to androgen response elements (AREs) in the promoter of such genes to activate transcription of these genes. When AR positive LNCaP prostate cancer cells are treated with Example 24 ARE-luciferase reporter activity decreased, FIG. 3. Interestingly, Example 24 also decreased mRNA and protein levels of AR-FL and AR-V7 mRNA, FIG. 4.

Biological Example 3: Effects on AR Transactivation

Currently there are no good PKD inhibitors on the market, or even in clinical trials. Other PKD inhibitors such as 1NM-PP1 and 1NA-PP1 have low solubility and are quickly metabolized and thus therapeutic levels cannot be obtained in vivo. The newest PKD inhibitor, SD-208, was tested in vivo and did demonstrated a decrease in PCa tumor growth. However, the inhibitor had to be used at a relatively high concentration 60 mg/kg and high dosing frequency (2× daily). Example 24 compound was non-toxic when given at doses exceeding 300 mg/kg to mice. Furthermore, there were no observed adverse effects of Example 24 compound when administered to rats (up to 100 mg/kg) or to calves (10 mg/kg), even with exposures in the 10-30 µM range in plasma. Of note, the newborn calves dosed with BKIs are mono-gastric and their oral drug absorption is a good model for human pharmacokinetics. In a mouse dosing study, it was observed that 20 mg/kg dose given orally exceeded 10 µM plasma levels throughout the 48 hour dosing period. The first xenograft tested was AR-positive LuCaP35 grown in non-castrated mice. This tumor has been shown to be castration-sensitive. A significant suppression of the tumor growth in comparison to vehicle control was seen (not shown). Because the castrate-resistant LNCaP95 line was used to screen BKI compounds in vitro, the same cell line was used next for an in vivo study (4 mice per group). LNCaP95 xenografts were implanted into castrate mice, when tumors reached ~100 mm³, 20 mg/kg was given by gavage 3× weekly, for 6 weeks (the time point at which the tumors in the control group had reached 1000 mm³).

Figure 5:
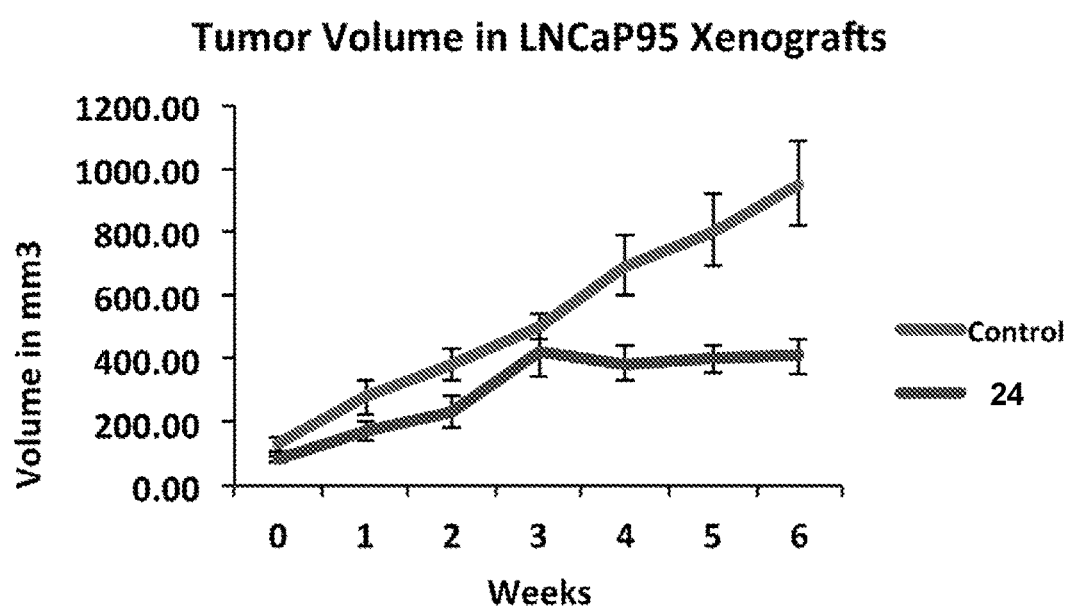
FIG. 5 shows effect on tumor growth in castrate-resistant LNCaP95 xenografts. BKI compound, compound of Example 24 (20 mg/kg) was given by gavage 3× weekly. No toxic side effects were observed over the 6-week period.
Figure 6:
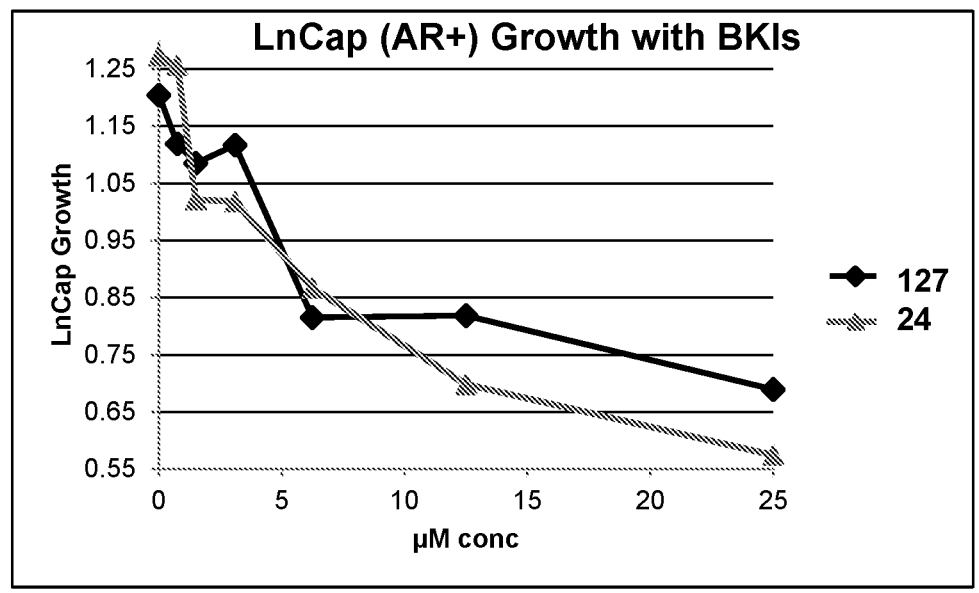
FIG. 6 shows biological activity of Example 24 and Example 127.
Figure 6:
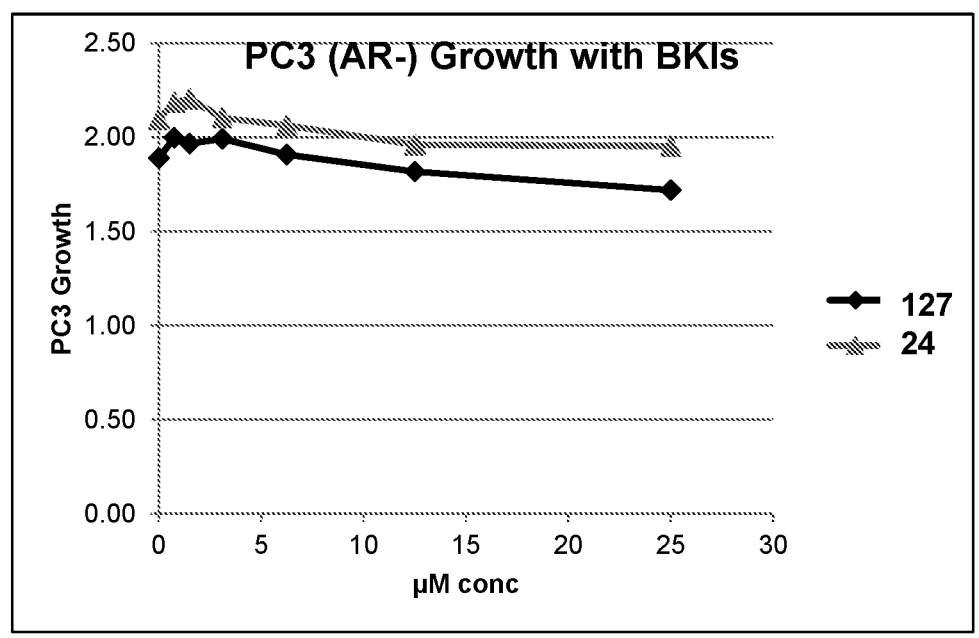

As shown in FIG. 5 there was significant suppression of growth by the end of the study (p<0.005). There were no signs of toxicity in the Example 24 compound treated mice during the 6 weeks of drug therapy. These results suggest that Example 24 compound is safe and effective, and a promising new lead for the therapy of castrate-resistant prostate cancer.

Biological Example 4: Anti-Breast Cancer Activity

MCF7 and MDA231 cell lines were plated at 2000 and 1000 cells/well, respectively. 24 hours later, BKI inhibitor of the disclosure was added to each well at concentrations of 0.2, 2, and 20 µM. After 72 hours, Aldeflour blue was used to measure cell growth. Representative data is provided in Table 2.

TABLE 2

Breast cancer cell proliferation results.

| Example No. | MCF7 cell inhibition (%) | MDA231 cell inhibition (%) |
|---|---|---|
| 51 | 97 | 95 |
| 129 | 75 | 90 |
| 130 | 30 | 80 |
| 120 | 30 | 50 |
| 127 | 50 | 0 |
| 111 | 70 | 90 |
| 16 | 50 | 90 |
| 128 | 40 | 50 |
| 4 | 50 | 60 |
| 15 | 40 | 30 |
| 109 | 50 | 50 |
| 110 | 30 | 10 |
| 25 | 30 | 20 |
| 58 | 50 | 10 |
| 67 | 40 | 0 |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed:

1. A method for treating androgen receptor (AR) positive prostate cancer comprising administering to a patient in need of such treatment a therapeutically effective amount of
   (i) a bumped kinase inhibitor of formula:

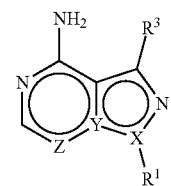

or a pharmaceutically acceptable salt thereof, wherein
X, Y, and Z are defined by either: (i) X is N, Y is C, and Z is N; or (ii) X is C, Y is N, and Z is C(H);
$R^1$ is $C_{2-6}$ alkyl, $C_{1-6}$ haloalkyl, —$C_{1-6}$ alkyl-$R^{12}$, $C_{2-6}$ alkenyl, $C_{2-6}$ alkynyl, $C_{3-8}$ cycloalkyl, heterocyclyl, heteroaryl, or aryl, wherein the alkyl, cycloalkyl, heterocyclyl, heteroaryl, and aryl groups are each optionally substituted with one or two $R^{11}$ groups;

each $R^{11}$ is independently halogen, cyano, nitro, $C_{1-6}$ alkyl, $C_{1-6}$ haloalkyl, —OR, —SR, —NR$_2$, —C(O)R, —C(O)OR, —C(O)NR$_2$, —S(O)$_2$NR$_2$, or S(O)$_2$R; and $R^{12}$ is —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, —N(R)C(O)NR$_2$, aryl, heteroaryl, $C_{3-8}$ cycloalkyl, or heterocyclyl, wherein $R^{12}$ is optionally substituted by one, two, or three groups that are each independently halogen, cyano, nitro, $C_{1-6}$ alkyl, $C_{1-6}$ haloalkyl, $C_{1-6}$ hydoxyalkyl, —OR, —SR, —NR$_2$, —C(O)R, —C(O)OR, —C(O)NR$_2$, —S(O)$_2$R, —OC(O)R, —OC(O)OR, —OC(O)NR$_2$, —N(R)C(O)R, —N(R)C(O)OR, or —N(R)C(O)NR$_2$;

$R^3$ is one of the formulas,

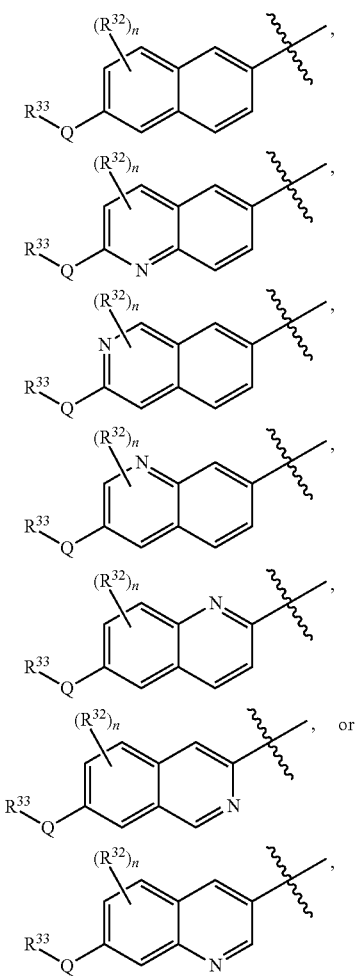

wherein n is 0, 1, or 2;

Q is —O—, —S—, or —N(R$^Q$)—, wherein R$^Q$ is hydrogen or $C_{1-6}$ alkyl; and $R^{33}$ is $C_{1-6}$ alkyl, $C_{2-6}$ alkenyl, $C_{1-6}$ haloalkyl, $C_{3-8}$ cycloalkyl, ($C_{3-8}$ cycloalkyl)$C_{1-6}$ alkyl, heterocyclyl, (heterocyclyl)$C_{1-6}$ alkyl, aryl, arylC$_{1-6}$ alkyl, heteroaryl, or heteroarylC$_{1-6}$ alkyl wherein the alkyl, cycloalkyl, heterocyclyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^{20}$, —SR$^{20}$, —N(R$^{20}$)$_2$, —C(O)R$^{20}$, —C(O)OR$^{20}$, —C(O)N(R$^{20}$)$_2$, —S(O)$_2$R$^{20}$, —OC(O)R$^{20}$, —OC(O)OR$^{20}$, —OC(O)N(R$^{20}$)$_2$, —N(R$^{20}$)C(O)R$^{20}$, —N(R$^{20}$)C(O)OR$^{20}$, or —N(R$^{20}$)C(O)N(R$^{20}$)$_2$, wherein each $R^{20}$ is independently hydrogen or $C_{1-6}$ alkyl, each $R^{32}$ is independently halogen, cyano, nitro, $C_{1-6}$ alkyl, $C_{1-6}$ haloalkyl, —OR$^{34}$, —SR$^{34}$, —N(R$^{34}$)$_2$, —C(O)R$^{34}$, —C(O)OR$^{34}$, —C(O)N(R$^{34}$)$_2$, —S(O)$_2$R$^{34}$, —OC(O)R$^{34}$, —OC(O)OR$^{34}$, —OC(O)N(R$^{34}$)$_2$, —N(R$^{34}$)C(O)R$^{34}$, —N(R$^{34}$)C(O)OR$^{34}$, or —N(R$^{34}$)C(O)N(R$^{34}$)$_2$, wherein each $R^{34}$ is independently hydrogen or $C_{1-6}$ alkyl; and $R^{35}$ is hydrogen or $C_{1-6}$ alkyl;

and each R is independently hydrogen, $C_{1-6}$ alkyl, $C_{2-6}$ alkenyl, $C_{1-6}$ haloalkyl, $C_{3-8}$ cycloalkyl, heterocyclyl, aryl, arylC$_{1-6}$ alkyl, heteroaryl, or heteroarylC$_{1-6}$ alkyl wherein the alkyl, aryl, arylalkyl, heteroaryl, and heteroarylalkyl are optionally substituted with one, two, three, or four groups that are each independently halogen, cyano, nitro, $C_{1-6}$ alkyl, $C_{1-6}$ haloalkyl, —OR$^0$, —SR$^0$, —N(R$^0$)$_2$, —C(O)R$^0$, —C(O)OR$^0$, —C(O)N(R$^0$)$_2$, —S(O)$_2$R$^0$, —OC(O)R$^0$, —OC(O)OR$^0$, —OC(O)N(R$^0$)$_2$, —N(R$^0$)C(O)R$^0$, —N(R$^0$)C(O)OR$^0$, or —N(R$^0$)C(O)N(R$^0$)$_2$, wherein each $R^0$ is independently hydrogen or $C_{1-6}$ alkyl;

(ii) a pharmaceutical composition comprising the bumped kinase inhibitor and a pharmaceutically acceptable excipient, carrier, or diluent.

2. The method of claim 1, wherein the prostate cancer is androgen therapy resistant.

3. The method of claim 1, wherein the prostate cancer is castrate resistant prostate cancer (CRPC).

4. The method of claim 1, wherein the bumped kinase inhibitor is of the formula

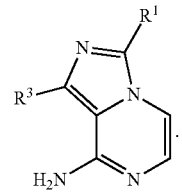

5. The method of claim 1, wherein the bumped kinase inhibitor is of the formula

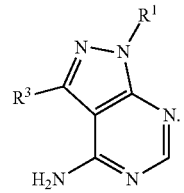

6. The method of claim 1, wherein $R^3$ is of the formula

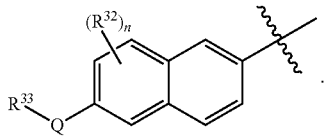

7. The method of claim 6, wherein Q is —O— or —N($R^Q$)—.

8. The method of claim 6, wherein $R^{33}$ is $C_{1-6}$ alkyl, $C_{2-6}$ alkenyl, $C_{3-8}$ cycloalkyl, aryl$C_{1-6}$ alkyl, or heteroaryl$C_{1-6}$ alkyl, wherein the cycloalkyl, arylalkyl and heteroarylalkyl are optionally substituted with one, two, three, or four groups that are each independently halogen, cyano, nitro, $C_{1-6}$ alkyl, $C_{1-6}$ haloalkyl, —O$R^{20}$, —S$R^{20}$, —N($R^{20}$)$_2$, —C(O)$R^{20}$, —C(O)O$R^{20}$, —C(O)N($R^{20}$)$_2$, —S(O)$_2R^{20}$, —OC(O)$R^{20}$, —OC(O)O$R^{20}$, —OC(O)N($R^{20}$)$_2$, —N($R^{20}$)C(O)$R^{20}$, —N($R^{20}$)C(O)O$R^{20}$, or —N($R^{20}$)C(O)N($R^{20}$)$_2$, wherein each $R^{20}$ is independently hydrogen or $C_{1-6}$ alkyl.

9. The method of claim 1, wherein $R^1$ is $C_{2-6}$ alkyl or —$C_{1-4}$ alkyl-$R^{12}$.

10. The method of claim 9, wherein $R^{12}$ is —OR or heterocyclyl, each optionally substituted.

11. The method of claim 1, wherein the bumped kinase inhibitor is:
1-(6-ethoxynaphthalen-2-yl)-3-isopropylimidazo[1,5-a]pyrazin-8-amine;
3-(6-isopropoxynaphthalen-2-yl)-1-isopropyl-1H-pyrazolo[3,4-d]pyrimidin-4-amine;
1-isopropyl-3-(6-propoxynaphthalen-2-yl)-1H-pyrazolo[3,4-d]pyrimidin-4-amine;
1-isopropyl-3-(6-methoxynaphthalen-2-yl)-1H-pyrazolo[3,4-d]pyrimidin-4-amine;
3-(6-ethoxynaphthalen-2-yl)-1-isopropyl-1H-pyrazolo[3,4-d]pyrimidin-4-amine;
3-(naphthalen-2-yl)-1-(piperidin-4-ylmethyl)-1H-pyrazolo[3,4-d]pyrimidin-4-amine
3-(6-methoxynaphthalen-2-yl)-1-(piperidin-4-ylmethyl)-1H-pyrazolo[3,4-d]pyrimidin-4-amine;
3-(6-ethoxynaphthalen-2-yl)-1-(piperidin-4-ylmethyl)-1H-pyrazolo[3,4-d]pyrimidin-4-amine;
3-(6-ethoxynaphthalen-2-yl)-1-((1-methylpiperidin-4-yl)methyl)-1H-pyrazolo[3,4-d]pyrimidin-4-amine;
3-(6-isopropoxynaphthalen-2-yl)-1-(piperidin-4-ylmethyl)-1H-pyrazolo[3,4-d]pyrimidin-4-amine;
1-(piperidin-4-ylmethyl)-3-(6-propoxynaphthalen-2-yl)-1H-pyrazolo[3,4-d]pyrimidin-4-amine;
3-(6-(benzyloxy)naphthalen-2-yl)-1-(piperidin-4-ylmethyl)-1H-pyrazolo[3,4-d]pyrimidin-4-amine;
3-(6-butoxynaphthalen-2-yl)-1-(piperidin-4-ylmethyl)-1H-pyrazolo[3,4-d]pyrimidin-4-amine;
3-(6-(allyloxy)naphthalen-2-yl)-1-(piperidin-4-ylmethyl)-1H-pyrazolo[3,4-d]pyrimidin-4-amine;
3-(6-(2-chlorobenzyloxy)naphthalen-2-yl)-1-(piperidin-4-ylmethyl)-1H-pyrazolo[3,4-d]pyrimidin-4-amine;
3-(6-(3-chlorobenzyloxy)naphthalen-2-yl)-1-(piperidin-4-ylmethyl)-1H-pyrazolo[3,4-d]pyrimidin-4-amine;
3-(6-(4-chlorobenzyloxy)naphthalen-2-yl)-1-(piperidin-4-ylmethyl)-1H-pyrazolo[3,4-d]pyrimidin-4-amine;
3-(6-(benzyloxy)naphthalen-2-yl)-isopropyl-1H-pyrazolo[3,4-d]pyrimidin-4-amine;
3-(6-(allyloxy)naphthalen-2-yl)-1-isopropyl-1H-pyrazolo[3,4-d]pyrimidin-4-amine;
3-(6-butoxynaphthalen-2-yl)-isopropyl-1H-pyrazolo[3,4-d]pyrimidin-4-amine;
3-(6-isobutoxynaphthalen-2-yl)-1-isopropyl-1H-pyrazolo[3,4-d]pyrimidin-4-amine;
3-(6-isobutoxynaphthalen-2-yl)-1-(piperidin-4-ylmethyl)-1H-pyrazolo[3,4-d]pyrimidin-4-amine;
3-(6-(2-chlorobenzyloxy)naphthalen-2-yl)-1-isopropyl-1H-pyrazolo[3,4-d]pyrimidin-4-amine;
3-(6-(3-chlorobenzyloxy)naphthalen-2-yl)-1-isopropyl-1H-pyrazolo[3,4-d]pyrimidin-4-amine;
3-(6-(2, 5-dimethylbenzyloxy)naphthalen-2-yl)-isopropyl-1H-pyrazolo[3,4-d]pyrimidin-4-amine;
1-isopropyl-3-(6-(2-methylbenzyloxy)naphthalen-2-yl)-1H-pyrazolo[3,4-d]pyrimidin-4-amine;
1-isopropyl-3-(6-(2-methyl-5-(trifluoromethyl)benzyloxy)naphthalen-2-yl)-1H-pyrazolo[3,4-d]pyrimidin-4-amine;
3-(6-(3-chloro-4-(2,2,2-trifluoroethyl)benzyloxy)naphthalen-2-yl)-1-isopropyl-1H-pyrazolo[3,4-d]pyrimidin-4-amine;
3-(6-(3-chloro-5-fluorobenzyloxy)naphthalen-2-yl)-1-isopropyl-1H-pyrazolo[3,4-d]pyrimidin-4-amine;
1-isopropyl-3-(6-(1-phenylethoxy)naphthalen-2-yl)-1H-pyrazolo[3,4-d]pyrimidin-4-amine;
3-(6-(4-tert-butylbenzyloxy)naphthalen-2-yl)-1-isopropyl-1H-pyrazolo[3,4-d]pyrimidin-4-amine;
1-isopropyl-3-(6-(pyridin-4-ylmethoxy)naphthalen-2-yl)-1H-pyrazolo[3,4-d]pyrimidin-4-amine;
3-(6-(4-chlorobenzyloxy)naphthalen-2-yl)-1-isopropyl-1H-pyrazolo[3,4-d]pyrimidin-4-amine;
6-(4-amino-1-(piperidin-4-ylmethyl)-1H-pyrazolo[3,4-d]pyrimidin-3-yl)-N,N-dimethylquinolin-2-amine;
3-tert-butyl-1-(6-ethoxynaphthalen-2-yl)imidazo[1,5-a]pyrazin-8-amine;
3-tert-butyl-1-(6-methoxynaphthalen-2-yl)imidazo[1,5-a]pyrazin-8-amine;
3-(2-methoxyquinolin-6-yl)-1-((tetrahydro-2H-pyran-4-yl)methyl)-1H-pyrazolo[3,4-d]pyrimidin-4-amine;
3-(2-(cyclopropylmethoxy)quinolin-6-yl)-1-((tetrahydro-2H-pyran-4-yl)methyl)-1H-pyrazolo[3,4-d]pyrimidin-4-amine;
3-(6-(cyclopropylmethoxy)naphthalen-2-yl)-1-((tetrahydro-2H-pyran-4-yl)methyl)-1H-pyrazolo[3,4-d]pyrimidin-4-amine;
3-(6-cyclobutoxynaphthalen-2-yl)-1-((tetrahydro-2H-pyran-4-yl)methyl)-1H-pyrazolo[3,4-d]pyrimidin-4-amine;
3-(6-(oxetan-3-yloxy)naphthalen-2-yl)-1-((tetrahydro-2H-pyran-4-yl)methyl)-1H-pyrazolo[3,4-d]pyrimidin-4-amine;
3-(6-cyclopropoxynaphthalen-2-yl)-1-((tetrahydro-2H-pyran-4-yl)methyl)-1H-pyrazolo[3,4-d]pyrimidin-4-amine;
3-(6-ethoxynaphthalen-2-yl)-1-isobutyl-1H-pyrazolo[3,4-d]pyrimidin-4-amine;
1-(4-amino-3-(6-ethoxynaphthalen-2-yl)-1H-pyrazolo[3,4-d]pyrimidin-1-yl)-2-methylpropan-2-ol;
3-(6-cyclopropoxynaphthalen-2-yl)-isobutyl-1H-pyrazolo[3,4-d]pyrimidin-4-amine;
3-(4-amino-3-(6-ethoxynaphthalen-2-yl)-1H-pyrazolo[3,4-d]pyrimidin-1-yl)-2,2-dimethylpropan-1-ol;
3-(4-amino-3-(6-cyclopropoxynaphthalen-2-yl)-1H-pyrazolo[3,4-d]pyrimidin-1-yl)-2,2-dimethylpropan-1-ol;
1-(6-(4-amino-isobutyl-1H-pyrazolo[3,4-d]pyrimidin-3-yl)naphthalen-2-yloxy)-2-methylpropan-2-ol;
2-(6-(4-amino-1-isobutyl-1H-pyrazolo[3,4-d]pyrimidin-3-yl)naphthalen-2-yloxy)ethanol;

1-isobutyl-3-(6-(oxetan-3-yloxy)naphthalen-2-yl)-1H-pyrazolo[3,4-d]pyrimidin-4-amine;
1-isobutyl-3-(6-(2-methoxyethoxy)naphthalen-2-yl)-1H-pyrazolo[3,4-d]pyrimidin-4-amine;
3-(4-amino-3-(2-ethoxyquinolin-6-yl)-1H-pyrazolo[3,4-d]pyrimidin-1-yl)-2,2-dimethylpropan-1-ol;
1-(4-amino-3-(2-ethoxyquinolin-6-yl)-1H-pyrazolo[3,4-d]pyrimidin-1-yl)-2-methylpropan-2-ol;
3-(2-(2-methoxyethoxy)quinolin-6-yl)-1-neopentyl-1H-pyrazolo[3,4-d]pyrimidin-4-amine;
3-(4-Amino-3-(2-cyclopropoxyquinolin-6-yl)-1H-pyrazolo[3,4-d]pyrimidin-1-yl)-2,2-dimethylpropan-1-ol;
3-(2-cyclopropoxyquinolin-6-yl)-1-(piperidin-4-ylmethyl)-1H-pyrazolo[3,4-d]pyrimidin-4-amine;
3-(2-cyclopropoxyquinolin-6-yl)-1-((1-methylpiperidin-4-yl)methyl)-1H-pyrazolo[3,4-d]pyrimidin-4-amine;
1-(4-amino-3-(6-cyclopropoxynaphthalen-2-yl)-1H-pyrazolo[3,4-d]pyrimidin-1-yl)-2-methylpropan-2-ol;
3-(2-cyclopropoxyquinolin-6-yl)-1-isobutyl-1H-pyrazolo[3,4-d]pyrimidin-4-amine;
3-(2-cyclopropoxyquinolin-6-yl)-1-((tetrahydro-2H-pyran-4-yl)methyl)-1H-pyrazolo[3,4-d]pyrimidin-4-amine;
1-(azetidin-3-ylmethyl)-3-(2-cyclopropoxyquinolin-6-yl)-1H-pyrazolo[3,4-d]pyrimidin-4-amine;
3-(2-cyclopropoxyquinolin-6-yl)-1-((1-methylazetidin-3-yl)methyl)-1H-pyrazolo[3,4-d]pyrimidin-4-amine;
3-(2-(2-methoxyethoxy)quinolin-6-yl)-14(1-methylpiperidin-4-yl)methyl)-1H-pyrazolo[3,4-d]pyrimidin-4-amine;
1-(4-Amino-3-(2-cyclopropoxyquinolin-6-yl)-1H-pyrazolo[3,4-d]pyrimidin-1-yl)-2-methylpropan-2-ol;
1-isobutyl-3-(2-(2,2,2-trifluoroethoxy)quinolin-6-yl)-1H-pyrazolo[3,4-d]pyrimidin-4-amine;
1-(piperidin-4-ylmethyl)-3-(2-(2,2,2-trifluoroethoxy)quinolin-6-yl)-1H-pyrazolo[3,4-d]pyrimidin-4-amine;
1-((1-methylpiperidin-4-yl)methyl)-3-(2-(2,2,2-trifluoroethoxy)quinolin-6-yl)-1H-pyrazolo[3,4-d]pyrimidin-4-amine;
2-(3-(4-amino-3-(2-cyclopropoxyquinolin-6-yl)-1H-pyrazolo[3,4-d]pyrimidin-1-yl)-2,2-dimethylpropoxy)ethanol;
1-(4-amino-3-(2-(2,2,2-trifluoroethoxy)quinolin-6-yl)-1H-pyrazolo[3,4-d]pyrimidin-1-yl)-2-methylpropan-2-ol;
3-(4-amino-3-(2-(2,2,2-trifluoroethoxy)quinolin-6-yl)-1H-pyrazolo[3,4-d]pyrimidin-1-yl)-2,2-dimethylpropan-1-ol;
3-(2-cyclopropoxyquinolin-6-yl)-1-(3-(dimethylamino)-2,2-dimethylpropyl)-1H-pyrazolo[3,4-d]pyrimidin-4-amine;
3-(7-ethoxynaphthalen-2-yl)-1-isobutyl-1H-pyrazolo[3,4-d]pyrimidin-4-amine;
3-(7-ethoxynaphthalen-2-yl)-1-(piperidin-4-ylmethyl)-1H-pyrazolo[3,4-d]pyrimidin-4-amine;
3-(6-cyclopropoxynaphthalen-2-yl)-1-((3-methyloxetan-3-yl)methyl)-1H-pyrazolo[3,4-d]pyrimidin-4-amine;
3-(6-ethoxynaphthalen-2-yl)-1-((3-methyloxetan-3-yl)methyl)-1H-pyrazolo[3,4-d]pyrimidin-4-amine;
3-(2-cyclopropoxyquinolin-6-yl)-1-((3-methyloxetan-3-yl)methyl)-1H-pyrazolo[3,4-d]pyrimidin-4-amine;
2-(4-amino-3-(6-ethoxynaphthalen-2-yl)-1H-pyrazolo[3,4-d]pyrimidin-1-yl)-1-morpholinoethanone;
2-(4-amino-3-(6-cyclopropoxynaphthalen-2-yl)-1H-pyrazolo[3,4-d]pyrimidin-1-yl)-1-morpholinoethanone;
2-((4-amino-3-(6-(methoxymethyl)naphthalen-2-yl)-1H-pyrazolo[3,4-d]pyrimidin-1-yl)methyl)-1,1,1,3,3,3-hexafluoropropan-2-ol;
2-((4-Amino-3-(6-cyclopropoxynaphthalen-2-yl)-1H-pyrazolo[3,4-d]pyrimidin-1-yl)methyl)-1,1,1,3,3,3-hexafluoropropan-2-ol;
2-((4-amino-3-(2-cyclopropoxyquinolin-6-yl)-1H-pyrazolo[3,4-d]pyrimidin-1-yl)methyl)-1,1,1,3,3,3-hexafluoropropan-2-ol;
1-(3-(6-cyclopropoxynaphthalen-2-yl)-1H-pyrrolo[3,2-c]pyridin-1-yl)-2-methylpropan-2-ol;
1-(4-amino-5-(2-cyclopropoxyquinolin-6-yl)-7H-pyrrolo[2,3-d]pyrimidin-7-yl)-2-methylpropan-2-ol;
4-(4-amino-3-(2-cyclopropoxyquinolin-6-yl)-1H-pyrazolo[3,4-d]pyrimidin-1-yl)-2,3,3-trimethylbutan-2-ol;
1-((4-amino-3-(2-cyclopropoxyquinolin-6-yl)-1H-pyrazolo[3,4-d]pyrimidin-1-yl)methyl)cyclobutanol;
1-(4-amino-5-(6-cyclopropoxynaphthalen-2-yl)-7H-pyrrolo[2,3-d]pyrimidin-7-yl)-2-methylpropan-2-ol;
1-((4-amino-3-(6-cyclopropoxynaphthalen-2-yl)-1H-pyrazolo[3,4-d]pyrimidin-1-yl)methyl)cyclobutanol;
1-((4-amino-3-(2-cyclopropoxyquinolin-6-yl)-1H-pyrazolo[3,4-d]pyrimidin-1-yl)methyl)cyclopentanol;
1-((4-amino-3-(6-cyclopropoxynaphthalen-2-yl)-1H-pyrazolo[3,4-d]pyrimidin-1-yl)methyl)cyclopentanol;
4-((4-amino-3-(2-cyclopropoxyquinolin-6-yl)-1H-pyrazolo[3,4-d]pyrimidin-1-yl)methyl)-tetrahydro-2H-pyran-4-ol;
4-((4-amino-3-(6-cyclopropoxynaphthalen-2-yl)-1H-pyrazolo[3,4-d]pyrimidin-1-yl)methyl)-tetrahydro-2H-pyran-4-ol;
(3-((4-amino-3-(2-cyclopropoxyquinolin-6-yl)-1H-pyrazolo[3,4-d]pyrimidin-1-yl)methyl)oxetan-3-yl)methanol;
(3-((4-amino-3-(6-cyclopropoxynaphthalen-2-yl)-1H-pyrazolo[3,4-d]pyrimidin-1-yl)methyl)oxetan-3-yl)methanol;
3-(6-cyclopropoxynaphthalen-2-yl)-1-(2-methoxy-2-methylpropyl)-1H-pyrazolo[3,4-d]pyrimidin-4-amine;
3-(2-cyclopropoxyquinolin-6-yl)-1-(2-methoxy-2-methylpropyl)-1H-pyrazolo[3,4-d]pyrimidin-4-amine;
methyl 3-(4-amino-3-(6-cyclopropoxynaphthalen-2-yl)-1H-pyrazolo[3,4-d]pyrimidin-1-yl)-2,2-dimethylpropanoate;
methyl 3-(4-amino-3-(2-cyclopropoxyquinolin-6-yl)-1H-pyrazolo[3,4-d]pyrimidin-1-yl)-2,2-dimethylpropanoate;
4-((4-amino-3-(6-ethoxynaphthalen-2-yl)-1H-pyrazolo[3,4-d]pyrimidin-1-yl)methyl)piperidin-4-ol;
4-((4-amino-3-(6-ethoxynaphthalen-2-yl)-1H-pyrazolo[3,4-d]pyrimidin-1-yl)methyl)-1-methylpiperidin-4-ol;
methyl 2-((6-(4-amino-1-((1-methylpiperidin-4-yl)methyl)-1H-pyrazolo[3,4-d]pyrimidin-3-yl)naphthalen-2-yl)oxy)acetate;
2-((6-(4-amino-1-((1-methylpiperidin-4-yl)methyl)-1H-pyrazolo[3,4-d]pyrimidin-3-yl)naphthalen-2-yl)oxy)acetonitrile;
4-((4-amino-3-(6-ethoxynaphthalen-2-yl)-1H-pyrazolo[3,4-d]pyrimidin-1-yl)methyl)piperidine-4-carbonitrile;
4-((4-amino-3-(6-ethoxynaphthalen-2-yl)-1H-pyrazolo[3,4-d]pyrimidin-1-yl)methyl)-1-methylpiperidine-4-carbonitrile;
3-(4-amino-3-(6-cyclopropoxynaphthalen-2-yl)-1H-pyrazolo[3,4-d]pyrimidin-1-yl)-2,2-dimethylpropanoic acid;

3-(6-cyclopropoxynaphthalen-2-yl)-1-(2-fluoro-2-methylpropyl)-1H-pyrazolo[3,4-d]pyrimidin-4-amine;
4-((4-amino-3-(6-cyclopropoxynaphthalen-2-yl)-1H-pyrazolo[3,4-d]pyrimidin-1-yl)methyl)piperidin-4-ol;
4-((4-amino-3-(6-cyclopropoxynaphthalen-2-yl)-1H-pyrazolo[3,4-d]pyrimidin-1-yl)methyl)-1-methylpiperidin-4-ol;
4-((4-amino-3-(2-ethoxyquinolin-6-yl)-1H-pyrazolo[3,4-d]pyrimidin-1-yl)methyl)-1-methylpiperidin-4-ol;
4-((4-amino-3-(2-ethoxyquinolin-6-yl)-1H-pyrazolo[3,4-d]pyrimidin-1-yl)methyl)-1-methylpiperidin-4-ol;
4-((4-amino-3-(2-cyclopropoxyquinolin-6-yl)-1H-pyrazolo[3,4-d]pyrimidin-1-yl)methyl)piperidin-4-ol;
4-((4-amino-3-(6-cyclopropoxynaphthalen-2-yl)-1H-pyrazolo[3,4-d]pyrimidin-1-yl)methyl)-1-methylpiperidine-4-carbonitrile;
4-((4-amino-3-(2-ethoxyquinolin-6-yl)-1H-pyrazolo[3,4-d]pyrimidin-1-yl)methyl)piperidin-4-ol;
4-((4-amino-3-(2-cyclopropoxyquinolin-6-yl)-1H-pyrazolo[3,4-d]pyrimidin-1-yl)methyl)-1-methylpiperidin-4-ol;
4-((4-amino-3-(2-ethoxyquinolin-6-yl)-1H-pyrazolo[3,4-d]pyrimidin-1-yl)methyl)piperidine-4-carbonitrile;
4-((4-amino-3-(2-ethoxyquinolin-6-yl)-1H-pyrazolo[3,4-d]pyrimidin-1-yl)methyl)-1-methylpiperidine-4-carbonitrile;
2-(6-(4-amino-1-(2-hydroxy-2-methylpropyl)-1H-pyrazolo[3,4-d]pyrimidin-3-yl)naphthalen-2-yloxy)acetonitrile;
methyl 2-(6-(4-amino-1-(piperidin-4-ylmethyl)-1H-pyrazolo[3,4-d]pyrimidin-3-yl)quinolin-2-yloxy)acetate;
3-((4-amino-3-(6-cyclopropoxynaphthalen-2-yl)-1H-pyrazolo[3,4-d]pyrimidin-1-yl)methyl)azetidin-3-ol;
3-((4-amino-3-(6-cyclopropoxynaphthalen-2-yl)-1H-pyrazolo[3,4-d]pyrimidin-1-yl)methyl)-1-methylazetidin-3-ol;
4-((4-amino-3-(2-cyclopropoxyquinolin-6-yl)-1H-pyrazolo[3,4-d]pyrimidin-1-yl)methyl)-1-methylpiperidine-4-carbonitrile;
3-((4-amino-3-(2-ethoxyquinolin-6-yl)-1H-pyrazolo[3,4-d]pyrimidin-1-yl)methyl)azetidin-3-ol;
3-(6-(difluoromethoxy)naphthalen-2-yl)-1-(piperidin-4-ylmethyl)-1H-pyrazolo[3,4-d]pyrimidin-4-amine;
3-(6-(difluoromethoxy)naphthalen-2-yl)-1-((1-methylpiperidin-4-yl)methyl)-1H-pyrazolo[3,4-d]pyrimidin-4-amine;
3-((4-amino-3-(6-ethoxynaphthalen-2-yl)-1H-pyrazolo[3,4-d]pyrimidin-1-yl)methyl)azetidin-3-ol;
3-((4-amino-3-(6-ethoxynaphthalen-2-yl)-1H-pyrazolo[3,4-d]pyrimidin-1-yl)methyl)-1-methylazetidin-3-ol;
4-((4-amino-3-(6-(difluoromethoxy)naphthalen-2-yl)-1H-pyrazolo[3,4-d]pyrimidin-1-yl)methyl)piperidin-4-ol;
4-((4-amino-3-(6-(difluoromethoxy)naphthalen-2-yl)-1H-pyrazolo[3,4-d]pyrimidin-1-yl)methyl)-1-methylpiperidin-4-ol;
4-((4-amino-3-(6-(difluoromethoxy)naphthalen-2-yl)-1H-pyrazolo[3,4-d]pyrimidin-1-yl)methyl)piperidine-4-carbonitrile;
3-((4-amino-3-(2-cyclopropoxyquinolin-6-yl)-1H-pyrazolo[3,4-d]pyrimidin-1-yl)methyl)azetidin-3-ol;
4-((4-amino-3-(6-(difluoromethoxy)naphthalen-2-yl)-1H-pyrazolo[3,4-d]pyrimidin-1-yl)methyl)-1-methylpiperidine-4-carbonitrile;
3-((4-amino-3-(2-cyclopropoxyquinolin-6-yl)-1H-pyrazolo[3,4-d]pyrimidin-1-yl)methyl)-1-methylazetidin-3-ol;
1-(3-(6-ethoxynaphthalen-2-yl)-1-((1-(methylcarbamoyl)piperidin-4-yl)methyl)-1H-pyrazolo[3,4-d]pyrimidin-4-yl)-3-methylurea;
4-((4-amino-3-(2-ethoxyquinolin-6-yl)-1H-pyrazolo[3,4-d]pyrimidin-1-yl)methyl)-N-methylpiperidine-1-carboxamide;
3-(6-ethoxynaphthalen-2-yl)-1-(1-ethylpiperidin-4-yl)-1H-pyrazolo[3,4-d]pyrimidin-4-amine;
3-(2-ethoxyquinolin-6-yl)-1-isopropyl-1H-pyrazolo[3,4-d]pyrimidin-4-amine;
3-(6-ethoxynaphthalen-2-yl)-1-(piperidin-4-yl)-1H-pyrazolo[3,4-d]pyrimidin-4-amine;
3-(6-ethoxynaphthalen-2-yl)-1-(1-methylpiperidin-4-yl)-1H-pyrazolo[3,4-d]pyrimidin-4-amine;
3-(6-ethoxynaphthalen-2-yl)-1-(2-(piperidin-4-yl)ethyl)-1H-pyrazolo[3,4-d]pyrimidin-4-amine;
3-(6-ethoxynaphthalen-2-yl)-1-(2-(1-methylpiperidin-4-yl)ethyl)-1H-pyrazolo[3,4-d]pyrimidin-4-amine;
3-(6-ethoxynaphthalen-2-yl)-1-(2-(1-ethylpiperidin-4-yl)ethyl)-1H-pyrazolo[3,4-d]pyrimidin-4-amine;
3-(6-ethoxynaphthalen-2-yl)-1-(2-(1-propylpiperidin-4-yl)ethyl)-1H-pyrazolo[3,4-d]pyrimidin-4-amine;
1-(2-(1-(3-aminopropyl)piperidin-4-yl)ethyl)-3-(6-ethoxynaphthalen-2-yl)-1H-pyrazolo[3,4-d]pyrimidin-4-amine;
3-(6-ethoxynaphthalen-2-yl)-1-(1-propylpiperidin-4-yl)-1H-pyrazolo[3,4-d]pyrimidin-4-amine;
1-(1-(3-aminopropyl)piperidin-4-yl)-3-(6-ethoxynaphthalen-2-yl)-1H-pyrazolo[3,4-d]pyrimidin-4-amine;
1-(6-ethoxynaphthalen-2-yl)-3-(piperidin-4-ylmethyl)imidazo[1,5-a]pyrazin-8-amine;
1-(6-ethoxynaphthalen-2-yl)-3-((1-methylpiperidin-4-yl)methyl)imidazo[1,5-a]pyrazin-8-amine;
1-isopropyl-3-(6-(oxetan-3-yloxy)naphthalen-2-yl)-1H-pyrazolo[3,4-d]pyrimidin-4-amine;
3-(6-cyclopropoxynaphthalen-2-yl)-1-(1-methylpiperidin-4-yl)methyl)-1H-pyrazolo[3,4-d]pyrimidin-4-amine;
1-((6-(4-amino-1-isopropyl-1H-pyrazolo[3,4-d]pyrimidin-3-yl)naphthalen-2-yl)oxy)-2-methylpropan-2-ol;
2-((6-(4-amino-1-isopropyl-1H-pyrazolo[3,4-d]pyrimidin-3-yl)naphthalen-2-yl)oxy)ethan-1-ol;
3-(6-(cyclopropylmethoxy)naphthalen-2-yl)-1-((1-methylpiperidin-4-yl)methyl)-1H-pyrazolo[3,4-d]pyrimidin-4-amine;
3-(6-cyclobutoxynaphthalen-2-yl)-1-(1-methylpiperidin-4-yl)methyl)-1H-pyrazolo[3,4-d]pyrimidin-4-amine;
3-(6-(2-methoxyethoxy)naphthalen-2-yl)-1-((1-methylpiperidin-4-yl)methyl)-1H-pyrazolo[3,4-d]pyrimidin-4-amine;
1-((1-methylpiperidin-4-yl)methyl)-3-(6-(oxetan-3-yloxy)naphthalen-2-yl)-1H-pyrazolo[3,4-d]pyrimidin-4-amine;
2-(6-(4-amino-1-((1-methylpiperidin-4-yl)methyl)-1H-pyrazolo[3,4-d]pyrimidin-3-yl)naphthalen-2-yloxy)ethanol;
1-(6-(4-amino-1-((1-methylpiperidin-4-yl)methyl)-1H-pyrazolo[3,4-d]pyrimidin-3-yl)naphthalen-2-yloxy)-2-methylpropan-2-ol;
3-(2-methoxyquinolin-6-yl)-1-((tetrahydro-2H-pyran-4-yl)methyl)-1H-pyrazolo[3,4-d]pyrimidin-4-amine;
3-(2-(cyclopropylmethoxy)quinolin-6-yl)-1-((tetrahydro-2H-pyran-4-yl)methyl)-1H-pyrazolo[3,4-d]pyrimidin-4-amine;
and pharmaceutically acceptable salts thereof.

12. The method of claim 1, wherein the bumped kinase inhibitor is:

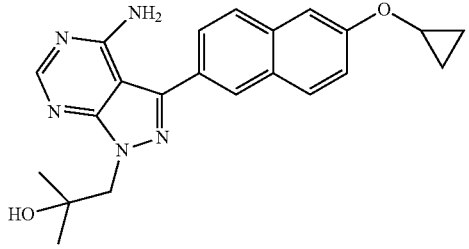 [SMILES: CC(C)(O)Cn1nc(-c2ccc3cc(OC4CC4)ccc3c2)c2c(N)ncnc21]

1-(4-amino-3-(6-cyclopropoxynaphthalen-2-yl)-1H-pyrazolo[3,4-d]pyrimidin-1-yl)-2-methylpropan-2-ol;

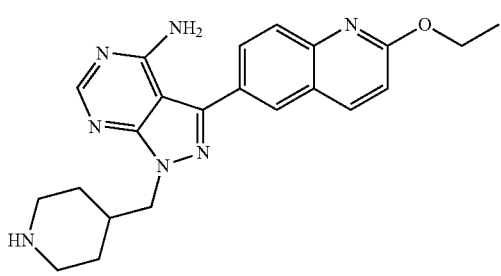 [SMILES: CCOc1ccc2cc(-c3nn(CC4CCNCC4)c4ncnc(N)c34)ccc2n1]

3-(2-ethoxyquinolin-6-yl)-1-(piperidin-4-ylmethyl)-1H-pyrazolo[3,4-d]pyrimidin-4-amine;

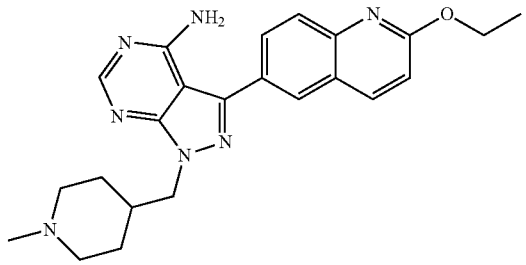 [SMILES: CCOc1ccc2cc(-c3nn(CC4CCN(C)CC4)c4ncnc(N)c34)ccc2n1]

3-(2-ethoxyquinolin-6-yl)-1-(1-methylpiperidin-4-yl)methyl)-1H-pyrazolo[3,4-d]pyrimidin-4-amine;

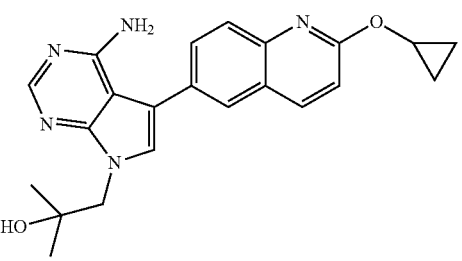 [SMILES: CC(C)(O)Cn1cc(-c2ccc3nc(OC4CC4)ccc3c2)c2c(N)ncnc21]

1-(4-amino-5-(2-cyclopropoxyquinolin-6-yl)-7H-pyrrolo[2,3-d]pyrimidin-7-yl)-2-methylpropan-2-ol;
and pharmaceutically acceptable salts thereof.

* * * * *

UNITED STATES PATENT AND TRADEMARK OFFICE
CERTIFICATE OF CORRECTION

PATENT NO. : 10,350,211 B2
APPLICATION NO. : 15/544598
DATED : July 16, 2019
INVENTOR(S) : Van Voorhis et al.

Page 1 of 1

It is certified that error appears in the above-identified patent and that said Letters Patent is hereby corrected as shown below:

In the Specification

Column 69, Lines 23 to 41, the portion of the formula reading:

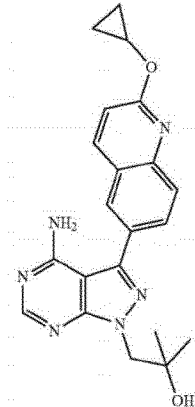

Should read:

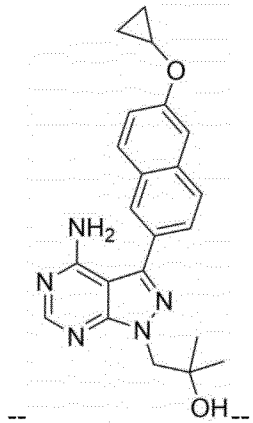

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*